US007838543B2

(12) United States Patent
Beck et al.

(10) Patent No.: US 7,838,543 B2
(45) Date of Patent: Nov. 23, 2010

(54) MCH RECEPTOR ANTAGONISTS

(75) Inventors: James Peter Beck, Indianapolis, IN (US); Brian David Wakefield, Skokie, IL (US); Frederic Laurent Cordier, Alcobendas (ES); Esteban Dominguez-Manzanares, Alcobendas (ES); Kevin Matthew Gardinier, Fishers, IN (US); Peter Michael Greenen, Indianapolis, IN (US); Kenneth Allen Savin, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 578 days.

(21) Appl. No.: 11/719,576

(22) PCT Filed: Dec. 16, 2005

(86) PCT No.: PCT/US2005/045864

§ 371 (c)(1),
(2), (4) Date: May 17, 2007

(87) PCT Pub. No.: WO2006/066173

PCT Pub. Date: Jun. 22, 2006

(65) Prior Publication Data

US 2009/0170913 A1  Jul. 2, 2009

(51) Int. Cl.
*A01N 43/78* (2006.01)
*A61K 31/425* (2006.01)
*C07D 417/00* (2006.01)
*C07D 277/60* (2006.01)

(52) U.S. Cl. .................. 514/367; 548/162; 548/152

(58) Field of Classification Search ................ 514/367; 548/162, 152

See application file for complete search history.

(56) References Cited

U.S. PATENT DOCUMENTS

| 7,053,148 B2 | 5/2006 | Dirschl et al. |
| 2003/0158177 A1 | 8/2003 | Ishihara et al. |
| 2004/0077628 A1 | 4/2004 | Ishihara et al. |
| 2005/0222161 A1 | 10/2005 | Morlya et al. |

FOREIGN PATENT DOCUMENTS

| EP | 1 553 089 | 7/2005 |
| WO | WO 95/32967 | 12/1995 |
| WO | WO 98/38156 | 9/1998 |
| WO | WO 01/21577 | 3/2001 |
| WO | WO 01/57008 | 8/2001 |
| WO | WO 02/42273 | 5/2002 |
| WO | WO 03/049702 | 6/2003 |
| WO | WO 2004/063155 | 7/2004 |

OTHER PUBLICATIONS

Souers, et al., "Identification of 2-(4-Benzyloxyphenyl)-N-[1-(2-pyrrolidin-1-yl-ethyl)-1H-indazol-6-yl]acetamide, an Orally Efficacious Melanin-Concentrating Hormone Receptor 1 Antagonist for the Treatment of Obesity," J. Med. Chem., vol. 48, No. 5, pp. 1318-1321 (2005).

*Primary Examiner*—Sreeni Padmanabhan
*Assistant Examiner*—Umamaheswari Ramachandran
(74) *Attorney, Agent, or Firm*—Francis O. Ginah

(57) ABSTRACT

The present invention relates to a melanin concentrating hormone antagonist compound of formula (I); wherein $Ar^1$, $L_1$, $R^1$, q, X, $R^2$, $R^3$, $R^4$, and $R^5$ are as defined, or a pharmaceutically acceptable salt, solvate, or enantiomer thereof useful in the treatment, prevention or amelioration of symptoms associated with obesity and related diseases.

10 Claims, No Drawings

MCH RECEPTOR ANTAGONISTS

FIELD OF INVENTION

The present invention is in the field of medicine, particularly in the treatment of obesity and diseases caused by or exacerbated by obesity. More specifically, the present invention relates to antagonists of melanin concentrating hormone useful in the prevention and treatment of obesity and related diseases.

BACKGROUND OF THE INVENTION

The affluence of the 1990's along with the exponential increase in food production particularly in Western and Asian economies has resulted in feeding patterns that lead to obesity. Obesity is defined as being excessively overweight. Excessive weight is generally characterized by excessive body fat, because unused energy is stored in the adipose tissues as fat.

Obesity has associated with it, economic and social costs. Obese people, an increasing proportion of developed and developing societies, are regarded as having out of control feeding habits often associated with low self-esteem. Moreover, obese persons are more likely to have medical problems associated with or exacerbated by the excess body weight. Examples of medical conditions caused, exacerbated or triggered by excessive weight include bone fractures, pains in the knee joints, arthritis, increased risk of hypertension, atherosclerosis, stroke, diabetes, etc.

BACKGROUND OF THE INVENTION

Melanin concentrating hormone (MCH) is a 19 amino acid neuropeptide produced in the lateral hypothalamic area and zona incerta, although MCH-expressing neurons project to numerous regions of the brain. MCH is processed from a larger pre-prohormone that also includes a second peptide, NEI, and possibly a third, NGE (Nahon, Crit. Rev in Neurobiology, 8:221-262, 1994). MCH mediates its effects through at least two G protein-coupled receptors, MCHR1 and MCHR2 (Saito et al. Nature 400: 265-269, 1999; Hill et al., J. Biol. Chem. 276: 20125-20129, 2001). Both receptors are expressed in regions of the brain consistent with MCH neuronal projection and known MCH physiologic function (Hervieu et al., Eur J Neuroscience 12: 1194-1216, 2000; Hill et al., J Biol Chem 276: 20125-20129, 2001; Sailer et al., Proc Nat Acad Sci 98: 7564-7569, 2001).

Extensive evidence exists to support the orexigenic activity of MCH. MCH mRNA is elevated in rodent models of obesity and in the fasted state (Qu et al., Nature 380: 243-247, 1996). Intra-cerebroventricularly administered MCH increases feeding and blocks the anorexic effect of α-melanocyte stimulating hormone (Ludwig et al., Am J Physiol 274: E627-E633, 1998). MCH knock-out mice (MCH$^{-/-}$ mice) are lean, hypophagic and hypometabolic (Shimada et al., Nature 396: 670-674, 1998), while MCH over-expressing transgenic mice are obese and insulin resistant (Ludwig et al., J Clin Invest 107: 379-386, 2001). MCER1$^{-/-}$ mice have recently been reported to be lean and hypermetabolic, indicating that the R1 isoform mediates at least some of the metabolic effects of MCH (Marsh et al., Proc Nat Acad Sci 99: 3240-3245, 2002).

In addition to its effects on feeding, MCH has been implicated in regulation of the hypothalamic-pituitary-adrenal axis through modulation of CRF and ACTH release (Bluet-Pajot et al., J Neuroendocrinol 7: 297-303, 1995). MCH may also play a role in the modulation of reproductive function (Murray et al., J Neuroendocrinol 12: 217-223, 2000) and memory (Monzon et al., Peptides 20: 1517-1519, 1999).

The current preferred treatment for obesity as well as Type II non-insulin dependent diabetes is diet and exercise with a view toward weight reduction and improved insulin sensitivity for diabetics. Patient compliance, however, is usually poor. The problem is compounded by the fact that there are currently only two medications approved for the treatment of obesity (sibutramine, or Meridia™ and orlistat, or Xenical™.

PCT application number WO 01/87834, filed May 15, 2001, also discloses compounds reportedly useful as antagonists of the MCH receptor. In particular the WO 01/87834 application claims a compound of formula C.

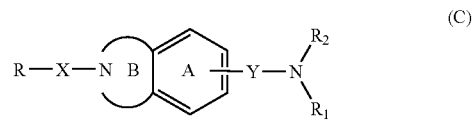

(C)

wherein;

R represents hydrogen, halogen, or an optionally substituted cyclic group; X represents a bond or a spacer in which the main chain has one to ten atoms; Y represents a spacer in which the main chain has one to six atoms; ring A represents a benzene ring which may have other substituents; ring B represents a five- to nine-membered nitrogenous non-aromatic heterocycle which may have other substituents; and $R^1$ and $R^2$ are the same or different and each represents hydrogen, an optionally substituted hydrocarbon group, or an optionally substituted heterocyclic group, or $R^1$ and $R^2$ may form an optionally substituted nitrogenous heterocycle in cooperation with the adjacent nitrogen atom and $R^2$ may form an optionally substituted nitrogenous heterocycle in cooperation with the adjacent nitrogen atom and Y.

PCT application WO 01/82925A1 relates to aromatic compounds of the formula

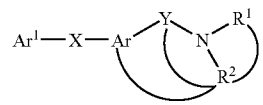

Wherein $Ar^1$ is an optionally substituted cyclic group, X is a spacer having a main chain of 1 to 6 carbon atoms, Y is a bond or spacer having a main chain of 1 to 6 carbon atoms, Ar is a monocyclic aromatic ring which may be condensed with a 4 to 8 membered non-aromatic ring, and may have further substituents; $R^1$ and $R^2$ are independently hydrogen or a hydrocarbon group which may have substituents; $R^1$ and $R^2$ together with the adjacent nitrogen atom may form a nitrogen containing ring which may have substituents; $R^2$ may form a spiro ring together with Ar; or $R^2$ together with the adjacent nitrogen atom may form a nitrogen containing hetero ring which may have substituents; or a salt thereof, which compounds are antagonists of a melanin concentrating hormone suggested as being useful for preventing or treating obesity.

PCT application WO 01/21577A2 (Takeda) relates to aromatic compounds of the formula

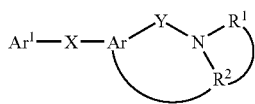

or a salt thereof, which is useful as an agent for preventing or treating obesity; wherein the variables are as disclosed therein.

PCT application WO 03/035624 discloses a compound of formula (I)

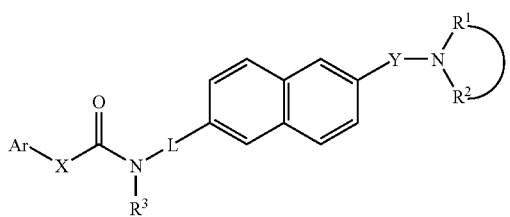

wherein A represents an optionally substituted cyclic group; X represents a bond or a spacer having a C1-6 main chain, R1 and R2 are the same or different and each represents hydrogen or an optionally substituted hydrocarbon group (excluding CO); R3 represents hydrogen or an optionally substituted hydrocarbon group; and ring A and ring B each may have other substituent(s), and when ring B has another substituent, then this substituent may be bonded to R1 to form a ring; a salt of the compound; or a prodrug of any of these having antagonistic activity against melanin concentrating hormone and hence useful as an obesity preventive/remedy, etc.

PCT application WO95/32967 describes compounds of the formula

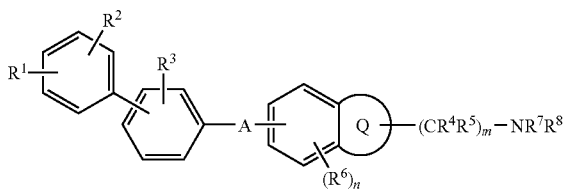

wherein A is CONR, in which R is hydrogen or $C_{1-6}$ alkyl; Q is an optionally substituted 5 to 7 membered heterocyclic ring containing 1 to 3 heteroatoms selected from oxygen, nitrogen, or sulfur; R4 is hydrogen, halogen, etc; R2 and R3 are independently hydrogen, halogen, etc.; R4 and R5 are independently hydrogen or C1-6 alkyl; R6 is halogen, hydroxy, etc.; R7 and R8 are independently hydrogen; C1-6 alkyls, etc.; m is 0 to 4; n is 0.1 or 2; or its salt' which has 5HT1D antagonist activity and can be expected to ameliorate anorexia.

PCT application 03/015769A1 relates to aminoalkyl-substituted aromatic compounds of the formula

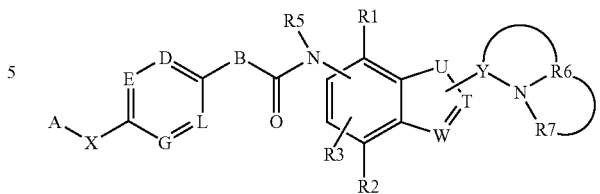

useful as anorexic drugs wherein the variables of the above formula are as described therein.

Current treatments targeted at obesity have side effects. Examples of such treatments include effective over-the-counter appetite suppressants. These agents have not been proven effective for all patients and for sustainable periods of time. Similarly, the approved treatments, sibutramine (Meridia™) and orlistat (Xenical™) have been associated with side effects which may compromise compliance and may preclude long term use for sustained weight loss for certain patient populations.

Therefore, there is a need for new and/or improved therapeutically effective agents useful as antagonists of melanocortin releasing hormone to better control the dietary habits, minimize the preponderance of obesity and treat, prevent and/or ameliorate the effects of obesity including for example diabetes.

SUMMARY OF INVENTION

The present invention relates to a compound of formula I

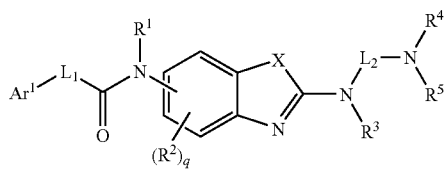

wherein:
X is O, or S;
q is 0 or 1 for $R^2$ other than hydrogen;
$Ar^1$ is a cyclic group optionally substituted with one to four groups independently selected from $C_1$-$C_8$ alkyl, $C_2$-$C_4$ alkenyl, $C_2$-$C_4$ alkynyl, hydroxy, $C_1$-$C_8$ alkoxy, phenyl, aryl, —O-aryl, —O-heteroaryl, —O-heterocyclic, heteroaryl, cycloalkyl, $C_1$-$C_4$ alkylaryl, $C_1$-$C_4$ alkylheteroaryl, $C_1$-$C_4$ alkyl-O-aryl, $C_1$-$C_4$ alkyl-O-heteroaryl, $C_1$-$C_4$ alkyl-O-heterocyclic, $C_1$-$C_4$ alkylcycloalkyl, cyano, —$(CH_2)_n NR^6 R^{6'}$, $C_1$-$C_4$ haloalkyl, $C_1$-$C_4$ haloalkoxy, halo, $(CH_2)_n COR^6$ $(CH_2)_n NR^6 SO_2 R^{6'}$, —$(CH_2)_n C(O)NR^6 R^{6'}$, heterocyclic, and $C_1$-$C_4$ alkylheterocyclic; wherein the cycloalkyl, phenyl, aryl, heteroaryl and heterocyclic substituent are each optionally substituted with one to three groups independently selected from hydroxy, $C_1$-$C_6$ alkoxy, $C_1$-$C_4$ alkoxyalkyl, $C_1$-$C_4$ haloalkoxy, $C_1$-$C_4$ alkyl, halo, $C_1$-$C_4$ haloalkyl, nitro, cyano, amino, carboxamido, phenyl, aryl, alkylheterocyclic, heterocyclic, and oxo;
$L_1$ is a bond, or a divalent linker selected from $C_1$-$C_6$ alkyl, $C_2$-$C_6$ alkenyl, and —$OC_1$-$C_6$ alkyl;
$R^1$ is selected from hydrogen, $C_1$-$C_4$ alkyl and $C_1$-$C_4$ alkylcycloalkyl;

$R^2$ is independently selected from hydrogen, halo, $C_1$-$C_4$ haloalyl, $C_1$-$C_4$ alkyl, and $C_1$-$C_4$ alkoxy;

$R^3$ is selected from the group consisting of hydrogen, $C_1$-$C_6$ alkyl, $C_2$-$C_6$ alkenyl, $C_3$-$C_8$ cycloalkyl, aryl, $C_1$-$C_4$ alkylaryl, $C_1$-$C_4$ alkylcycloalkyl, heterocyclic and $C_1$-$C_4$ alkylheterocyclic; and wherein $R^3$ and $L_2$ may combine together and with the nitrogen atom to which they are attached to form a 5 to 7-member nitrogen-containing non-aromatic heterocycle optionally containing one to three substituents independently selected from oxo, hydroxy, cyano, $C_1$-$C_4$ alkyl, $C_2$-$C_4$ alkenyl, $C_3$-$C_8$ cycloalkyl, $C_1$-$C_4$ alkylaryl, $C_1$-$C_4$ alkylcycloalkyl, $C_1$-$C_4$ alkylheterocyclic, halo, $C_0$-$C_4$ alkylNR$^6$R$^{6'}$, $(CH_2)_n NSO_2 C_1$-$C_4$ alkyl, $(CH_2)_n NSO_2$-phenyl, $(CH_2)_n NSO_2$aryl, $-C(O)C_1$-$C_4$ alkyl, and $-C(O)OC_1$-$C_4$alkyl;

$L_2$ is a divalent linker selected from the group consisting of $C_2$-$C_4$ alkyl, phenyl, aryl, $C_2$-$C_3$ alkylaryl, heterocyclic, heteroaryl, $C_2$-$C_3$ alkylheteroaryl and $C_2$-$C_3$ alkylheterocyclic;

each $R^4$ and $R^5$ is independently selected from the group consisting of hydrogen, $C_1$-$C_8$ alkyl, $C_2$-$C_8$ alkenyl, $C_3$-$C_8$ cycloalkyl, aryl, heteroaryl, $C_1$-$C_4$ alkylaryl, $C_1$-$C_4$ alkylbeteroaryl, $C_1$-$C_4$ alkylcycloalkyl, $(CH_2)_n C(O)C_1$-$C_4$ alkyl, CONR$^6$R$^{6'}$, SO$_2$R$^6$, heterocyclic, and $C_1$-$C_4$ alkylheterocyclic; wherein each of the alkyl, alkenyl, cycloalkyl, aryl, or heterocyclic groups or subgroups is optionally substituted with one to three groups independently selected from $C_1$-$C_8$ alkyl, $C_2$-$C_8$ alkenyl, phenyl, $C_1$-$C_8$ haloalkyl, halo, hydroxy, $-OC_1$-$C_8$ haloalkyl, and alkylaryl; and wherein $R^4$ and $R^5$ optionally combine together and with the nitrogen atom to which they are attached to form a 5 to 7-member optionally substituted nitrogen-containing heterocycle; or one or both of $R^4$ and $R^5$ optionally combine with $L_2$ at a position α, β, γ, or δ to the nitrogen atom of NR$^4$R$^5$ to form a 5 to 7-member nitrogen-containing heterocycle, each nitrogen-containing heterocycle optionally having one to three substituents independently selected from oxo, hydroxy, cyano, $C_1$-$C_4$ alkyl, $C_2$-$C_4$ alkenyl, $C_3$-$C_8$ cycloalkyl, $C_1$-$C_4$ alkylcycloalkyl, halo, $(CH_2)_n NSO_2 C_1$-$C_4$ alkyl, $(CH_2)_n NSO_2$phenyl, $-C(O)C_1$-$C_4$ alkyl, or $-C(O)OC_1$-$C_4$ alkyl and $C_0$-$C_4$ alkylNR$^6$R$^{6'}$;

$R^6$ and $R^{6'}$ are independently selected from the group consisting of hydrogen, $C_1$-$C_4$ alkyl, phenyl, aryl, $C_1$-$C_4$ alkylaryl, or $C_1$-$C_4$ alkylcycloalkyl; or $R^6$ and $R^{6'}$ combine to form an optionally substituted nitrogen containing 5-7 member heterocycle;

m is an integer from 1 to 4; and n is an integer from 0 to 4; or a pharmaceutically acceptable salt, solvate, enantiomer, diastereomer or mixture of or diastereomers thereof.

The present invention also relates to pharmaceutical compositions comprising a compound of formula I.

In another embodiment, the pharmaceutical composition of the present invention may be adapted for use in treating obesity and related diseases.

The present invention also relates to methods for treating, preventing or ameliorating obesity in a patient in need thereof, wherein the treatment, prevention or amelioration comprises administering to said patient a therapeutically effective amount of a compound of formula I.

The present invention also relates to methods for treating, preventing or ameliorating obesity in a patient in need thereof, wherein the treatment, prevention or amelioration comprises administering to said patient a therapeutically effective amount of a compound of formula I in association with a carrier, diluent, and/or other pharmaceutically acceptable excipients.

The present invention also relates to a method for antagonizing the binding of MCH to MCH receptors for the treatment of diseases caused, or exacerbated by melanin concentrating hormone.

The present invention provides the use of a compound of formula I for treating, preventing or ameliorating weight gain leading to obesity.

The present invention provides the use of a compound of formula I as an appetite suppressant and/or as a weight loss agent.

The present invention is related to the use of a compound of formula I for the manufacture of a medicament for treating obesity and related diseases.

DETAILED DESCRIPTION

For the purposes of the present invention, as disclosed and/or claimed herein, the following terms are defined below.

Generally, one of skill in the art is aware that valency must be conserved (complete) for all stable molecules. Therefore, the necessary implication that hydrogen atoms are necessary and available to complete valency in all structures including formula I, unless expressly indicated otherwise, is imputed to the general knowledge of one of skill in the art.

General chemical terms used in the description of compounds herein described bear their usual meanings. For example, the term "$C_{1-8}$ alkyl," or "$(C_1-C_8)$alkyl" or "$C_1-C_8$ alkyl" or as indicated refers to a straight or branched aliphatic chain of 1 to 8 carbon atoms including but not limited to methyl, ethyl, propyl, iso-propyl, n-butyl, pentyl, and the like as indicated. Unless otherwise stated, the term "alkyl" means $C_1$-$C_8$ alkyl. Similarly, the term "$C_0$-$C_8$ alkyl" implies an alkyl group as indicated wherein when the term $C_0$ applies, the alkyl group is not present, and the remaining groups attach directly to the substrate. For example, the group $-C_0$-$C_8$ alkylCONR$^{10}$R$^{11}$ implies that when $C_0$ applies, the group $-C_0$-$C_8$ alkylCONR$^{10}$R$^{11}$ becomes to $-$CONR$^{10}$R$^{11}$.

The invention also contemplates that the term $C_1$-$C_6$ alkyl or $C_2$-$C_6$ alkenyl or similar terms encompass the specified alkyl or alkenyl or similar group, which may be chiral, regio or steroisomeric. Such chiral or regio or stereoisomeric groups are also objects of the present invention.

The terms "cycloalkyl" or "$C_3$-$C_8$ cycloalkyl" as used herein refer to a cyclic hydrocarbon radicals or groups having from 3 to 8 carbon atoms and having no double bonds. Examples of $C_3$-$C_8$ cycloalkyl groups include but are not limited to cyclopropyl, cyclobutyl, cyclopentyl, cyclohexyl, cycloheptyl, cyclooctyl.

The term "$C_3$-$C_8$ cycloalkenyl" as used herein refers to a cyclic hydrocarbon radical or group having from 3 to 8 carbon atoms and having from 1 to 3 double bonds. Specific examples of $C_{3-8}$ cycloalkenyl include cyclopropenyl, cyclobutenyl, cyclopentenyl, cyclohexenyl, cycloheptenyl, and cyclooctenyl.

The term "halo" means halogens including iodo, chloro, bromo and fluoro.

The term "$C_1$-$C_4$ haloalkyl" or the like refers to a $C_1$-$C_4$ alkyl group substituted with one, two or three halogen atoms as possible and appropriate. Examples of $C_1$-$C_4$ haloalkyl include but are not limited to trifluoromethyl, chloroethyl, and 2-chloropropyl. Similarly, a "$C_1$-$C_8$ haloalkyl" group is a $C_1$-$C_8$ alkyl moiety substituted with up to six halo atoms, and more preferably one to three halo atoms.

A "$C_1$-$C_8$ alkoxy" group is a $C_1$-$C_8$ alkyl moiety connected through an oxy linkage. Concrete examples of alkoxy groups include but is not limited to methoxy, ethoxy, propoxy, isopropoxy, butoxy, isobutoxy, sec-butoxy, pentyloxy, and hexyloxy.

The terms "$C_1$-$C_8$ haloalkoxy", "$C_1$-$C_8$ haloalkyloxy", "halogenated $C_1$-$C_8$ alkoxy" and the like mean an alkoxy group having halogen substituent at one or more carbon atoms of the group. The term encompasses groups including for example, difluoromethoxy, trifluoromethoxy, 2-haloethoxy, 2,2,2-trifluoroethoxy, 4,4,4-trifluorobutoxy, up to and including groups having the indicated carbon atoms.

The term "cyclic" as used herein refers to substituted or unsubstituted aromatic and non-aromatic, carbocyclic or heterocyclic ring structure. Cyclic groups may also be monocyclic or bicyclic unless otherwise specified. Aromatic groups include for example, phenyl, thiophene, furan, pyrrole, imidazole, pyrazole, thiazole, isothiazole, oxazole, isoxazole, pyridine, pyrimidine, pyrazine, pyrimidine, pyridazine, napthyl, 1,2,4-oxadiazole, 1,3,4-oxadiazole, 1,2,4,-thiadiazole, 1,3,4-thiadiazole, pyrrolidine, imidazoline, imidazolidine, pyrazoline, pyrazolidine, tetrahydrotbiazole, tetrahydroisothiazole, tetrahydrooxazole, tetrahydroisoxazole, piperidine, tetrahydropyridine, dihydropyridine, piperazine, morpholine, thiomorpholine, tetrahydropyrimidine, tetrahydropyridazine, and hexamethyleneimine. Examples of bicyclic groups within the ambit of cyclic groups as used herein include benzofuran, benzimidazole, benzoxazole, benzisoxazole, benzothiophene, benzothiazole, benzisothiazole, naphthyl, isoquinoline, quinoline, and indolyl, each of which may be optionally substituted. Optional substituents on the cyclic groups include one to three groups independently selected from hydroxy, $C_1$-$C_8$ alkoxyalkyl, $C_1$-$C_8$ haloalkoxy, $C_1$-$C_8$ alkyl, halo, $C_1$-$C_8$ haloalkyl, nitro, cyano, amino, mono or di alkylamine, carboxamido, phenyl, aryl, alkylheterocyclic, heterocyclic, and oxo.

The term "non-aromatic heterocycle" is known to one of skill in the art and/or can be ascertained with minimal inquiry by consulting standard reference texts or literature references pertaining to the skill of organic chemistry and synthesis. Examples of standard reference text are disclosed herein.

The term "alkylcycloalkyl" as used herein refers to an alkyl group on which a cycloalkyl group is substituted. Exemplary of alkylcycloalkyl groups are methylcyclopropyl, methylcyclohexyl, methylcycloheptyl, ethylcyclopropyl, etc. The alkylcycloaliyl group may optionally be substituted with one to five groups independently selected from $C_1$-$C_8$ alkyl, phenyl, aryl, halo, amino, alkysulfonyl, alkylsulfonamide, haloalkyl, carboxyalkyl, carboxamide, alkoxy, and perfluoroalkoxy.

The term "optionally substituted" as used herein and unless otherwise specified, means an optional substitution of one to five, preferably one to two groups independently selected from halo, hydroxy, oxo, cyano, amino, alkylamino, nitro, phenyl, benzyl, aryl, -Oaryl, triazolyl, tetrazolyl, 4,5-dihydrothiazolyl, $C_1$-$C_6$ alkyl, $C_1$-$C_4$ haloalkyl, —$(CH_2)_n NR^6R^{6'}$, $C_1$-$C_8$ haloalkyl, $C_1$-$C_8$ haloalkoxy, halo, $(CH_2)_n COR^6$, $(CH_2)_n NR^6SO_2R^{6'}$, —$(CH_2)_n C(O)NR^6R^{6'}$, heterocyclic, and $C_1$-$C_8$ alkylheterocyclic on the subject group, subgroup, or substituent.

The term "heterocycle" or "heterocyclic" represents a stable, saturated, partially unsaturated, fully unsaturated, or aromatic 4, 5, 6 or 7 membered (or as indicated) ring, said ring having from one to three heteroatoms that are independently selected from the group consisting of sulfur, oxygen, and nitrogen. The heterocycle may be attached at any point which affords a stable structure. Representative heterocycles include 1,3-dioxolane, 4,5-dihydro-1H-imidazole, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine, pyrrole, pyrrolidine, tetrazole, thiadiazole, thiazole, thiophene and triazole.

The heterocyclic group according to the present invention unless otherwise specified is further optionally substituted with one to three, preferably one or two groups independently selected from halo, hydroxy, oxo, cyano, nitro, phenyl, benzyl, triazolyl, tetrazolyl, 4,5-dihydrothiazolyl, $C_1$-$C_6$ alkyl, $C_1$-$C_4$ haloalkyl, $C_1$-$C_6$ alkoxy, $COR^7$, $CONR^7R^7$, $CO_2R^7$, $NR^7R^7$, $NR^7COR^7$, $NR^7SO_2R^8$, $OCOR^8$, $OCO_2R^7$, $OCONR^7R^7$, $SR^7$, $SOR^8$, $SO_2R^7$ and $SO_2(NR^7R^7)$, where $R^7$ is independently at each occurrence H, $C_1$-$C_6$ alkyl, phenyl or benzyl and $R^8$ is independently at each occurrence $C_1$-$C_6$ alkyl, phenyl or benzyl.

The term "oxo" as used herein implies an oxygen atom attached to a carbon atom which is part of a ring or a chain to form a carbonyl group.

The term "alkylheterocyclic" as used herein refers to an alkyl group further substituted with a heterocyclic group. Examples of alkylheterocyclic include but are not limited to 2-methylimidazoline, N-methylmorpholinyl, N-methylpyrrolyl and 2-methylindolyl.

The term "nitrogen containing heterocyclic" means a heterocyclic ring having at least one nitrogen and include heterocyclic groups optionally having in addition to a nitrogen atom one or more of oxygen and sulfur atoms.

The term "basic group" refers to an organic radical which is a proton acceptor. The term "basic group" also refers to an organic group containing one or more basic radicals. Illustrative basic radicals are amidino, guanidino, amino, piperidyl, pyridyl, etc, and excludes amides.

The term "suitable solvent" refers to any solvent, or mixture of solvents, inert to the ongoing reaction, that sufficiently solubilizes the reactants to afford a medium within which to effect the desired reaction.

As used herein, the term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in an aquaculture. Also included are exotic animals used in food production such as alligators, water buffalo and ratites (e.g., emu, rheas or ostriches). The preferred patient of treatment is a human.

The terms "treating" and "treat", as used herein, include their generally accepted meanings, e.g., preventing, prohibiting, restraining, alleviating, ameliorating, slowing, stopping, or reversing the progression or severity of a pathological condition, or sequela thereof.

The terms "preventing", "prevention of", "prophylaxis", "prophylactic" and "prevent" are used herein interchangeably and refer to reducing the likelihood that the recipient of a compound of formula I will incur or develop any of the pathological conditions, or sequela thereof, described herein.

As used herein, the term "effective amount" means an amount of a compound of formula I that is sufficient for treating or preventing a condition, or detrimental effects thereof herein described, or an amount of a compound of formula I that is sufficient for antagonizing the MCHR1 receptor to achieve the objectives of the invention.

The term "pharmaceutically acceptable" is used herein as an adjective and means substantially non-deleterious to the recipient patient.

The term "formulation", as in pharmaceutical formulation, is intended to encompass a product comprising the active ingredient(s) (compound(s) of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier, or a compound of formula I and a pharmaceutically acceptable co-antagonist of MCHR1 useful for the treatment and/or prevention of obesity or a related disease where antagonism of a MCH receptor may be beneficial.

The terms "diseases related to obesity" or "related diseases" as used herein refers to such symptoms, diseases or conditions caused by, exacerbated by, induced by, or adjunct to the condition of being obese. Such diseases, conditions and/or symptoms include but are not limited to eating disorders (bulima, anorexia nervosa, etc.), diabetes, diabetic complications, diabetic retinopathy, sexual/reproductive disorders, depression, anxiety and other stress related disorders, such as for example, post-traumatic stress disorder, substance abuse including alcohol abuse, and nonpharmacological addictions such as gambling, sex, internet, etc. Obesity related diseases also include epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinenamia.

The term "unit dosage form" refers to physically discrete units suitable as unitary dosages for human subjects and other non-human animals (as described above), each unit containing a predetermined quantity of active material calculated to produce the desired therapeutic effect, in association with a suitable pharmaceutical carrier.

Certain compounds of the invention contain an acidic moiety (e.g., carboxy). Therefore, certain compounds of formula I may exist as a pharmaceutical base addition salt. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like.

Certain compounds of the invention contain a basic moiety (e.g., amino). Therefore, certain compounds of formula I may also exist as a pharmaceutical acid addition salt.

Pharmaceutically acceptable salts and common methodology for preparing them are well known to one of skill in the art. See, e.g. P. Stahl, et al. Handbook of Pharmaceutical Salts: Properties, Selections and Use (VCHA/Wiley-VCH, 200); S. M. Berge, et al., "Pharmaceutical Salts" Journal of Pharmaceutical Sciences, Vol. 66, No. 1, January 1977.

PREFERRED COMPOUNDS OF THE INVENTION

Certain compounds of the invention are particularly interesting and preferred. The following listing sets out several groups of preferred compounds. It will be understood that each of the listings may be combined with other listings to create additional groups of preferred compounds.

Preferred $Ar^1$ Groups

Preferred $Ar^1$ groups are selected from phenyl, thiopheneyl, thiazolyl, isothiazolyl, furanyl, pyrazinyl, pyridinyl, pyrimidyl, indolyl, naphthyl, benzthiazolyl, benztriazolyl, benzimidazolyl, benzothiophenyl, benzofuranyl, each optionally substituted with $C_1$-$C_6$ alkyl, $C_1$-$C_6$ cycloalkyl, $C_1$-$C_6$ haloalkyl, hydroxy, alkoxyalkyl, cyano, halo, phenyl, aryl, heteroaryl, heterocycle, carboxamide, and $C_1$-$C_6$ carboxyalkyl. More preferred $Ar^1$ groups include optionally substituted phenyl, napthyl, thiopheneyl, pyrazinyl, pyridinyl, benztriazolyl, benzimidazolyl, and indolyl. Particularly preferred $Ar^1$ groups are phenyl, thiopheneyl, or pyrazinyl substituted with 1-3 groups independently selected from substituted phenyl, aryl, heteroaryl, and heterocycle.

Preferred $L_1$ Groups

Preferred as $L_1$ is a bond or a divalent linker selected from $C_1$-$C_4$ alkyl, $C_2$-$C_4$ alkenyl, or —O$C_1$-$C_4$ alkyl. Particularly preferred is $L_1$ as a bond or —OC—$C_2$ alkyl.

Preferred $L^2$ Groups

Preferred are $L^2$ groups selected from the group consisting of —$CH_2CH_2$—, —$CH_2CH_2CH_2$—, optionally substituted aryl or heterocyclic including isooxazolyl, oxazolyl, phenyl, pyrazinyl, pyrimidinyl, pyridinyl, pyridazinyl, and piperidinyl. Most preferred is an $L_2$ group selected from —$CH_2CH_2$—, and —$CH_2CH_2CH_2$—.

Preferred $R^1$ $R^1$ is preferably independently selected from the group consisting hydrogen, $C_1$-$C_8$ alkyl, $C_1$-$C_4$ haloalkyl, and $C_1$-$C_4$ alkylcycloalkyl. Most preferably, $R^1$ is hydrogen.

Preferred $R^2$ $R^2$ is preferably independently selected from the group consisting hydrogen, halo, hydroxy, $C_1$-$C_4$ haloalkyl, $C_1$-$C_8$ alkyl, $C_2$-$C_4$ alkenyl, $C_1$-$C_4$ alkoxy, and $C_1$-$C_4$ alkylcycloalkyl. Most preferably, each $R^2$ is independently, hydrogen, $C_1$-$C_3$ alkyl, or $C_1$-$C_4$ alkoxy. Also most preferably, q is 0, or 1.

Preferred $R^3$ Groups $R^3$ is preferably selected from the group consisting of hydrogen, $C_1$-$C_6$ alkyl, $C_2$-$C_6$ alkenyl, $C_3$-$C_8$ cycloalkyl, $C_3$-$C_8$ alkylcycloalkyl, phenyl, benzyl, heterocyclic, and $C_1$-$C_4$ alkylheterocyclic. More preferably, $R^3$ is selected from the group consisting of hydrogen, $C_1$-$C_6$ alkyl, and $C_1$-$C_3$ alkylcycloalkyl.

Also preferred are $R^3$ and $L^2$ groups which combine with each other, and with the nitrogen atom to which they are attached to form an optionally substituted nitrogen-containing non-aromatic heterocycle selected from 2-pyrroline, pyrrolidine, imidazoline, imidazolidine, pyrazoline, piperazinyl, piperidinyl, and pyrimidinyl. Most preferred is a compound wherein $R^3$ and $L^2$ combine to form an optionally substituted pyrrolidinyl.

Preferred $R^4$ and $R^5$ Groups:

Preferred $R^4$ and $R^5$ are independently selected from hydrogen, $C_1$-$C_8$ alkyl, $C_2$-$C_8$ alkenyl, $C_2$-$C_8$ alkynyl, phenyl, aryl, $C_1$-$C_8$ alkylaryl, $(CH_2)_n NR^6 SO_2 R^{6'}$, $(CH_2)_n C(O)R^6$, $(CH_2)_n CONR^6 R^{6'}$ and $(CH_2)_n C(O)OR^6$; wherein the alkyl, alkenyl, phenyl, and aryl groups are optionally substituted with one to three substituents independently selected from oxo, nitro, cyano, $C_1$-$C_8$ alkyl, aryl, halo, hydroxy, $C_1$-$C_8$ alkoxy, $C_1$-$C_8$ haloalkyl, $(CH_2)_n C(O)R^6$, $(CH_2)_n CONR^6 R^{6'}$ and $(CH_2)_n C(O)OR^6$; and wherein n is 0 or 1.

Also preferred $R^4$ and $R^5$ substituents are independently selected from hydrogen, $C_1$-$C_8$ alkyl, $C_2$-$C_8$ alkenyl, phenyl, acetyl, and isoquinolylinyl.

Also preferred is a compound wherein one or both of $R^4$ and $R^5$ combine with L at a position α, β, γ or δ, to the nitrogen atom to form a 5 to 7 member nitrogen containing heterocyclic group.

Preferred $R^6$ and $R^{6'}$ Groups

A preferred $R^6$ or $R^{6'}$ is independently selected from hydrogen, $C_1$-$C_8$ alkyl, phenyl, aryl, alkylaryl, and $C_3$-$C_8$ cycloalkyl Also preferred is a compound of formula I wherein $Ar^1$ is phenyl, pyrazinyl, pyridinyl or thiopheneyl; $L_1$ is a bond, or CH=CH; $R^1$ and $R^2$ are both hydrogen; $R^3$ is hydrogen or methyl; $L_2$ is a bond, ethyl, propyl; or $L_2$ combines with $R^3$ to form an optionally substituted 5-7 member ring non-aromatic heterocycle; or with one or both of $R^4$ or $R^5$ to form an optionally substituted 5-7 member ring heterocycle or $R^4$ and $R^5$ are independently selected from methyl, ethyl, isopropyl, acetyl, or $R^4$ and $R^5$ combine to form an optionally substituted nitrogen containing heterocycle selected from isoquinolinyl, quinolinyl, pyrrolidinyl, morpholinyl, pyrazinyl, piperazinyl, and piperidinyl.

Most preferred is a compound of the invention selected from the group consisting of: 4'-Fluoro-biphenyl-4-carboxylic acid {2-[(2-dimethylamino-ethyl)-methyl-amino]-benzothiazol-6-yl}-amide, 4'-Fluoro-biphenyl-4-carboxylic acid {2-[methyl-(1-methyl-piperidin-4-yl)-amino]-benzothiazol-6-yl}-amide, 4'-Fluoro-biphenyl-4-carboxylic acid {2-[methyl-(1-methyl-pyrrolidin-3-yl)-amino]-benzothiazol-6-yl}-amide, 2'-Methyl-biphenyl-4-carboxylic acid {2-[(2-dimethylamino-ethyl)-methyl-amino]-benzothiazol-6-yl}-amide, 4'-Fluoro-biphenyl-4-carboxylic acid {2-[methyl-(1-methyl-pyrrolidin-3-ylmethyl)-amino]-benzothiazol-6-yl}-amide, 4'-Fluoro-biphenyl-4-carboxylic acid {2-[(3-diethylamino-propyl)-methyl-amino]-benzothiazol-6-yl}-amide, 4-Cyclohexyl-N-{2-[(2-dimethylamino-ethyl)-methyl-amino]-benzothiazol-6-yl}-benzamide, 2',4'-Difluoro-biphenyl-4-carboxylic acid {2-[(2-dimethylamino-ethyl)-methyl-amino]-benzothiazol-6-yl}-amide, 2'-Chloro-biphenyl-4-carboxylic acid {2-[(2-dimethylamino-ethyl)-methyl-amino]-benzothiazol-6-yl}-amide, 4'-Fluoro-2'-methyl-biphenyl-4-carboxylic acid {2-[(2-dimethylamino-ethyl)-methyl-amino]-benzothiazol-6-yl}-amide, 2',3'-Dichloro-biphenyl-4-carboxylic acid {2-[(2-dimethylamino-ethyl)-methyl-amino]-benzothiazol-6-yl}-amide, 4'-Fluoro-biphenyl-4-carboxylic acid [2-(methyl-pyrrolidin-3-ylmethyl-amino)-benzothiazol-6-yl]-amide, 4'-Fluoro-biphenyl-4-carboxylic acid {2-[(1-isopropyl-pyrrolidin-3-ylmethyl)methyl-amino]-benzothiazol-6-yl}-amide, 4'-Fluoro-biphenyl-4-carboxylic acid {2-[(1-ethyl-pyrrolidin-3-ylmethyl)-methyl-amino]-benzothiazol-6-yl}-amide, 4'-Fluoro-biphenyl-4-carboxylic acid {2-[methyl-(2-pyrrolidin-1-yl-ethyl-amino]-benzothiazol-6-yl}-amide, 2'-Chloro-4'-trifluoromethyl-biphenyl-4-carboxylic acid {2-[(2-dimethylamino-ethyl)-methyl-amino]-benzothiazol-6-yl}-amide, 4-Cyclohexyl-N-{2-[methyl-(1-methyl-pyrrolidin-3-ylmethyl)-amino]-benzooxazol-5-yl}-benzamide, 4'-Fluoro-biphenyl-4-carboxylic acid (2-[methyl-(1-methyl-piperidin-3-yl)-amino]-benzooxazol-5-yl)-amide, 4'-Fluoro-biphenyl-4-carboxylic acid {2-[methyl-(2-piperidin-1-yl-ethyl)-amino]-benzothiazol-6-yl}-amide, 4-Cyclohexyl-N-{2-[(2-dimethylamino-ethyl)-methyl-amino]-benzooxazol-5-yl}-benzamide, N-{2-[Methyl-(1-methyl-pyrrolidin-3-ylmethyl)-amino]-benzooxazol-5-yl}-4-phenoxy-benzamide, 4'-Fluoro-biphenyl-4-carboxylic acid {2-[(3-diethylamino-propyl)-methyl-amino]-benzooxazol-5-yl}-amide, 4-Cyclohexyl-N-{2-[(3-dimethylamino-propyl)-methyl-amino]-benzooxazol-5-yl}-benzamide, 6-(4-Fluoro-phenyl)-N-{2-[methyl-(1-methyl-pyrrolidin-3-ylmethyl)-amino]-benzooxazol-5-yl}-nicotinamide, 4-Cyclohexyl-N-{2-[methyl-(1-methyl-piperidin-4-yl)-amino]-benzooxazol-5-yl}-benzamide, N-{2-[Methyl-(1-methyl-piperidin-4-yl)-amino]-benzooxazol-5-yl}-3-phenoxy-benzamide, 2'-Chloro-4'-methoxy-biphenyl-4-carboxylic acid {2-[methyl-(1-methyl-pyrrolidin-3-yl)-amino]-benzothiazol-6-yl}-amide, 4-Cyclohexyloxy-N-{2-[(2-dimethylamino-ethyl)-methyl-amino]-benzothiazol-6-yl}-benzamide, 4-Cyclohexylmethoxy-N-{2-[(2-dimethylamino-ethyl)-methyl-amino]-benzothiazol-6-yl}-benzamide, 4-Butyl-N-{2-[(2-dimethylamino-ethyl)-methyl-amino]-benzooxazol-5-yl}-benzamide, 4-Cyclohexyloxy-N-{2-[(2-dimethylamino-ethyl)-methyl-amino]-benzooxazol-5-yl}-benzamide, N-{2-[(2-Dimethylamino-ethyl)-methyl-amino]-benzooxazol-5-yl}-6-(4-fluoro-phenyl)-nicotinamide, 6-(4-Fluoro-phenyl)-N-{2-[methyl-(1-methyl-piperidin-4-yl)-amino]-benzooxazol-5-yl}-nicotinamide, 4-Cyclohexylmethoxy-N-{2-[methyl-(1-methyl-pyrrolidin-3-yl)-amino]-benzothiazol-6-yl}-benzamide, 2'-Chloro-4'-trifluoromethoxy-biphenyl-4-carboxylic acid {2-[(2-dimethylamino-ethyl)-methyl-amino]-benzothiazol-6-yl}-amide, 2'4'-Dimethyl-biphenyl-4-carboxylic acid {2-[(2-dimethylamino-ethyl)-methyl-amino]-denzothiazol-6-yl}-amide, N-{2-[(2-Dimethylamino-ethyl)-methyl-amino]-benzooxazol-5-yl}-4-phenoxy-benzamide, Biphenyl-4-carboxylic acid {2-[(2-dimethylamino-ethyl)-methyl-amino]-benzooxazol-5-yl}-amide, 4-Cyclohexylmethoxy-N-{2-[(2-dimethylamino-ethyl)-methyl-amino]-benzooxazol-5-yl}-benzamide, 5-(4-Fluoro-phenyl)pyrazine-2-carboxylic acid {2-[(2-dimethylamino-ethyl)-methyl-amino]-benzooxazol-5-yl}-amide, 4'-Fluoro-biphenyl-4-carboxylic acid {2-[methyl-(2-morpholin-4-yl-ethyl)-amino]-benzooxazol-5-yl}-amide, N-{2-[(2-Dimethylamino-ethyl)-methyl-amino]-benzooxazol-5-yl}-4-isobutoxy-benzamide, 4'-Fluoro-biphenyl-4-carboxylic acid {2-[methyl-(4-methyl-morpholin-2-ylmethyl)-amino]-benzooxazol-5-yl}-amide, 5-(4-Fluoro-phenyl)-pyrazine-2-carboxylic acid {2-[methyl-(1-methyl-piperidin-4-yl)-amino]-benzooxazol-5-yl}-amide, 4'-Chloro-2'-methyl-biphenyl-4-carboxylic acid {2-[methyl-(1-methyl-piperidin-4-yl)-amino]-benzooxazol-5-yl}-amide, 5-Phenyl-thiophene-2-carboxylic acid {2-[methyl-(1-methyl-piperidin-4-yl)-amino]-benzooxazol-5-yl}-amide, 4'-Fluoro-biphenyl-4-carboxylic acid {2-[methyl-(1-methyl-pyrrolidin-3-ylmethyl)-amino]-benzooxazol-5-yl}-amide, 2',4'-dichloro-biphenyl-4-carboxylic Acid {2-[methyl-(1-methyl-pyrrolidin-3-ylmethyl)-amino]-benzooxazol-5-yl}-amide, 4'-Fluoro-biphenyl-carboxylic acid {2-[(2-dimethylamino-ethyl)-methyl-amino]-benzooxazol-5-yl}-amide,
4'-Fluoro-biphenyl-4-carboxylic acid {2-[methyl-(1-methyl-piperidin-4-yl)-amino]-benzooxazol-5-yl}-amide,
4-Butyl-N-{2-[methyl-(1-methyl-piperidin-4-yl)-amino]-benzooxazol-5-yl}-benzamide,
Biphenyl-4-carboxylic acid {2-[methyl-(1-methyl-piperidin-4-yl)-amino]-benzooxazol-5-yl}-amide,
4'-Fluoro-biphenyl-4-carboxylic acid {2-[methyl-(2-pyrrolidin-1-yl-ethyl)-amino]-benzooxazol-5-yl}-amide,
2',4'-Dichloro-biphenyl-4-carboxylic acid {2-[(2-dimethylamino-ethyl)-methyl-amino]-benzooxazol-5-yl}-amide,
2'-Chloro-4'-methyl-biphenyl-4-carboxylic acid {2-[(2-dimethylamino-ethyl)-methyl-amino]-benzooxazol-5-yl}-amide,
4'-Chloro-2'-methyl-biphenyl-4-carboxylic acid {2-[(2-dimethylamino-ethyl)-methyl-amino]-benzooxazol-5-yl}-amide,
Biphenyl-4-carboxylic acid {2-[methyl-(1-methyl-piperidin-3-yl)-amino]-benzooxazol-5-yl}-amide,
4'-Fluoro-biphenyl-4-carboxylic acid {2-[methyl-(1-methyl-piperidin-3-yl)-amino]-benzooxazol-5-yl}-amide,
2'-Chloro-4'-methyl-biphenyl-4-carboxylic acid {2-[methyl-(1-methyl-piperidin-4-yl)-amino]-benzooxazol-5-yl}-amide,
2'-Chloro-4'-fluoro-biphenyl-4-carboxylic acid {2-[methyl-(1-methyl-piperidin-4-yl)-amino]-benzooxazol-5-yl}-amide,
2',4'-Dichloro-biphenyl-4-carboxylic acid {2-[methyl-(1-methyl-piperidin-4-yl)-amino]-benzooxazol-5-yl}-amide,
2',4'-Difluoro-biphenyl-4-carboxylic acid {2-[methyl-(1-methyl-piperidin-4-yl)-amino]-benzooxazol-5-yl}-amide,
3-(4-Fluoro-phenyl)-N-{2-[methyl-(1-methyl-pyrrolidin-3-ylmethyl)-amino]-benzothiazol-6-yl}-acrylamide,
2'-Chloro-4'-methoxy-biphenyl-4-carboxylic acid {2-[(2-dimethylamino-ethyl)-methyl-amino]-benzothiazol-6-yl}-amide,
2'-Chloro-4'-fluoro-biphenyl-4-carboxylic acid {2-[(2-dimethylamino-ethyl)-methyl-amino]-benzothiazol-6-yl}-amide,
2',4'-Dichloro-biphenyl-4-carboxylic acid {2-[(2-dimethylamino-ethyl)-methyl-amino]-benzothiazol-6-yl}-amide,
4'-Chloro-2'-methyl-biphenyl-4-carboxylic acid {2-[(2-dimethylamino-ethyl)-methyl-amino]-benzothiazol-6-yl}-amide,
2'-Chloro-4'-methyl-biphenyl-4-carboxylic acid {2-[(2-dimethylamino-ethyl)-methyl-amino]-benzothiazol-6-yl}-amide,
5-(2,4-Difluoro-phenyl)-thiophene-2-carboxylic acid {2-[methyl-(1-methyl-piperidin-4-yl)-amino]-benzooxazol-5-yl}-amide,
5-(4-Fluoro-phenyl)-thiophene-2-carboxylic acid {2-[methyl-(1-methyl-piperidin-4-yl)-amino]-benzooxazol-5-yl}-amide,
5-(3,4-Difluoro-phenyl)-thiophene-2-carboxylic acid {2-[methyl-1-methyl-piperidin-4-yl)amino]-benzooxazol-5-yl}-amide,
5-(4-Chloro-phenyl)-thiophene-2-carboxylic acid {2-[methyl-(1-methyl-piperidin-4-yl)-amino]-benzooxazol-5-yl}-amide,
5-p-Tolyl-thiophene-2-carboxylic acid {2-[methyl-(1-methyl-piperidin-4-yl)-amino]-benzooxazol-5-yl}-amide,
5-(4-Methoxy-phenyl)-thiophene-2-carboxylic acid {2-[methyl-(1-methyl-piperidin-4-yl)-amino]-benzooxazol-5-yl}-amide,
[2,3']Bithiophenyl-5-carboxylic acid {2-[methyl-(1-methyl-piperidin-4-yl)-amino]-benzooxazol-5-yl}-amide,
5-(3-Chloro-phenyl)-thiophene-2-carboxylic acid {2-[methyl-(1-methyl-piperidin-4-yl)-amino]-benzooxazol-5-yl}-amide,
5-Benzo[1,3]dioxol-5-yl-thiophene-2-carboxylic acid {2-[methyl-(1-methyl-piperidin-4-yl)-amino]-benzooxazol-5-yl}-amide, and
5'-Chloro-[2,2']bithiophenyl-5-carboxylic acid {2-[methyl-(1-methyl-piperidin-4-yl)-amino]-benzooxazol-5-yl}-amide, or a pharmaceutically acceptable salt, solvate, enantiomer, diastereomer and mixture of diastereomers thereof.

PREPARING COMPOUNDS OF THE INVENTION

The anti-obesity benzthiazoles of formula (I, X=S) are prepared by methods well known to those skilled in the art of organic synthesis from starting compounds also known to those skilled in the art. The explanation below is deemed helpful to those skilled in the art who desire to prepare the compounds of the present invention. Preferred methods include, but are not limited to those methods described below.

SCHEME 1 sets forth a general method used in the present invention to prepare substituted benzthiazoles of formula (I, X=S).

SCHEME 1

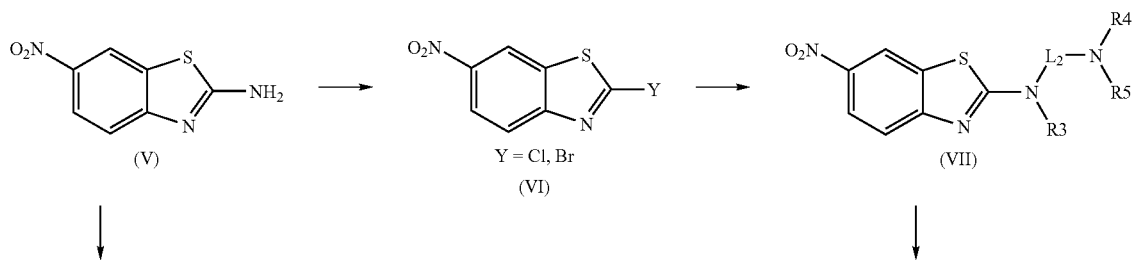

-continued

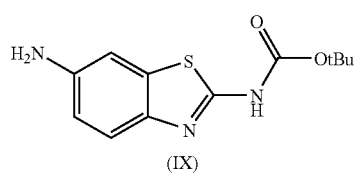

(IX)

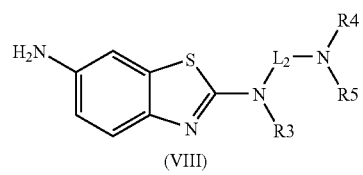

(VIII)

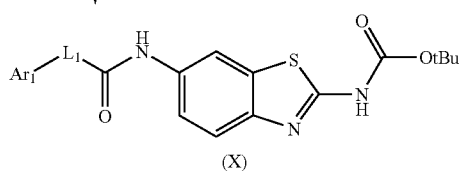

(X)

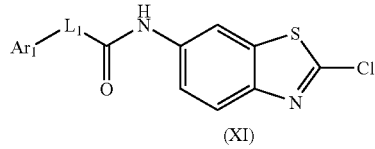

(XI)

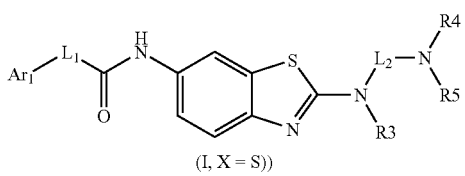

(I, X = S))

Commercially available 2-amino-6-nitrobenzthiazole (V) is readily converted to 2-chloro- or 2-bromo-6-nitrobenzthiazole (VI) by the well known Sandmeyer reaction. Diazotization may be accomplished with tert-butyl nitrite in acetonitrile followed by treatment with copper (II) chloride or copper (II) bromide. The reaction may be conducted from room temperature up to the boiling point of the acetonitrile. Preferably, the reaction mixture is heated to about 65° C. for from 1 to 16 hours as needed to ensure completion of the reaction. While the reaction and its derivations are well known to those skilled in the art, additional references and guidance may be obtained from "March's Advanced Organic Chemistry", Wiley-Interscience Publishers, 2001, p. 935.

Treatment of 2-halo-6-nitrobenzthiazole (VI) with a commercially available or easily preprared amine of formula H—N($R^3$)-$L_2$-N($R^4$)($R^5$) affords substituted benzthiazoles (VII). Optimal conditions include performing the reaction in an inert solvent, for example tetrahydrofuran, at temperatures ranging from room temperature up to the boiling point of the solvent. More preferred is to conduct the substitution reaction at room temperature for a period of time ranging from 1 to 16 hours as needed to ensure completion of the reaction.

Formation of 6-aminobenzthiazoles (VIII) is accomplished via reduction of the corresponding nitro compounds (VII). A vast array of methods are well known to those skilled in the art or the reader may consult the text of R. C. Larock in "Comprehensive Organic Transformations", VCH Publishers, 1989, p. 411. Preferred is reduction via hydrogenation ($H_2$) with palladium (Pd, 5% on carbon) catalyst in ethanol at atmospheric pressure or elevated pressure as needed to ensure complete reduction. In a few instances, it was preferable to add $K_2CO_3$ and perform the reaction in tetrahydrofuran and water at a temperature up to 40 C.

The amine (VIII) is reacted with an appropriately substituted amide forming agent of the formula $Ar^1$-$L_1$-C(=O)—$X^2$ to produce the target anti-obesity agents of formula I (X=S) by nitrogen-acylation conditions. $X^2$ of the amide forming agent comprises —OH (carboxylic acid) or halide (acyl halide), preferably chlorine, or a suitable group to provide a mixed anhydride. The nitrogen-acylation of primary amines to produce secondary amides is one of the oldest known reactions, and nitrogen acylation conditions are abundantly known to those skilled in the art and may be found in R. C. Larock in Comprehensive Organic Transformations, VCH Publishers, 1989, p. 972, 979, and 981.

An alternative preparation of target compounds (1, X=S) can proceed via the intermediacy of protected amine (IX). It is preferred that the N-protecting group be t-butoxycarbonyl (BOC) or benzyloxycarbonyl (CBZ). It is more preferred that the protecting group be t-butoxycarbonyl. One skilled in the art will understand the preferred methods of introducing a t-butoxycarbonyl or benzyloxycarbonyl protecting group and may additionally consult T. W. Green and P. G. M. Wuts in "Protective Groups in Organic Chemistry", Wiley-Interscience Publishers, 1991 for guidance.

Amide formation to afford (X) proceeds as described above. The protected intermediate (X) is nitrogen-deprotected to the corresponding amine by means known to those skilled in the art for removal of amine protecting group. Suitable means for removal of the amine protecting group depends on the nature of the protecting group. Those skilled in the art, knowing the nature of a specific protecting group, know which reagent is preferable for its removal. For example, it is preferred to remove the protecting group, BOC, by dissolving the protected amine (X) in a trifluoroacetic acid/dichloromethane (1/1) mixture. When complete, the solvents are removed under reduced pressure to give the corresponding amine (as the corresponding salt, i.e. trifluoroacetic acid salt) which is preferably used without further purification. However, if desired, the amine can be purified further by means well known to those skilled in the art, such as for example, recrystallization. Further, the non-salt form may be obtained, for example, by preparing the free base amine via treatment of the salt with mild basic conditions. Additional BOC deprotection conditions and deprotection conditions for other protecting groups can be found in T. W. Green and P. G. M. Wuts in "Protective Groups in Organic Chemistry", Wiley-Interscience Publishers, 1991, p. 309. A Sandmeyer reaction (see above) affords the 2-chlorobenzothiazole (XI) and amine substitution (see above) affords the desired targets (I, X═S).

SCHEME 2 and SCHEME 3 demonstrate the flexibility of this chemistry.

SCHEME 2

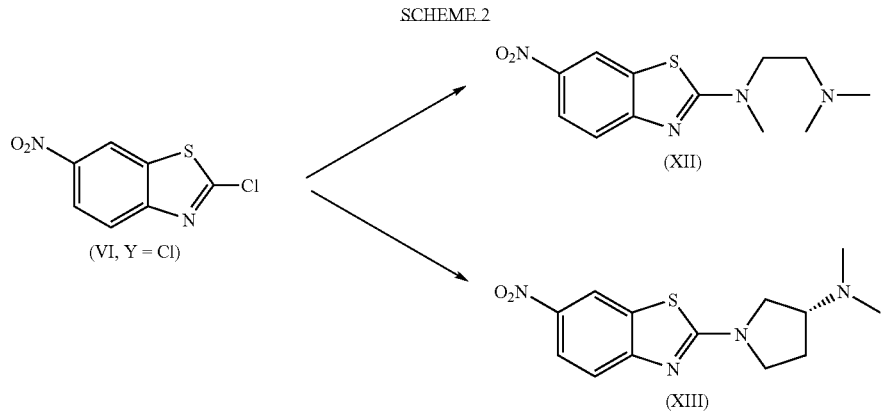

As referenced above, treatment of 2-chloro-6-nitrobenzthiazole (VI, Y═Cl) with a commercially available or easily prepared amine of formula H—N(R$^3$)-L$_2$-N(R$^4$)(R$^5$) such as, for example, N,N,N'-trimethylethyldiamine (Aldrich Chemical Co.) or (3R)-(+)-3-(dimethylamino) pyrrolidine (TCI America Inc.), affords, respectively, the substituted benzthiazoles (XII) and (XIII). The respectively reduced amines (XIV) and (XV) may be acylated per the well-understood conditions of this invention with a commercially available amide forming reagent of the formula Ar$^1$-L$_1$-C(═O)—X$^2$ such as, for example, trans-4-(4-trifluoromethyl) cinnamic acid (Aldrich Chemical Co.) or 4-(4-fluorophenyl)benzoic acid (Array Biopharma Inc.,), wherein X$^2$═OH, to generate the target benzthiazoles such as for example, the target compounds shown including compound (XVI).

SCHEME 3

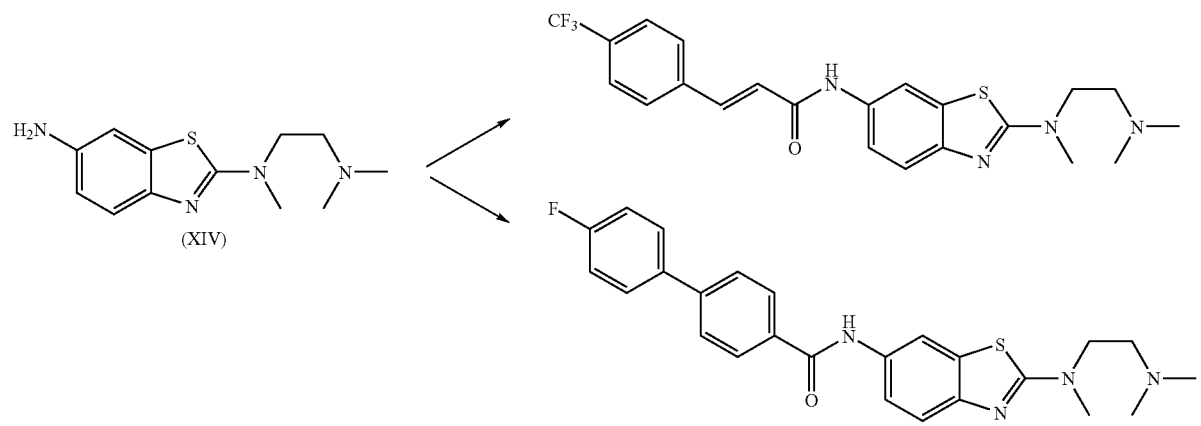

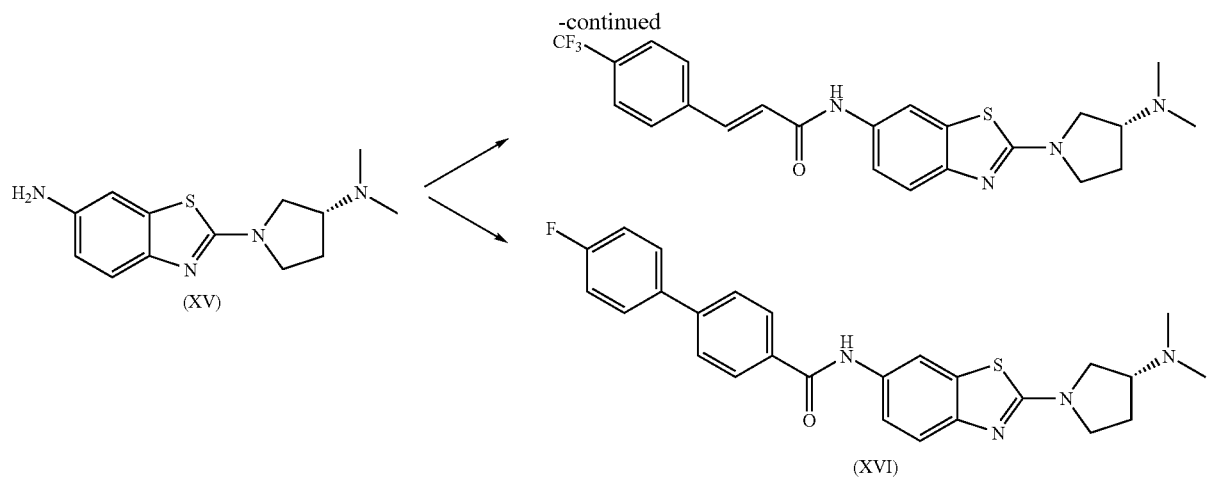

Benzoxazole compounds (I, X=O) of the present invention may be prepared following the procedures of SCHEME 4 below or by using variations of SCHEME 4 or other methods well known to those skilled in the art of organic synthesis.

Subsequent treatment with a commercially available amine of formula H—N(R$^2$)-L$_2$-N(R$^3$)(R$^4$) affords substituted benzoxazoles (XIX). Optimal conditions include performing the reaction in an inert solvent, for example toluene,

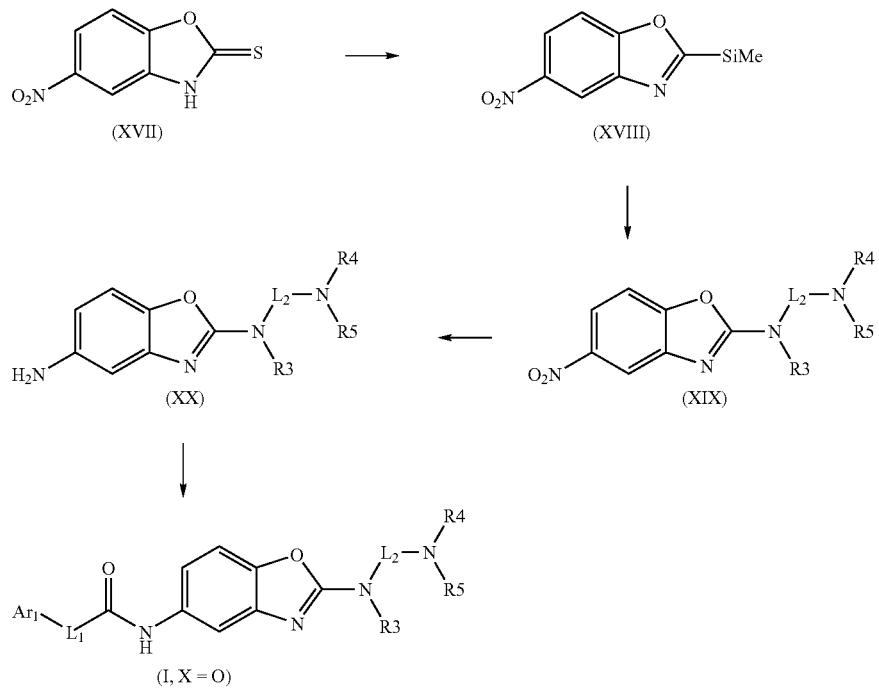

SCHEME 4 sets forth a general method used to prepare substituted benzoxazoles of formula (I, X=O). Commercially available 2-amino-4-nitrophenol is cyclized to the thione (XVII) by precedent established by R. Lok, et al. (Journal of Organic Chemistry, 1996, 61(10), 3289-3297). Activation of the 2-position to a suitable leaving group may be accomplished via formation of the thiomethyl ether by treatment of thione (XVII) with an acceptable base (preferred is sodium hydride) and quenching with methyl iodide.

at temperatures ranging from room temperature up to the boiling point of the solvent. More preferred is to conduct the substitution reaction at about 70° C. for about 10-20 hours or until the reaction is complete.

Formation of 5-aminobenzoxazoles (XX) is accomplished via reduction of the corresponding nitro compounds. A vast array of methods are well known to those skilled in the art or the reader may consult the text of R. C. Larock in "Comprehensive Organic Transformations", VCH Publishers, 1989, p.

411. Preferred is reduction via hydrogenation (H₂) with palladium (Pd, 5% on carbon) catalyst in ethanol at atmospheric pressure or elevated pressure as needed to ensure complete reduction. Alternatively the reduction may be accomplished using Pd(OH)₂ in the presence of cyclohexene in refluxing ethanol, a procedure or known variations thereof that can readily be ascertained and/or performed by one of skill in the art.

The amine (XX) is reacted with an appropriately substituted amide forming agent of the formula Ar¹-L₁-C(=O)—X² to produce the target anti-obesity agents of formula (I, X=O) by nitrogen-acylation conditions. X² of the amide forming agent comprises —H (carboxylic acid) or halide (acyl halide), preferably chlorine, or a suitable group to provide a mixed anhydride. The nitrogen-acylation of primary amines to produce secondary amides is one of the oldest known reactions, and nitrogen acylation conditions are abundantly known to those skilled in the art and can be found in R. C. Larock in Comprehensive Organic Transformations, VCH Publishers, 1989, p. 972, 979, and 981. For example, amide coupling reagents, such as O-(7-azabenzo-triazol-1-yl)-N,N,N',N'-tetramethyluronium hexafluorophosphate (HATU) and O-(benzotriazol-1-yl)-N,N, N',N'-tetramethyluronium tetrafluoroborate (TBTU) may by used to form amides from primary amines and carboxylic acids by one of ordinary skill in the art. Alternatively the amine (XX) is reacted with an ester of formula Ar¹-L₁-(=O)—X² wherein X² comprises —OMe or —OEt. The acylation with the ester may be accomplished with Al(Me)₃ (about 3 equivalents) in an inert solvent, such as dichloromethane.

SCHEME 5 further demonstrates the flexibility of this chemistry.

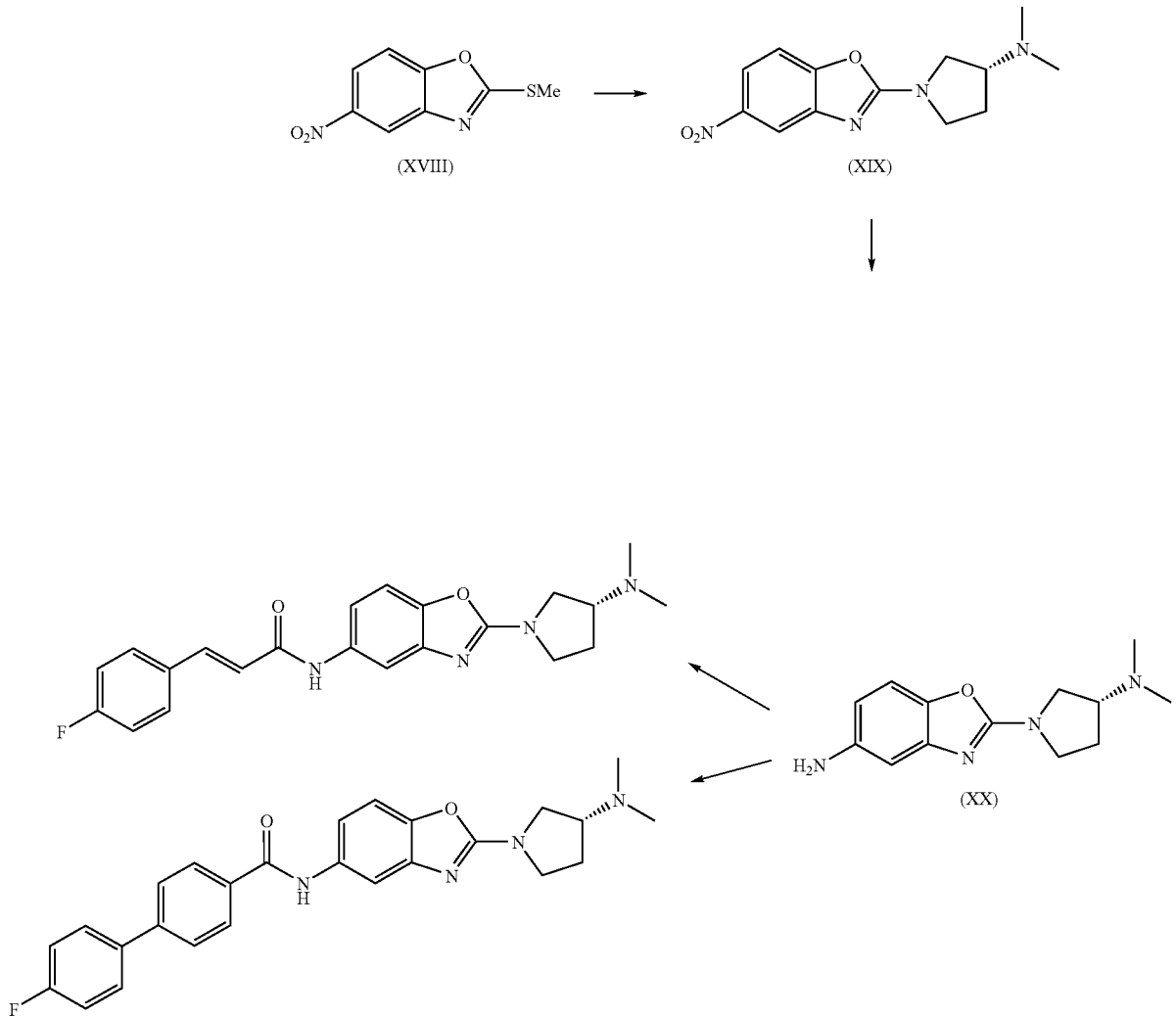

As referenced above, treatment of 5-nitro-2-thiomethyl-benzoxazole with a commercially available amine of formula H—N(R³)-L₂-N(R⁴)(R⁵) such as, for example, (3R)-(+)-3-(dimethylamino) pyrrolidine (TCI America), affords the substituted benzthiazoles (XIX). The subsequently reduced amine (XX) may be acylated per the well-understood conditions of this invention with a commercially available amide forming reagent of the formula Ar¹-L₁-C(=O)—X² such as, for example, trans-4-(trifluoromethyl) cinnamic acid (Aldrich Chemical) or 4-(4-fluorophenyl)benzoic acid (Array Biopharma), wherein X²=OH, to generate the target benzthiazoles such as for example, the target compounds shown.

SCHEME 6 demonstrates the ability to introduce the substituent R⁵ as the last step in the reaction sequence. Compound XI (SCHEME 1) may be treated with a commercially available amine of formula H—N(R³)-L₂-N(R⁴)(PG), wherein R⁵ is a protecting group, to afford substituted benzthiazoles (XXI). Deprotection to afford (XXII) and acetylation yields the desired compounds (XXIII). Optimal conditions for the reactions set forth in SCHEME 6 are described as above for SCHEMES 1-5.

2 min was repeated 30 times, followed by a final elongation step at 72° C. for 10 min. The desired PCR product (1.1 Kb) was confirmed by agarose gel electrophoresis and the band was extracted from the gel by Geneclean (Bio101) following the manufacturer's instructions. Following extraction, the cDNA fragment was cloned into pCR2.1-TOPO plasmid (Invitrogen Corp) to confirm the identity and sequence.

In order to generate cell lines stably expressing MCHR1, the insert was then subcloned into the Xba I and Not I sites of pcDNA(+)-3.1-neomycin (Invitrogen). After purification by Qiagen Maxi-prep kit (QIAGEN, Inc.), the plasmid was transfected by Fugene 6 (Roche Applied Science) into AV12 cells that had been previously transfected with the promiscuous G protein $G_{\alpha15}$. The transfected cells were selected by G418 (800 µg/ml) for 10-14 days and single colonies were isolated from culture plates. The G418-resistant colonies were further selected for MCHR1 expression by measuring MCH-stimulated $Ca^{2+}$ transients with a fluorometric imaging plate reader (FLIPR, Molecular Devices).

Typically, individual clones are plated out in 96-well plates at 60,000 cells per well in 100 µl of growth medium (Dulbec-

SCHEME 6

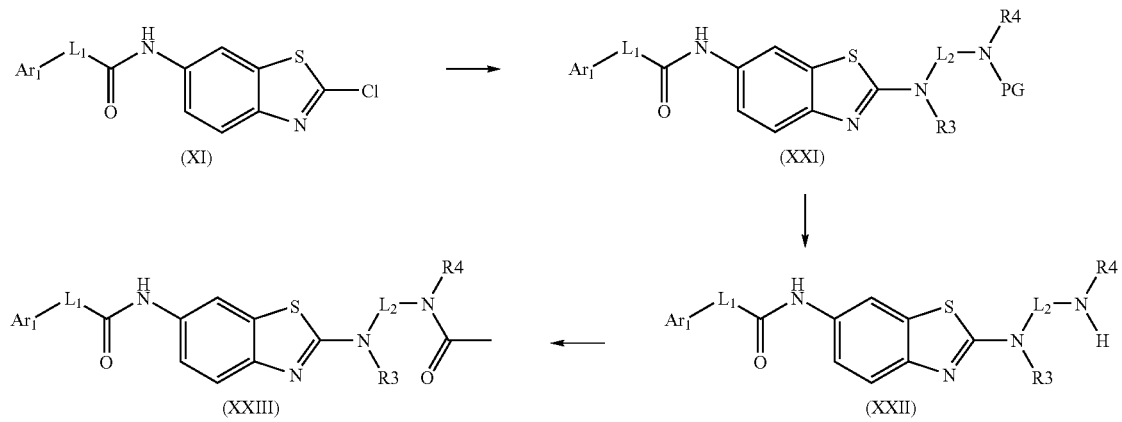

Demonstration of Function

In order to demonstrate that compounds of the present invention have the capacity to bind to and inhibit the function of MCHR1, binding and functional assays were established. All ligands, radioligands, solvents and reagents employed in these assays are readily available from commercial sources or can be readily prepared by those skilled in the art.

The full-length cDNA for human MCHR1 was cloned from a human adult brain cDNA library (Edge Biosystems, Cat. 38356) by standard polymerase chain reaction (PCR) methodology employing the following primers: sense, 5'-GCCACCATGGACCT GGAAGCCTCGCTGC-3'; antisense, 5'-TGGTGCCCTGACTTGGAGGTGTGC-3'. The PCR reaction was performed in a final volume of 50 µl containing 5 µl of a 10× stock solution of PCR buffer, 1 µl of 10 mM dNTP mixture (200 µM final), 2 µl of 50 mM Mg(SO₄) (2 mM final), 0.5 µl of 20 µM solutions of each primer (0.2 µM final), 5 µl of template cDNA containing 0.5 ng DNA, 0.5 µl of Platinum Taq High Fidelity DNA polymerase (Gibco Life Technologies) and 36 µl of H₂O. PCR amplification was performed on a Perkin Elmer 9600 thermocycler. After denaturation for 90 sec at 94° C., the amplification sequence consisting of 94° C. for 25 sec, 55° C. for 25 sec and 72° C. for co's modified Eagle's medium (DMEM), 5% fetal bovine serum, 2 mM L-glutamine, 10 mM HEPES, 1 mM sodium pyruvate, 0.5 mg/ml Zeocin, and 0.5 mg/ml Geneticin). After 24 hrs at 37° C., medium is removed and replaced with 50 µl of dye loading buffer (Hank's balanced salt solution (HBSS) containing 25 mM HEPES, 0.04% Pluronate 127 and 8 µM Fluo3 Both from Molecular Probes)). After a 60 min loading period at room temperature, dye loading buffer is aspirated and replaced with 100 µl of HEPES/HBBS. Plate is placed in FLIPR and basal readings are taken for 10 sec, at which point 100 µl of buffer containing 2 µM MCH (1 µM final) is added and measurements are taken over 105 sec. To correct for variations between clones in numbers of cells per well, the MCH response is normalized to the response induced by epinephrine.

Both the $^{125}$I-MCH binding and functional GTPγ$^{35}$S binding assays employed membranes isolated from a clone designated as clone 43. Typically, cells from 20 confluent T225 flasks were processed by washing the monolayers in cold phosphate-buffered saline (PBS), scraping the cells into same and re-suspending the cell pellet in 35 ml of 250 mM Sucrose, 50 mM HEPES, pH 7.5, 1 mM MgCl₂, 24 µg/ml DNase I, and protease inhibitors (1 Complete® tablet, per 50 ml of buffer prepared, Roche Diagnostics). Alternatively, greater levels of cells could be generated by adapting cell growth to suspension culture in 20 L stirred vessel bioreactors. After incubation on ice for 5 min, cells were disrupted with 20-25 strokes of a Teflon/Glass homogenizer attached to an overhead motorized stirrer, and the homogenate was centrifuged at 40,000 rpm in Beckman Type 70.1 Ti rotor. The pellets were re-suspended in 250 mM Sucrose, 50 mM HEPES, pH 7.5, 1.5 mM $CaCl_2$, 1 mM $MgSO_4$ and protease inhibitors by Teflon/Glass homogenization to achieve a protein concentration of ~3-5 mg/ml (Pierce BCA assay with Bovine serum albumin as standard). Aliquots were stored at −70° C.

Binding of compounds to MCHR1 was assessed in a competitive binding assay employing $^{125}$I-MCH, compound and clone 43 membranes. Briefly, assays are carried out in 96-well Costar 3632 white opaque plates in a total volume of 200 µl containing 25 mM HEPES, pH 7.0, 10 mM $CaCl_2$, 2 mg/ml bovine serum albumin, 0.5% dimethyl sulfoxide (DMSO), 5 µg of clone 43 membranes, 200 pM $^{125}$I-MCH (NEN), 0.625 mg/ml of wheat germ agglutinin scintillation proximity assay beads (WGA-SPA beads, Amersham Inc., now GE Healthcare Inc.) and a graded dose of test compound. Non-specific binding is assessed in the presence of 0.1 µM unlabeled MCH. Bound $^{125}$I-MCH is determined by placing sealed plates in a Microbeta Trilux (Perkin Elmer Life and Analytical Sciences Inc) and counting after a 12 hr delay.

$IC_{50}$ values (defined as the concentration of test compound required to reduce specific binding of $^{125}$I-MCH by 50%) are determined by fitting the concentration-response data to a 4-parameter model (max response, min-response, Hill coefficient, $IC_{50}$) using Excel® (Microsoft Corp.). $K_i$ values are calculated from $IC_{50}$ values using the Cheng-Prusoff approximation as described by Cheng et al. (Relationship between the inhibition constant ($K_i$) and the concentration of inhibitor which causes 50% inhibition ($IC_{50}$) of an enzymatic reaction, Biochem. Pharmacol., 22: 3099-3108 (1973)). The $K_d$ for $^{125}$I-MCH is determined independently from a saturation binding isotherm. Exemplified compounds showed a Ki of <1 µM under the binding assay conditions. Specifically, a sample of observed Ki values is provided in Table 1 (below) for demonstration purposes only.

TABLE 1

| Example # | Average MCHR1 Ki (nM) |
|---|---|
| 106 | 16.7 |
| 107 | 15.3 |
| 34 | 8.79 |
| 157 | 7.50 |

Functional antagonism of MCH activity is assessed by measuring the ability of test compound to inhibit MCH-stimulated binding of GTPγ$^{35}$S to clone 43 membranes. Briefly, assays are carried out in Costar 3632 white opaque plates in a total volume of 200 µl containing 50 mM Hepes, pH 7.4, 5 mM $MgCl_2$, 10 µ/ml saponin, 1.0 mg/ml bovine serum albumin, 100 mM NaCl, 3 µM GDP, 0.3 nM GTPγ$^{35}$S, 10 nM MCH (approximately equal to $EC_{90}$), 20 µg of clone 43 membranes, 5.0 mg/ml of wheat germ agglutinin scintillation proximity assay beads (WGA-SPA beads, Amersham Inc., now GE Healthcare Inc.) and a graded dose of test compound. The plates are sealed and left for 16-18 hrs at 4° C. After a 1 hr delay to allow plates to equilibrate to ambient temperature, bound GTPγ$^{35}$S is determined by counting in a Microbeta Trilux (Perkin Elmer Life and Analytical Sciences Inc).

$IC_{50}$ values (defined as the concentration of test compound required to reduce MCH-stimulated GTPγ$^{35}$S binding by 50%) are determined by fitting the concentration-response data to a 4-parameter model (max response, min response, Hill coefficient, $IC_{50}$) using Excel (Microsoft). After verifying competitive antagonism by Schild analysis, Kb values are calculated from the $IC_{50}$ values for each antagonist and the $EC_{50}$ for MCH (determined independently) using a modification of the Cheng-Prusoff approximation as described by Leff and Dougal (Trends Pharmacol. Sci. (1993) 14: 110-112).

Exemplified compounds showed $IC_{50}$ values of <1 µM under the functional assay conditions disclosed herein.

In order to demonstrate in vivo efficacy, compounds of the invention were administered by oral gavage to diet-induced obese male Long-Evans rats (Harlan, Ind.) weighing 500-550 g. Vehicle consisted of 1% CMC and 0.25% PS-80 in water.

Animals were individually housed in a temperature regulated room (24° C.) with a reverse 12 hour light/dark cycle (dark 10:00/22:00). Water and food (Teklad 95217, Harlan, Wis.) were available ad libitum. Compounds were dosed orally once a day before onset of dark for 3 days. Daily food intake and body weight change were measured for the 3 day period. Exemplified compounds tested at 10 mg/kg showed reduction of 3 day cumulative body weight gain when compared with vehicle-treated controls. Specifically, a sample of observed 3 day cumulative body weight reduction, relative to control, is provided in Table 2 (below) for demonstration purposes only.

TABLE 2

| Example # | Body weight reduction @ 10 mg/Kg versus vehicle control. Data expressed in grams. |
|---|---|
| 106 | 8.4 |
| 107 | 7.1 |
| 34 | 5.8 |
| 157 | 18 |

Utility

As antagonists of the MCHR1 binding, a compound of the present invention is useful in treating conditions in human and non-human animals (especially companion animals) in which the MCHR1 receptor has been demonstrated to play a role. The diseases, disorders or conditions for which compounds of the present invention are useful in treating or preventing include, but are not limited to, diabetes mellitus, hyperglycemia, obesity, hyperlipidemia, hypertriglyceridemia, hypercholesterolemia, atherosclerosis of coronary, cerebrovascular and peripheral arteries, gastrointestinal disorders including peptic ulcer, esophagitis, gastritis and duodenitis, (including that induced by H. pylori), intestinal ulcerations (including inflammatory bowel disease, ulcerative colitis, Crohn's disease and proctitis) and gastrointestinal ulcerations, neurogenic inflammation of airways, including cough, asthma, depression, prostate diseases such as benign prostate hyperplasia, irritable bowel syndrome and other disorders needing decreased gut motility, diabetic retinopathy, neuropathic bladder dysfunction, elevated intraocular pressure and glaucoma and non-specific diarrhea dumping syndrome. By inhibiting MCH activity the compounds of the present invention provide anorexic effects. That is, the compounds of the invention are useful as appetite suppressants and/or weightloss agents. The compounds of the invention may also be used for treating and/or preventing anxiety and other stress related disorders, such as post-traumatic stress disorder, substance abuse including alcohol abuse, and nonpharmacological addictions such as gambling, sex, internet, etc. The compounds of the invention may also be used in combination with other approved therapeutic agents for the treatment, prevention and/or amelioration of obesity and related diseases. In this format, the compounds of the present invention enhance the positive effects of such approved combination treatments while minimizing the side effects due to the potential requirement of lower doses of such combination compounds. Such combination therapies may be delivered individually or in a combined formulation. Examples of compounds useful in combination with a compound of formula I include weight loss agents (Meridia™, Xenical™), cholesterol lowering agents (such as for example lovastatin, simvastatin pravastatin, fluvastatin, and atorvastatin), glucose level control or modulating agents, nerve growth factor agonists (such as for example, axokine), cannabinoid CB-1 antagonist compounds (such as for example rimonanbant) and the like.

In treating non-human, non-companion animals, the compounds of the present invention are useful for reducing weight gain and/or improving the feed utilization efficiency and/or increasing lean body mass.

Formulation

A compound of formula I is preferably formulated in a unit dosage form prior to administration. Therefore, yet another embodiment of the present invention is a pharmaceutical formulation comprising a compound of formula I and a pharmaceutical carrier preferably in unit dosage packages, sachets, vials or other presentation/delivery devises known to one of skill in the art.

The present pharmaceutical formulations are prepared by known procedures using well-known and readily available ingredients added to or admixed with the novel compound of formula I. In making the formulations of the present invention, the active ingredient (formula I compound) will usually be mixed with a carrier, or diluted by a carrier, or enclosed within a carrier which may be in the form of a liquid, tablet, capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders. Examples of suitable carriers and procedures for preparing regular and common formulations are known to one of skill in the art and/or available to one of skill in the art upon minimal scientific inquiry.

Dose

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. However, it will be understood that the therapeutic dosage administered will be determined by the physician in the light of the relevant circumstances, or by the veterinarian for non-human recipients.

Generally, an effective minimum daily dose of a compound of formula I is about 20 to 200 mg. Typically, an effective maximum dose is about 200 to 2000 mg. The exact dose may be determined, in accordance with the standard practice in the medical arts of "dose titrating" the recipient; that is, initially administering a low dose of the compound, and gradually increasing the does until the desired therapeutic effect is observed.

Route of Administration

The compounds may be administered by a variety of routes including the oral, rectal, transdermal, subcutaneous, topical, intravenous, intramuscular or intranasal routes. A preferred route of administration is oral.

Combination Therapy

A compound of formula I may be used in combination with other drugs or therapies that are used in the treatment/prevention/suppression or amelioration of the diseases or conditions for which compounds of formula I are useful. Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I. Examples of other active ingredients that (if approved) may be combined with a compound of formula I, either administered separately or in the same pharmaceutical compositions, include, but are not limited to:

insulin sensitizers including (i) PPARγ agonists such as the glitazones (e.g. troglitazone, pioglitazone, englitazone, MCC-555, BRLA9653 and the like), and compounds disclosed in WO97/27857, 97/28115, 97/28137 and 97/27847; (ii) biguanides such as metformin and phenformin;
  (a) insulin or insulin mimetics;
  (b) sulfonylureas such as tolbutamide and glipizide;
  (c) alpha-glucosidase inhibitors (such as acarbose);
  (d) cholesterol lowering agents such as
    i. HMG-CoA reductase inhibitors (lovastatin, simvastatin pravastatin, fluvastatin, atorvastatin, and other statins),
    ii. sequestrants (cholestyramine, colestipol and a dialkylaminoalkyl derivatives of a cross-linked dextran),
    iii. nicotinyl alcohol nicotinic acid or a salt thereof,
    iv. proliferator-activator receptor a agonists such as fenofibric acid derivatives (gemfibrozil, clofibrat, fenofibrate and benzafibrate),
    v. inhibitors of cholesterol absorption for example β-sitosterol and (acyl CoA:cholesterol acyltransferase) inhibitors for example melinamide,
    vi. probucol,
    vii. vitamin E, and
    viii. thyromimetics;
  (f) PPARδ agonists such as those disclosed in WO97/28149;
  (g) Anti obesity compounds such as fenfluramine, dexfenfluramine, phentermine, sibutramine, orlistat, axokine, rimonanbant, etc;
  (h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;
  (i) PPARα agonists such as described in WO 97/36579 by Glaxo;
  (j) PPARγ antagonists as described in WO97/10813; and
  (k) serotonin reuptake inhibitors such as fluoxetine and sertraline
  (l) antipsychotic agents such as for example olanzapine.

EXAMPLES

The following examples are only illustrative of the preparation protocols and applicants' ability to prepare compounds of the present invention based on the schemes presented or known or simple modifications thereof. The examples are not intended to be exclusive or exhaustive of compounds made or obtainable.

Materials and Methods

Solvents and reagents were used as purchased from chemical suppliers and reactions were conducted at ambient atmosphere unless otherwise stated. Reactions were shaken on an orbital shaker block in 40 mL vials. Mass spectrum data was obtained on a Micromass Platform LCZ spectrometer using electrospray (ES) ionization with the following conditions: LC column: Waters XTerra $C_{18}$ 2.1×50 mm 3.5 µm; gradient: 5-100% ACN/MeOH (50/50) w/0.2% $NH_4$Formate in 3.5 to 7.0 min then held at 100% for 1.0 min.; column temp: 50° C.+/−10° C.; AS temp: ambient; flow rate: 1.0 ml/min.

NMR data was obtained on a Varian 400 MHz spectrometer and is reported in ppm. Common abbreviations used throughout the experimental are: O-(7-azabenzo-triazol-1-yl)-N,N, N',N'-tetramethyluronium hexafluorophosphate (HATU), methanol (MeOM), ethanol (EtOH), dichloromethane ($CH_2Cl_2$), diisopropylethyl amine (DIEA). Other abbreviations are known to one of skill in the art or are easily deciphered by one of skill in the art upon minimal inquiry.

Example 1

3-(3-Chloro-4-fluoro-phenyl)-N-[2-(3-dimethylamino-pyrrolidin-1-yl)-benzothiazol-6-yl]-acrylamide

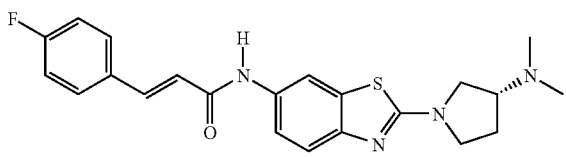

Step 1. 2-Chloro-6-nitro-benzothiazole

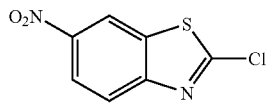

Combine tert-butyl nitrite, (35 mL, 292 mmol, technical 90%) and copper (II) chloride (31.7 g, 236 mmol) in acetonitrile (400 mL) and warm to 65° C. under nitrogen for 1 hour. Slowly add 2-amino-6-nitrobenzthiazole (41.7 g, 214 mmol) over 15 min. Continue to stir at 65° C. for 30 min. Cool to room temperature, dilute with $CH_2Cl_2$, and add 0.1 N HCl to precipitate the product. Filter and dry in a vacuum oven overnight to afford 2-chloro-6-nitrobenzthiazole (35.1 g, 77%). $^1$H NMR (400 MHz, DMSO-$d_6$): δ 9.18 (d, 1H, J=2.2 Hz), 8.37 (dd, 1H, J=9.0, 2.4 Hz), 8.18 (d, 1H, J=8.8 Hz).

Step 2. 2-(3-Dimethylamino-pyrrolidin-1-yl)-benzothiazol-6-ylamine

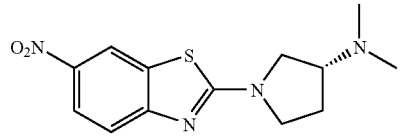

Suspend 2-chloro-6-nitrobenzthiazole (8.49 g, 39.6 mmol) in THF (100 mL). Slowly add (3R)-(+)-3-(dimethylamino) pyrrolidine (5.24 g, 45.9 mmol). Stir the reaction overnight at room temperature. Dilute the reaction with ethyl acetate and then wash with water and brine. Concentrate the organic portion in vacuo, and triturate the resulting residue with MeOH to afford the title compound (4.94 g, 43%). $^1$H NMR (400 MHz, DMSO-$d_6$): δ 8.81 (d, 1H, J=2.2 Hz), 8.14 (dd, 1H, J=9.0, 2.4 Hz), 7.52 (d, 1H, J=8.8 Hz), 4.00-3.43 (m, 3H), 3.30 (m, 1H), 2.91 (m, 1H), 2.20-2.15 (m, 7H), 1.93 (m, 1H).

Step 3. 2-(3-Dimethylamino-pyrrolidin-1-yl)-benzothiazol-6-ylamine

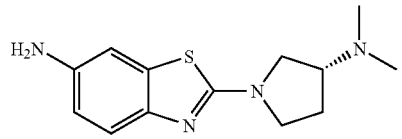

Combine 2-(3-dimethylamino-pyrrolidin-1-yl)-benzothiazol-6-ylamine (12.11 g, 41.4 mmol) and 5% palladium on carbon (12.1 g) in EtOH (500 mL). Shake on a Parr shaker at 60 psi of hydrogen at room temperature for 18 h. Filter the reaction mixture through filter paper and concentrate the filtrate in vacuo to afford the crude title compound (8.50 g, 78%). The crude product was carried on as is. $^1$H NMR (400 MHz, CDCl$_3$): δ 7.39 (d, 1H, J=8.8 Hz), 6.95 (d, 1H, J=2.6 Hz), 6.69 (dd, 1H, J=8.6, 2.4 Hz), 3.83 (dd, 1H, J=9.7, 7.0 Hz), 3.70 (m, 1H), 3.53 (m, 1H), 3.43 (m, 1H), 2.95 (m, 1H), 2.35 (s, 6H), 2.27 (m, 1H), 2.05 (m, 1H).

Step 4. 3-(3-Chloro-4-fluoro-phenyl)-N-[2-(3-dimethylamino-pyrrolidin-1-yl)-benzothiazol-6-yl]-acrylamide

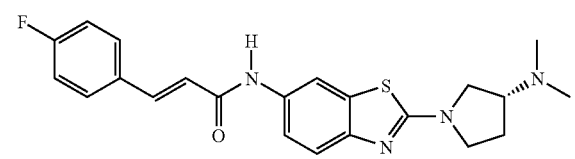

Method A: Combine 4-fluorocinnamic acid (304 mg, 1.83 mmol), HATU (701 mg, 1.84 mmol), and 2-(3-dimethylamino-pyrrolidin-1-yl)benzothiazol-6-ylamine (400 mg, 1.52 mmol) in $CH_2Cl_2$ (8.0 mL). Add DIEA (900 µL, 5.17 mmol) and shake at room temperature overnight. Absorb the reaction mixture on silica gel, and purify using silica gel chromatography, eluting with a gradient of MeOH in $CH_2Cl_2$ (10-20%) to afford the title compound (278 mg, 45%). mass spectrum (m/e): 411.0 [M+H]. $^1$H NMR (400 MHz, DMSO-$d_6$): δ 10.32 (s, 1H), 8.27 (d, 1H, J=2.2 Hz), 7.72-7.65 (m, 2H), 7.57 (d, 1H, J=15.9 Hz), 7.48-7.39 (m, 2H), 7.28 (t, 2H, J=8.8 Hz), 6.83 (d, 1H, J=15.9 Hz), 3.73 (dd, 1H, J=9.7, 7.2 Hz), 3.62 (m, 1H), 3.46 (m, 1H), 3.31 (m, 1H), 2.99 (s, 1H), 2.28-2.22 (m, 7H), 1.94 (m, 1H).

Method B: Weigh out between 1.8 to 2.3 g of diisopropylamine, polymer bound (100-200 mesh, 1% cross linked, Aldrich), in a 40 mL vial. Add 2-(3-dimethylamino-pyrrolidin-1-yl)-benzothiazol-6-ylamine (3.0 mL, 0.618 mmol, from a 0.206 M stock solution), HATU (4.0 mL, 0.804 mmol, from a 0.201 M stock solution), and 4-fluorocinnamic acid (0.107 g, 0.644 mmol) and shake overnight. Filter into a 40 mL vial, rinsing with DMF (25 mL). Add PS—SO$_3$H resin to the filtrate and shake for 1 hour. Filter to remove the solvents, wash the resin with THF/MeOH/THF/MeOH (5 mL each), and transfer the resin into a 40 mL vial. Add 2 N ammonia in ethanol (15 mL) and shake for 1 hour. Filter to remove the resin and concentrate in vacuo. Absorb the crude mixture on silica gel, and purify using silica gel chromatography, eluting with a gradient of 10-20% MeOH in CH$_2$Cl$_2$ to afford the title compound (29 mg, 11%). mass spectrum (m/e): 411.2 [M+H], 409.2 [M−H].

Example 2

N-[2-(3-Dimethylamino-pyrrolidin-1-yl)-benzothiazol-6-yl]-3-p-tolyl-acrylamide

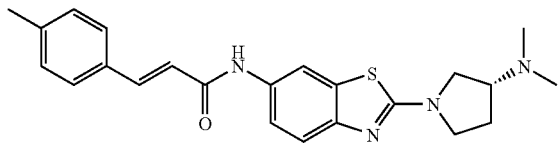

Combine 4-methylcinnamic acid (0.093 g, 0.572 mmol), CH$_2$Cl$_2$ (5.0 mL), and DMF (3 drops) with stirring. Add oxalyl chloride (0.17 mL, 1.91 mmol) and stir the mixture for 2.5 h at room temperature. Concentrate the mixture in vacuo, add hexane (approximately 10 mL), re-concentrate in vacuo, and add CH$_2$Cl$_2$ (4.0 mL). Transfer the mixture to a 40 mL reaction vial and add a solution of 2-(3-dimethylamino-pyrrolidin-1-yl)-benzothiazol-6-ylamine (0.100 g, 0.381 mmol) (example 1, step 3) in CH$_2$Cl$_2$ (5.0 mL). Shake the reaction vial for 1 h at room temperature. Dilute the reaction mixture with CH$_2$Cl$_2$ (25 mL), wash with aqueous 1.0 M NaOH (50 mL), concentrate in vacuo, and purify using silica gel chromatography (12 g column, 10-20% MeOH/CH$_2$Cl$_2$ for 16 min.) to afford the title compound as a yellow solid (96 mg, 62%). mass spectrum (m/e): 407.3 [M+1], 405.2 [M−1]. $^1$H NMR (400 MHz, CDCl$_3$): δ 8.33 (s, 1H), 7.71 (d, 1H, J=15.6 Hz), 7.67 (s, 1H), 7.50 (d, 1H, J=9.2 Hz), 7.39 (d, 2H, J=7.2 Hz), 7.13-7.19 (m, 3H), 6.51 (d, 1H, J=15.6 Hz), 3.82 (t, 1H, J=8.0 Hz), 3.71 (t, 1H, J=9.2 Hz), 3.53 (m, 1H), 3.39 (t, 1H, J=8.0 Hz), 2.89 (m, 1H), 2.36 (s, 3H), 2.30 (s, 6H), 2.25 (m, 1H), 1.99 (m, 1H).

Example 3

3-(3-Chloro-phenyl)-N-[2-(3-dimethylamino-pyrrolidin-1-yl)-benzothiazol-6-yl]-acrylamide

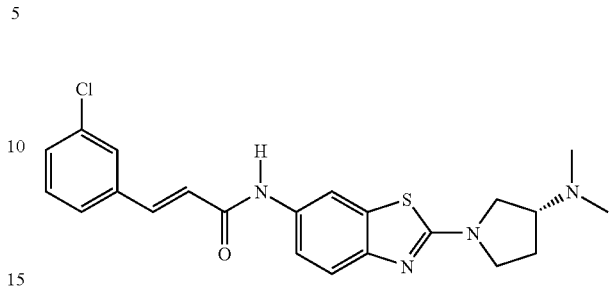

Combine 3-chlorocinnamic acid (0.104 g, 0.572 mmol), CH$_2$Cl$_2$ (13 mL), and DMF (3 drops) with stirring. Add oxalyl chloride (0.17 mL, 1.91 mmol) and stir the mixture for 2.5 h at room temperature. Concentrate the mixture in vacuo, add hexane (approximately 10 mL), re-concentrate in vacuo, and add CH$_2$Cl$_2$ (4.0 mL). Transfer the mixture to a 40 mL reaction vial and add a mixture of 2-(3-dimethylamino-pyrrolidin-1-yl)-benzothiazol-6-ylamine (0.100 g, 0.381 mmol) (Example 1, step 3) in CH$_2$Cl$_2$ (5.0 mL). Shake the reaction vial for 1 h at room temperature. Dilute the reaction mixture with CH$_2$Cl$_2$ (25 mL), wash with 1.0 M NaOH (aqueous) (4×25 mL), dry over sodium sulfate, filter, and concentrate in vacuo. Purify the residue using silica gel chromatography (12 g column, 10-20% MeOH(CH$_2$Cl$_2$) to afford the title compound as a yellow solid (80 mg, 49%). mass spectrum (m/e): 427.2 [M+1], 425.2 [M−1]. $^1$H NMR (400 MHz, CDCl$_3$ (spiked with CD$_3$OD)): δ 8.28 (s, 1H), 7.61 (d, 1H, J=15.6 Hz), 7.47-7.43 (m, 2H), 7.32 (d, 1H, J=7.2 Hz), 7.30-7.23 (m, 2H), 7.19 (dd, 1H, J=8.8, 2.0 Hz), 6.57 (d, 1H, J=15.6 Hz), 3.78 (t, 1H, J=8.8 Hz), 3.68 (t, 1H, J=10.0 Hz), 3.50 (m, 1H), 3.36 (t, 1H, J=9.2 Hz), 2.88 (m, 1H), 2.29 (s, 6H), 2.23 (m, 1H), 1.97 (m, 1H).

Example 4

3-(3,4-Dichloro-phenyl)-N-[2-(3-dimethylamino-pyrrolidin-1-yl)-benzothiazol-6-yl]-acrylamide

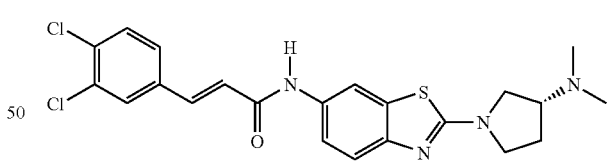

Combine 3,4-dichlorocinnamic acid (0.083 g, 0.381 mmol), CH$_2$Cl$_2$ (5.0 mL), and DMF (3 drops) with stirring. Add oxalyl chloride (0.10 mL, 1.14 mmol) and stir the mixture for 3 h at room temperature. Concentrate the mixture in vacuo, add hexane (approximately 10 mL), re-concentrate in vacuo, and add CH$_2$Cl$_2$ (5.0 mL). Transfer the mixture to a 40 mL reaction vial and add a mixture of 2-(3-dimethylamino-pyrrolidin-1-yl)-benzothiazol-6-ylamine (0.100 g, 0.381 mmol) (Example 1, step 3) in CH$_2$Cl$_2$ (5.0 mL). Shake the reaction vial overnight at room temperature. Dilute the reaction mixture with CH$_2$Cl$_2$ (30 mL), wash with saturated NaHCO$_3$ (aqueous) (2×25 mL), dry over sodium sulfate, filter, and concentrate in vacuo. Purify the residue using silica gel chromatography (12 g column, 5-15% MeOH/CH$_2$Cl$_2$ over 45 min) to yield a yellow residue. Dilute the residue with CH$_2$Cl$_2$ (25 mL) and wash with 1 M NaOH (25 mL). Filter a yellow solid which precipitates in the separatory funnel. Concentrate the mother liquor in vacuo and filter, washing with cold CH$_2$Cl$_2$ to obtain a second crop. Combine the precipitate from the separatory funnel, and the second crop, to afford the title compound (57 mg, 32%). mass spectrum (m/e): 461.2 [M+1], 459.2 [M−1]. $^1$H NMR (400 MHz, CDCl$_3$): δ8.31 (d, 1H, J=1.6 Hz), 7.65 (d, 1H, J=15.6 Hz), 7.64 (m, 1H), 7.52 (d, 1H, J=8.4 Hz), 7.46 (d, 1H, J=8.4 Hz), 7.37 (m, 1H), 7.35 (m, 1H), 7.16 (dd, 1H, J=8.8, 2.4 Hz), 6.53 (d, 1H, J=15.6 Hz), 3.86 (t, 1H, J=9.2 Hz), 3.74 (t, 1H, J=9.2 Hz), 3.56 (m, 1H), 3.50-3.42 (m, 1H), 2.98 (m, 1H), 2.36 (s, 6H), 2.29 (m, 1H), 2.07 (m, 1H).

Example 5

3-(3-Chloro-4-fluoro-phenyl)-N-[2-(3-dimethylamino-pyrrolidin-1-yl)-benzothiazol-6-yl]-acrylamide

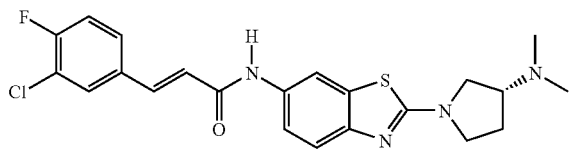

Combine 3-chloro-4-fluorocinnamic acid (0.0765 g, 0.381 mmol), CH$_2$Cl$_2$ (5.0 mL), and DMF (3 drops) with stirring. Add oxalyl chloride (0.10 mL, 1.14 mmol) and stir the mixture for 3 b at room temperature. Concentrate the mixture in vacuo, add hexane (approximately 10 mL), re-concentrate in vacuo, and add CH$_2$Cl$_2$ (5.0 mL). Transfer the mixture to a 40 mL reaction vial and add a mixture of 2-(3-dimethylamino-pyrrolidin-1-yl)-benzothiazol-6-ylamine (0.100 g, 0.381 mmol) (Example 1, step 3) in CH$_2$Cl$_2$ (5.0 mL). Shake the reaction vial overnight at room temperature. Dilute the reaction mixture with CH$_2$Cl$_2$ (25 mL), wash with saturated NaHCO$_3$ (aqueous) (2×25 mL), dry over sodium sulfate, filter, and concentrate in vacuo. Purify the residue using silica gel chromatography (12 g column, 0-10% MeOH/CH$_2$Cl$_2$ over 45 min) to yield a yellow residue. Dissolve the residue in CH$_2$Cl$_2$ and the desired product precipitates.

Filter and wash with cold CH$_2$Cl$_2$ to afford the title compound as a pale, yellow powder (103 mg, 61%). mass spectrum (m/e). 445.3 [M+1]. $^1$H NMR (400 MHz, CDCl$_3$ (spiked with CD$_3$OD)): 8.29 (d, 1H, J=2.0 Hz), 7.59 (d, 1H, J=15.6 Hz), 7.57 (m, 1H), 7.47 (d, 1H, J=9.2 Hz), 7.38 (m, 1H), 7.20 (dd, 1H, J=8.8, 2.0 Hz), 7.13 (t, 1H, J=8.0 Hz), 6.52 (d, 1H, J=15.6 Hz), 3.82 (t, 1H, J=9.2 Hz), 3.72 (t, 1H, J=9.2 Hz), 3.53 (m, 1H), 3.46 (m, 1H), 3.04 (m, 1H), 2.37 (s, 6H), 2.29 (m, 1H), 2.08 (m, 1H).

Example 6

5-Phenyl-isoxazole-3-carboxylic acid [2-(3-dimethylamino-pyrrolidin-1-yl)-benzothiazol-6-yl]-amide

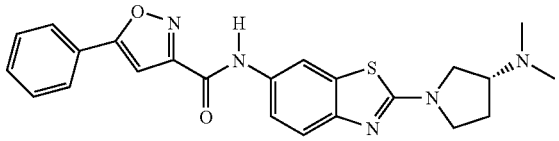

Combine 2-(3-dimethylamino-pyrrolidin-1-yl)-benzothiazol-6-ylamine (0.100 g, 0.381 mmol) (Example 1, step 3), dissolved in CH$_2$Cl$_2$ (5.0 mL), with 5-phenyl-isoxazole-3-carboxylic acid (0.079 g, 0.419 mmol), HATU (0.145 g, 0.381 mmol), and DIEA (0.20 mL, 1.14 mmol) in a 40 mL reaction vial and shake the mixture overnight at 40° C. Dilute the mixture with CH$_2$Cl$_2$ (25 mL) and wash with 1.0 M NaOH (25 mL) which results in emulsions forming. Wait 3 h for the emulsions to disappear, separate the layers and dry the organic portion over sodium sulfate. Filter and concentrate in vacuo to yield the compound as a yellow solid. Purify using silica gel chromatography (5% MeOH/CH$_2$Cl$_2$) to afford the title compound as a yellowish-white solid (117 mg, 71%). mass spectrum (m/e): 434.2 [M+1], 432.2 [M−1]. $^1$H NMR (400 MHz, DMSO-d6): δ10.76 (s, 1H), 8.27 (d, 1H, J=2 Hz), 7.98 (m, 2H), 7.56-7.63 (m, 4H), 7.49 (s, 1H), 7.45 (d, 1H, J=8.8 Hz), 3.73 (t, 1H, J=9.2 Hz), 3.64 (t, 1H, J=9.2 Hz), 3.49 (m, 1H), 3.29 (m, 1H), 2.90 (m, 1H), 2.21 (s, 6H), 2.19 (m, 1H), 1.91 (m, 1H).

Example 7

Biphenyl-4-carboxylic acid [2-(3-dimethylamino-pyrrolidin-1-yl)-benzothiazol-6-yl]-amide

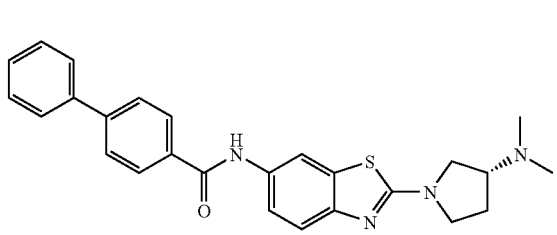

Combine 4-biphenylcarboxylic acid (0.124 g, 0.623 mmol), dichloromethane (5.0 mL), and DMF (3 drops) with stirring. Add oxalyl chloride (0.11 mL, 1.25 mmol) and stir the mixture for 2 h at room temperature. Concentrate the mixture in vacuo, add hexane (approximately 10 mL), re-concentrate in vacuo, and re-dissolve in CH$_2$Cl$_2$ (4.0 mL). Transfer the mixture to a 40 mL reaction vial and add a mixture of 2-(3-dimethylamino-pyrrolidin-1-yl)-benzothiazol-6-ylamine (0.109 g, 0.415 mmol) (Example 1, step 3) in CH$_2$Cl$_2$ (2.0 mL). Stir the mixture overnight at room temperature. Dilute the reaction mixture with CH$_2$Cl$_2$ (25 mL), wash with saturated NaHCO$_3$ (aqueous) (25 mL), and extract the aqueous phase with CH$_2$Cl$_2$ (25 mL). Wash the combined organic phases with saturated NaHCO$_3$ (aqueous) (2×25 mL), dry over sodium sulfate, filter, and concentrate in vacuo to yield a yellow solid. Purify the crude product using silica gel chromatography (40 g column, 5% MeOH/CH$_2$Cl$_2$) to afford the title compound (53 mg, 29%). mass spectrum (m/e): 443.4 [M+1], 441.3 [M−1]. $^1$H NMR (400 MHz, CDCl$_3$): δ 8.69-8.58 (m, 1H), 8.26 (s, 1H), 7.93 (d, 2H, J=8.0 Hz), 7.67 (d, 2H, J=7.6 Hz), 7.59 (d, 2H, J=7.2 Hz), 7.50-7.26 (m, 5H), 3.81 (t, 1H, J=10.4 Hz), 3.72 (t, 1H, J=8.8 Hz), 3.52 (m, 1H), 3.43 (m, 1H), 3.01 (m, 1H), 2.35 (s, 6H), 2.29 (m, 1H), 2.04 (m, 1H).

Example 8

2-(3,4-Dichloro-phenoxy)-N-[2-(3-dimethylamino-pyrrolidin-1-yl)-benzothiazol-6-yl]-acetamide

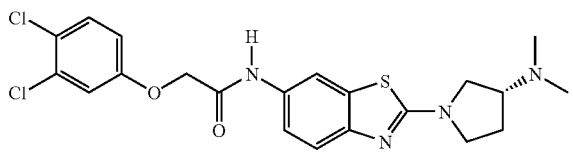

Prepare according to the procedures described in Example 1, step 4, Method B, using 3,4-dichlorophenoxyacetic acid (135 mg, 0.611 mmol) and 2-(3-dimethylamino-pyrrolidin-1-yl)-benzothiazol-6-ylamine (162 mg, 0.618 mmol) to afford the title compound, mass spectrum (m/e): 465 [M+H], 463 [M−H].

Example 9

3-(4-Chloro-phenyl)-N-[2-(3-dimethylamino-pyrrolidin-1-yl)-benzothiazol-yl]-acrylamide

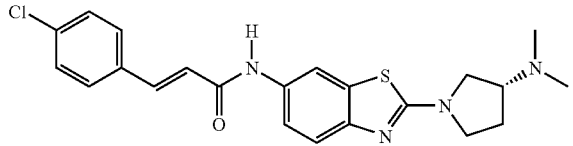

Method C: Suspend 4-chlorocinnamic acid (105 mg, 0.575 mmol) in CH$_2$Cl$_2$ (8 mL) and add DMF (2 drops). Add oxalyl chloride (250 μL, 2.87 mmol) and stir at room temperature for 4 h. Add hexane (approximately 10 mL), concentrate in vacuo, and re-dissolve in CH$_2$Cl$_2$ (8 mL). Add to a solution of 2-(3-dimethylamino-pyrrolidin-1-yl)-benzothiazol-6-ylamine (100 mg, 0.382 mmol) (Example 1, step 3) in CH$_2$Cl$_2$ (5.0 mL) and pyridine (100 μL), and shake at room temperature for 3 h. Dilute the reaction mixture with ethyl acetate, and wash with 1 N NaOH and brine. Adsorb the crude product on silica gel, and purify using silica gel chromatography, eluting with a gradient of MeOH in CH$_2$Cl$_2$ (10-20%) to afford the title compound (107 mg, 66%). mass spectrum (m/e): 427.0 [M+H]. $^1$H NMR (400 MHz, DMSO-d$_6$) δ 10.23 (s, 1H), 8.25 (s, 1H), 7.65 (d, 2H, J=8.4 Hz), 7.56 (d, 1H, J=15.6 Hz), 7.51 (d, 2H, J=8.3 Hz), 7.43-7.41 (m, 2H), 6.83 (d, 1H, J=15.4 Hz), 3.71 (dd, 1H, J=9.9, 6.8 Hz), 3.62 (dt, 1H, J=9.3, 2.3 Hz), 3.62 (td, 1H, J=13.0, 5.0 Hz), 3.31 (m, 1H), 2.89 (m, 1H), 2.21-2.19 (m, 7H), 1.90 (m, 1H).

Example 10

5-Chloro-benzofuran-2-carboxylic acid [2-(3-dimethylamino-pyrrolidin-1-yl)-benzothiazol-6-yl]-amide

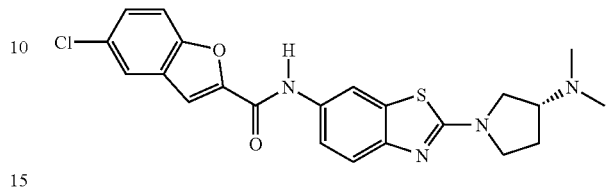

Prepare according to Method C (Example 9), using 5-chlorobenzofuran-2-carboxylic acid (109 mg, 0.554 mmol), oxalyl chloride (300 μL, 3.43 mmol), and 2-(3-dimethylamino-pyrrolidin-1-yl)-benzothiazol-6-ylamine (100 mg, 0.381 mmol) to afford the title compound (73 mg, 43%). mass spectrum (m/e): 441.0 [M+H]. $^1$H NMR (400 MHz, DMSO-d$_6$) δ 10.59 (s, 1H), 8.26 (d, 1H, J=1.8 Hz), 7.93 (d, 1H, J=2.2 Hz), 7.76 (d, 1H, J=8.6 Hz), 7.73 (d, 1H, J=0.9 Hz), 7.60 (dd, 1H, J=8.8, 2.2 Hz), 7.52 (dd, 1H, J=8.8, 2.2 Hz), 7.45 (d, 1H, J=8.4 Hz), 3.72 (dd, 1H, J=9.5, 7.3 Hz), 3.63 (m, 1H), 3.48 (m, 1H), 3.27 (m, 1H), 2.89 (m, 1H), 2.22-2.15 (m, 7H), 1.91 (m, 1H).

Example 11

N-[2-(3-Dimethylamino-pyrrolidin-1-yl)-benzothiazol-6-yl]-3-phenyl-acrylamide

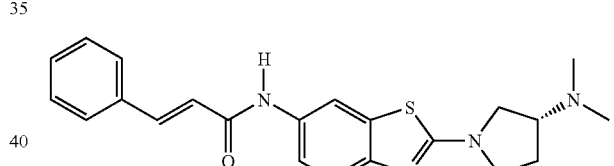

Prepare according to Method B, using trans-cinnamic acid (96 mg, 0.648 mmol) and 2-(3-dimethylamino-pyrrolidin-1-yl)-benzothiazol-6-ylamine (162 mg, 0.618 mmol) to afford the title compound (31 mg, 13%). mass spectrum (m/e): 393.0 [M+H]. $^1$H NMR (400 MHz, DMSO-d$_6$): δ 10.21 (s, 1H), 8.26 (d, 1H, J=1.3 Hz), 7.63 (d, 2H, J=7.0 Hz), 7.57 (d, 1H, J=15.7 Hz), 7.48-7.37 (m, 5H), 6.84 (d, 1H, J=15.8 Hz), 3.70 (dd, 1H, J =9.5, 7.0 Hz), 3.61 (m, 1H), 3.46 (m, 1H), 3.27 (m, 1H), 2.88 (m, 1H), 2.23-2.11 (m, 7H), 1.90 (m, 1H).

Example 12

N-[2-(3-Dimethylamino-pyrrolidin-1-yl)-benzothiazol-6-yl]-3-(3-fluoro-phenyl)-acrylamide

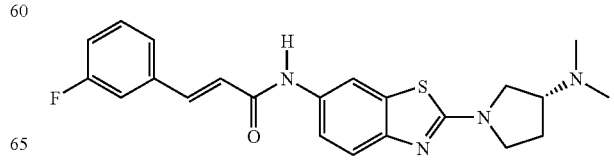

Prepare according to Method B, using trans-3-fluorocinnamic acid (98 mg, 0.590 mmol) and 2-(3-dimethylamino-pyrrolidin-1-yl)-benzothiazol-6-ylamine (162 mg, 0.618 mmol) to afford the title compound (41 mg, 16%). mass spectrum (m/e): 411.2 [M+H], 409.2 [M−H].

Example 13

N-[2-(3-Dimethylamino-pyrrolidin-1-yl)-benzothiazol-6-yl]-3-naphthalen-2-yl-acrylamide

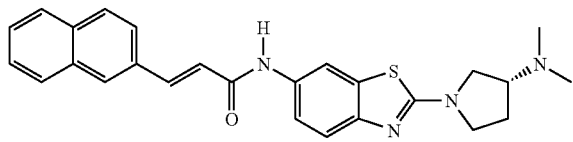

Prepare according to Method C (Example 9), using 3-(2-naphthyl)acrylic acid (69 mg, 0.348 mmol), oxalyl chloride (150 μL, 1.72 mmol), and 2-(3-dimethylamino-pyrrolidin-1-yl)-benzothiazol-6-ylamine (60 mg, 0.229 mmol) to afford the title compound (97 mg, 96%). mass spectrum (m/e): 442.0 [M+H]. $^1$H NMR (400 MHz, DMSO-$d_6$) δ 10.27 (s, 1H), 8.30 (d, 1H, J=1.3 Hz), 8.14 (s, 1H), 8.00-7.92 (m, 3H), 7.78 (dd, 1H, J=8.5, 1.6 Hz), 7.71 (d, 1H, J=15.6), 7.59-7.54 (m, 2H), 7.45-7.42 (m, 2H), 6.97 (d, 1H, J=15.4 Hz), 3.71 (t, 1H, J=8.1 Hz), 3.62 (t, 1H, J=7.9 Hz), 3.47 (m, 1H), 3.26 (m, 1H), 2.89 (m, 1H), 2.21-2.17 (m, 7H), 1.94-1.86 (m, 1H).

Example 14

N-[2-(3-Dimethylamino-pyrrolidin-1-yl)-benzothiazol-6-yl]-3-(4-methoxy-phenyl)-acrylamide

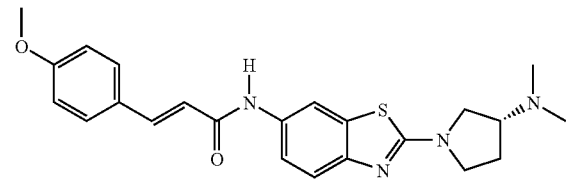

Prepare according to Method B, using trans-4-methoxycinnamic acid (112 mg, 0.629 mmol) and 2-(3-dimethylamino-pyrrolidin-1-yl)-benzothiazol-6-ylamine (162 mg, 0.618 mmol) to afford the title compound (15 mg, 6%). mass spectrum (m/e): 423.3 [M+H], 421.3 [M−H].

Example 15

3-(3,4-Difluoro-phenyl)-N-[2-(3-dimethylamino-pyrrolidin-1-yl)-benzothiazol-6-yl]-acrylamide

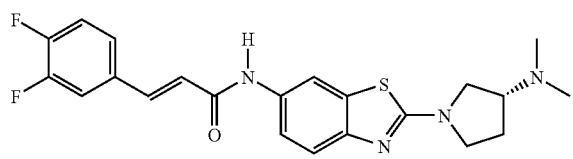

Prepare according to Method C (Example 9), using 3,4-difluorocinnamic acid (107 mg, 0.581 mmol), oxalyl chloride (250 μL, 2.87 mmol), and 2-(3-dimethylamino-pyrrolidin-1-yl)-benzothiazol-6-ylamine (100 mg, 0.382 mmol) to afford the title compound (126 mg, 77%). mass spectrum (m/e): 429.0 [M+H], 427.0 [M−H]. $^1$H NMR (400 MHz, DMSO-$d_6$) δ 10.23 (s, 1H), 8.25 (d, 1H, J=0.9 Hz), 7.72 (m, 1H), 7.55 (d, 1H, J=15.3 Hz), 7.52-7.48 (m, 2H), 7.43-7.41 (m, 2H), 6.80 (d, 1H, J=15.8 Hz), 3.70 (dd, 1H, J=9.7, 7.0 Hz), 3.61 (m, 1H), 3.47 (m, 1H), 3.26 (dd, 1H, J=9.9, 8.1 Hz), 2.88 (m, 1H), 2.21-2.17 (m, 7H), 1.90 (m, 1H).

Example 16

N-[2-(3-Dimethylamino-pyrrolidin-1-yl)-benzothiazol-6-yl]-2-methyl-3-phenyl-acrylamide

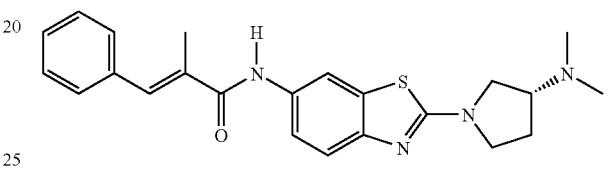

Prepare according to Method B, using α-methylcinnamic acid (99 mg, 0.610 mmol) and 2-(3-dimethylamino-pyrrolidin-1-yl)-benzothiazol-6-ylamine (162 mg, 0.618 mmol) to yield the title compound (31 mg, 12%). mass spectrum (m/e): 407.3 [M+H], 405.2 [M−H].

Example 17

N-[2-(3-Dimethylamino-pyrrolidin-1-yl)-benzothiazol-6-yl]-3-(4-trifluoromethyl-phenyl)-acrylamide

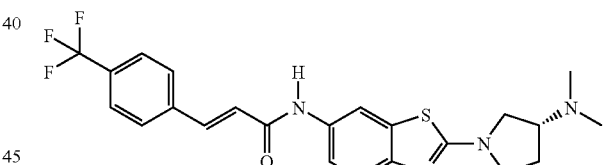

Method D: Suspend 4-trifluoromethylcinnamic acid (2.18 g, 10.1 mmol) in $CH_2Cl_2$ (50 mL) and add DMF (3 drops). Add oxalyl chloride (5.0 mL, 287 mmol) and stir at room temperature for 2.5 h. Add hexane (approximately 10 mL) to precipitate the acid chloride, concentrate in vacuo, and re-dissolve in dichloromethane (50 mL). Add an aliquot of the acid chloride (5.0 mL, 1.02 mmol) to a solution of 2-(3-dimethylamino-pyrrolidin-1-yl)-benzothiazol-6-ylamine (200 mg, 0.684 mmol) in THF (15 mL) containing approximately 2.5 g of diisopropylamine, polymer bound (100-200 mesh, 1% cross linked, Aldrich) and shake at room temperature overnight. Filter and wash with DMF (5 mL). Add approximately 2 g PS—$SO_3$H resin and shake at room temperature for 30 min. Filter and wash with copious amounts of MeOH/$CH_2Cl_2$/MeOH. Transfer the resin to a 40 mL vial and add 2 N ammonia in EtOH (15 mL) and shake at room temperature for 1 h. Filter and wash with THF (10 mL), and concentrate the filtrate in vacuo to afford the title compound (46 mg, 15%). mass spectrum (m/e): 461.2 [M+H], 459.2 [M−H]. $^1$H NMR (400 MHz, DMSO-$d_6$): δ 10.31 (s, 1H), 8.27 (s, 1H), 7.83 (m, 4H), 7.64 (d, 1H, J=15.8 Hz), 7.44-7.42 (m, 2H), 6.96 (d, 1H, J=16.3 Hz), 3.71 (dd, 1H, J 9.4, 7.2 Hz), 3.62 (m, 1H), 3.47 (m, 1H), 3.26 (m, 1H), 2.89 (m, 1H), 2.22-2.17 (m, 7H), 1.90 (m, 1H).

Example 18

5-Fluoro-1H-indole-2-carboxylic acid [2-(3-dimethylamino-pyrrolidin-1-yl)-benzothiazol-6-yl]-amide

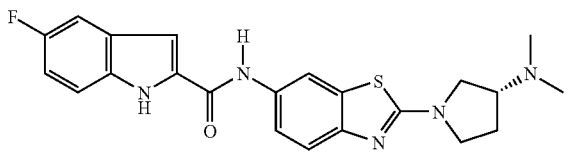

Prepare according to Method B, using 5-fluoroindole-2-carboxylic acid (110 mg, 0.614 mmol) and 2-(3-dimethylamino-pyrrolidin-1-yl)-benzothiazol-6-ylamine (162 mg, 0.618 mmol) to yield the title compound (45 mg, 28%). mass spectrum (m/e): 424 [M+H], 422 [M−H].

Example 19

Benzo[b]thiophene-2-carboxylic acid [2-(3-dimethylamino-pyrrolidin-1-yl)-benzothiazol-6-yl]-amide

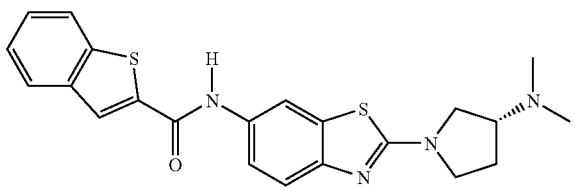

Prepare according to Method C (Example 9), using benzothiophene-2-carboxylic acid (123 mg, 0.685 mmol), oxalyl chloride (300 μL, 3.44 mmol), and 2-(3-dimethylamino-pyrrolidin-1-yl)-benzothiazol-6-ylamine (100 mg, 0.381 mmol) to afford the title compound (50 mg, 31%). mass spectrum (m/e): 423.0 [M+H]. $^1$H NMR (400 MHz, DMSO-d$_6$) δ 10.53 (s, 1H), 8.35 (s, 1H), 8.25 (d, 1H, J=2.2 Hz), 8.06 (dd, 1H, J=6.5, 1.9 Hz), 8.01 (dd, 1H, J=6.2, 2.7 Hz), 7.55 (dd, 1H, J=8.8, 2.2 Hz), 7.50-7.43 (m, 3H), 3.72 (m, 1H), 3.63 (m, 1H), 3.48 (m, 1H), 3.31 (m, 1H), 2.90 (m, 1H), 2.22-2.17 (m, 7H), 1.92 (m, 1H).

Example 20

Isoquinoline-3-carboxylic acid [2-(3-dimethylamino-pyrrolidin-1-yl)-benzothiazol-6-yl]-amide

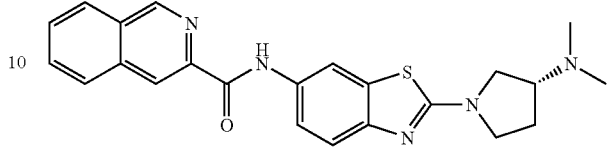

Prepare according to Method B. using isoquinoline-3-carboxylic acid monohydrate (74 mg, 0.427 mmol) and 2-(3-dimethylamino-pyrrolidin-1-yl)-benzothiazol-6-ylamine (100 mg, 0.381 mmol) to afford the title compound (85 mg, 53%). mass spectrum (m/e): 418.0 [M+H]. $^1$H NMR (400 MHz, DMSO-d$_6$) δ 10.76 (s, 1H), 9.47 (s, 1H), 8.70 (s, 1H), 8.44 (d, 1H, J=2.2 Hz), 8.30 (d, 1H, J=7.9 Hz), 8.25 (d, 1H, J=7.9 Hz), 7.91 (t, 1H, J=7.7 Hz), 7.84 (t, 1H, J=7.2 Hz), 7.78 (dd, 1H, J=8.8, 2.3 Hz), 7.46 (d, 1H, J=8.8 Hz), 3.73 (dd, 1H, J=9.6, 7.1 Hz), 3.63 (m, 1H), 3.48 (m, 1H), 3.29 (m, 1H), 2.93 (m, 1H), 2.25-2.15 (m, 7H), 1.92 (m, 1H).

Example 21

4'-Fluoro-biphenyl-4-carboxylic acid {2-[(2-dimethylamino-ethyl)-methyl-amino]-benzothiazol-6-yl}-amide Step 1. 2-Bromo-6-nitrobenzthiazole

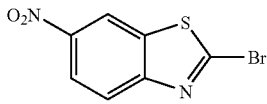

Suspend 2-amino-6-nitrobenzthiazole (20.0 g, 102 mmol) and copper (I) bromide (1.75 g, 12.2 mmol) in 18% HBr (aqueous) (200 mL) and water (180 mL). Slowly add sodium nitrite (61.0 g, 884 mmol). Continue to stir at room temperature for 30 min. Filter and dry on the filter flask overnight, to afford the title compound (24.6 g, 93%). $^1$H NMR (400 MHz, DMSO-d$_6$): δ 9.19 (d, 1H, J=2.2 Hz), 8.36 (dd, 1H, J=9.0, 2.4 Hz), 8.20 (d, 1H, J=9.2 Hz).

Step 2. N,N,N'-Trimethyl-N'-(6-nitro-benzothiazol-2-yl)-ethane-1,2-diamine

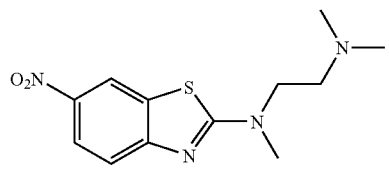

Suspend 2-bromo-6-nitrobenzthiazole (5.00 g, 19.3 mmol) in THF (150 mL). Add N,N, N-trimethylethylene diamine (5.2 g, 40.0 mmol) and stir at room temperature for 6 h. Dilute with CH$_2$Cl$_2$, wash with saturated sodium bicarbonate (2×) and brine, and concentrate in vacuo to afford the crude title compound (5.79 mg, 100%). Carry the crude product on as is.

$^1$H NMR (400 MHz, CDCl$_3$): δ 8.50 (d, 1H, J=2.2 Hz), 8.19 (dd, 1H, J=8.8, 2.2 Hz), 7.49 (d, 1H, J=9.2 Hz), 3.73 (m, 2H), 3.27 (s, 3H), 2.64 (t, 2H, J=6.8 Hz), 2.33 (s, 6H).

Step 3. N$^2$-(2-Dimethylamino-ethyl)-N$^2$-methyl-benzothiazole-2,6-diamine

Combine N,N,N'-Trimethyl-N'-(6-nitro-benzothiazol-2-yl)ethane-1,2-diamine (5.79 g, 20.6 mmol) and 5% palladium on carbon (5.02 g) in EtOH (200 mL) and THF (25 mL). Shake on a Parr shaker at 60 psi of hydrogen at room temperature for 18 h. Filter the reaction mixture through filter paper, wash with EtOH (50 mL), and concentrate in vacuo to afford the crude title compound (4.1 g, 80%). The crude product was carried on as is. $^1$H NMR (400 MHz, DMSO-d$_6$): δ 7.10 (d, 1H, J=8.4 Hz), 6.86 (d, 1H, J=1.8 Hz), 6.52 (dd, 1H, J=8.4, 2.2 Hz), 4.80 (br s, 2H), 3.51 (t, 2H, J=6.6 Hz), 3.04 (s, 3H), 2.48 (m, 2H), 2.18 (s, 6H).

Step 4. 4'-Fluoro-biphenyl-4-carboxylic acid {2-[(2-dimethylamino-ethyl)-methyl-amino]-benzothiazol-6-yl}-amide Prepare according to Method A, using 4-(4-fluorophenyl)benzoic acid (572 mg, 2.65 mmol), HATU (1.06 g, 2.79 mmol), N$^2$-(2-dimethylamino-ethyl)-N$^2$-methyl-benzothiazole-2,6-diamine (500 mg, 2.00 mmol), DIEA (1.15 mL, 6.60 mmol), and a chromatography gradient of MeOH in CH$_2$Cl$_2$ (7-17%) to afford the title compound (535 mg, 60%). mass spectrum (m/e): 449.0 [M+H]. $^1$H NMR (400 MHz, DMSO-d$_6$): δ 10.29 (s, 1H), 8.26 (d, 1H, J=2.2 Hz), 8.06 (d, 2H, J=8.4 Hz), 7.84-7.78 (m, 4H), 7.57 (dd, 1H, J=8.8, 2.2 Hz), 7.41 (d, 1H, J=8.8 Hz), 7.34 (t, 2H, J=8.8 Hz), 3.61 (t, 2H, J=6.8 Hz), 3.14 (s, 3H), 2.52 (m, 2H), 2.20 (s, 6H).

Example 22

N-{2-[(2-Dimethylamino-ethyl)-methyl-amino]-benzothiazol-6-yl}-3-(4-trifluoromethyl-phenyl)-acrylamide

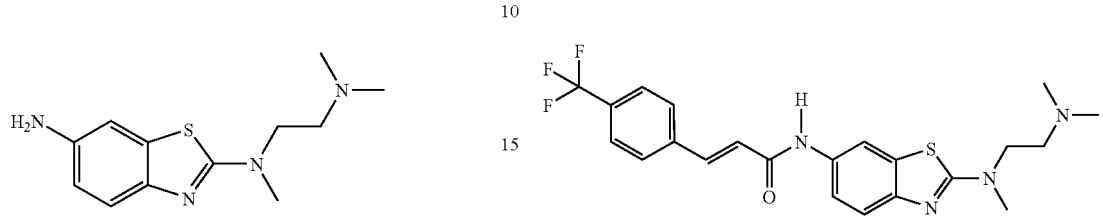

Prepare according to Method A, using trans-4-trifluoromethylcinnamic acid (130 mg, 0.60 mmol), HATU (229 mg, 0.602 mmol), N$^2$-(2-dimethylamino-ethyl)-N$^2$-methyl-benzothiazole-2,6-diamine (100 mg, 0.400 mmol), DIEA (260 μL, 1.49 mmol), and a chromatography gradient of MeOH in CH$_2$Cl$_2$ (8-20%) to afford the title compound (38 mg, 21%). mass spectrum (m/e): 449.0 [M+H], 447.0 [M−H]. $^1$H NMR (400 MHz, DMSO-d$_6$): δ 10.50 (s, 1H), 8.31 (d, 1H, J=2.2 Hz), 7.87-7.78 (m, 4H), 7.64 (d, 1H, J=15.8 Hz), 7.52 (dd, 1H, J=8.8, 2.2 Hz), 7.44 (d, 1H, J=8.8 Hz), 7.03 (d, 1H, J=15.8 Hz), 3.97 (dd, 2H, J=6.4, 6.4 Hz), 3.39 (dd, 2H, J=6.2, 6.2 Hz), 3.13 (s, 3H), 2.85 (s, 6H).

Example 23

N-{2-[(2-Dimethylamino-ethyl)-methyl-amino]-benzothiazol-6-yl}-3-(4-fluoro-phenyl)-acrylamide

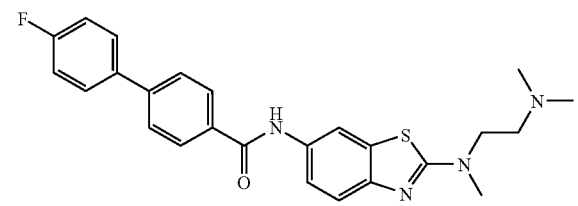

Prepare according to Method A, using 4-fluorocinnamic acid (100 mg, 0.602 mmol), HATU (228 mg, 0.600 mmol), N$^2$-(2-dimethylamino-ethyl)-N$^2$-methyl-benzothiazole-2,6-diamine (100 mg, 0.400 mmol), DIEA (260 μL, 1.49 mmol), and a chromatography gradient of MeOH in CH$_2$Cl$_2$ (8-20%) to yield the title compound (18 mg, 11%). mass spectrum (m/e): 399.0 [M+H]. $^1$H NMR (400 MHz, DMSO-d$_6$): δ 10.38 (s, 1H), 8.30 (d, 1H, J=1.8 Hz), 7.72-7.66 (m, 2H), 7.57 (d, 1H, J=15.8 Hz), 7.50 (dd, 1H, J=8.8, 2.2 Hz), 7.43 (d, 1H, J=8.8 Hz), 7.32-7.25 (m, 2H), 6.84 (d, 1H, J=15.8 Hz), 3.95 (dd, 2H, J=6.4, 6.4 Hz), 3.39-3.33 (m, 2H), 3.13 (s, 3H), 2.83 (s, 6H).

Example 24

4'-Fluoro-biphenyl-4-carboxylic acid [2-(isopropyl-methyl-amino)-benzothiazol-6-yl]-amide Step 1. Isopropyl-methyl-(6-nitro-benzothiazol-2-yl)-amine

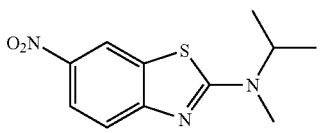

Suspend 2-chloro-6-nitrobenzthiazole (1.46 g, 6.80 mmol) in THF (20 mL). Slowly add N,N-isopropylmethyl amine (1.50 mL, 14.4 mmol). Stir the reaction at room temperature overnight. Dilute the reaction with ethyl acetate, wash with saturated NaHCO$_3$ (aqueous) and brine, and concentrate in vacuo. Absorb the crude product on silica gel, and purify using silica gel chromatography, eluting with a gradient of MeOH in CH$_2$Cl$_2$ (0-3%) to afford the title compound (1.36 g, 80%). $^1$H NMR (400 MHz, DMSO-d$_6$): δ 8.79 (d, 1H, J=2.2 Hz), 8.13 (dd, 1H, J=8.8, 2.6 Hz), 7.49 (d, 1H, J=8.8 Hz), 4.45 (m, 1H), 3.06 (s, 3H), 1.26 (d, 6H, J=6.6 Hz).

Step 2. N$^2$-Isopropyl-N$^2$-methyl-benzothiazole-2,6-diamine

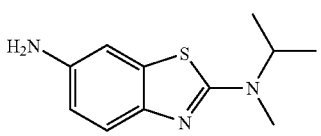

Combine isopropyl-methyl-(6-nitro-benzothiazol-2-yl)-amine (1.32 g, 5.25 mmol) and 5% palladium on carbon (3.00 g) in EtOH (50 mL) and THF (25 mL). Shake on a Parr shaker at 60 psi hydrogen at room temperature for 7 h. Filter with filter paper, washing with EtOH (20 mL), and concentrate in vacuo to afford the title compound (1.04 g, 90%). $^1$H NMR (400 MHz, CDCl$_3$): δ 7.36 (d, 1H, J=8.4 Hz), 6.93 (d, 1H, J=2.2 Hz), 6.67 (dd, 1H, J=8.6, 2.4 Hz), 4.31 (m, 1H), 3.62 (s, 2H), 2.99 (s, 3H), 1.25 (d, 6H, J=6.6 Hz).

Step 3. 4'-Fluoro-biphenyl-4-carboxylic acid [2-(isopropyl-methyl-amino)-benzothiazol-6-yl]-amide

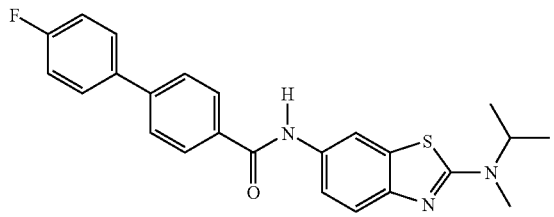

Prepare according to Method A, using 4-(4-fluorophenyl) benzoic acid (253 mg, 1.17 mmol), HATU (451 mg, 1.19 mmol), N$^2$-Isopropyl-N$^2$-methyl-benzothiazole-2,6-diamine (200 mg, 0.904 mmol), DIEA (520 μL, 2.99 mmol), and a chromatography gradient of MeOH in CH$_2$Cl$_2$ (0-5%) to afford the title compound (196 mg, 52%). mass spectrum (m/e): 420.0 [M+H], 418.0 [M−H]. $^1$H NMR (400 MHz, DMSO-d$_6$): δ 10.28 (s, 1H), 8.27 (d, 1H, J=2.2 Hz), 8.06 (d, 2H, J=8.4 Hz), 7.85-7.78 (m, 4H), 7.56 (dd, 1H, J=8.8, 2.2 Hz), 7.40 (d, 1H, J=8.2 Hz), 7.37-7.31 (m, 2H), 4.34 (m, 1H), 2.98 (s, 3H), 1.23 (d, 6H, J=6.6 Hz).

Example 25

5-(4-Chloro-phenyl)-isoxazole-3-carboxylic acid [2-(isopropyl-methyl-amino)-benzothiazol-6-yl]-amide

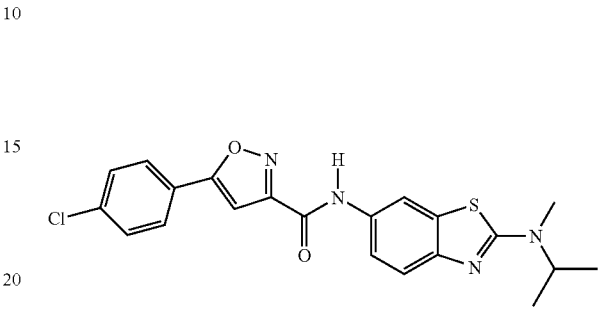

Prepare according to Method C (Example 9), using 5-(4-chlorophenyl)isoxazole-3-carboxylic acid (39 mg, 0.174 mmol), oxalyl chloride (300 μL, 3.44 mmol), and N$^2$-isopropyl-N$^2$-methyl-benzothiazole-2,6-diamine (33 mg, 0.149 mmol) to afford the title compound (23 mg, 36%). mass spectrum (m/e): 427.0 [M+H]. $^1$H NMR (400 MHz, DMSO-d$_6$) δ 10.76 (s, 1H), 8.24 (d, 1H, J=2.2 Hz), 8.01 (d, 2H, J=8.8 Hz), 7.66 (d, 2H, J=8.4 Hz), 7.60 (dd, 1H, J=8.8, 2.2 Hz), 7.54 (s, 1H), 7.41 (d, 1H, J=8.4 Hz), 4.34 (m, 1H), 2.98 (s, 3H), 1.23 (d, 6H, J=6.6 Hz).

Example 26

N-[2-(Isopropyl-methyl-amino)-benzothiazol-6-yl]-3-(4-trifluoromethyl-phenyl)-acrylamide

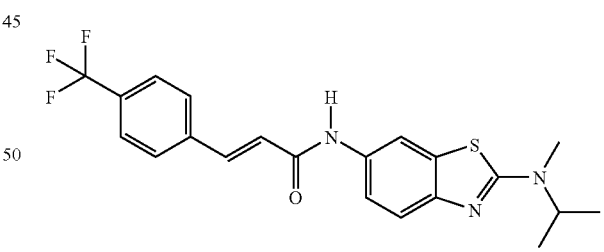

Prepare according to Method D (Example 17), using 4-trifluoromethylcinnamoyl chloride (526 mg, 2.24 mmol) (Example 17) and N$^2$-isopropyl-N$^2$-methyl-benzothiazole-2,6-diamine (332 mg, 1.50 mmol), to afford the title compound (163 mg, 26%). mass spectrum (m/e): 420.2 [M+H], 418.2 [M−H]. $^1$H NMR (400 MHz, DMSO-d$_6$): δ 10.30 (s, 1H), 8.25 (d, 1H, J=1.8 Hz), 7.87-7.78 (m, 4H), 7.64 (d, 1H, J=15.8 Hz), 7.43 (dd, 1H, J=8.6, 1.9 Hz), 7.39 (d, 1H, J=8.4 Hz), 6.96 (d, 1H, J=15.4 Hz), 4.32 (m, 1H), 2.97 (s, 3H), 1.22 (d, 6H, J=7.0 Hz).

Example 27

N-[2-(3-Dimethylamino-pyrrolidin-1-yl)-benzooxazol-5-yl]-3-(4-trifluoromethyl-phenyl)-acrylamide Step 1. 5-Nitro-3H-benzooxazole-2-tone

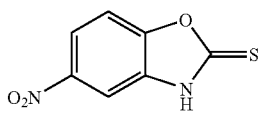

Combine 2-amino-4-nitrophenol (15.8 g, 102 mmol) and potassium xanthate (18.2 g, 114 mmol) in pyridine (200 mL). Reflux for 1 hour and then cool to room temperature. Pour the reaction into concentrated HCl (100 mL) and ice. Filter and wash the product with 1 N HCl to remove excess pyridine. Dry in a vacuum oven at 50° C. for 48 h to afford the title compound (15.9 g, 79%). $^1$H NMR (400 MHz, DMSO-$d_6$): δ 8.18 (dd, 1H, J=8.8, 2.2 Hz), 7.93 (d, 1H, J=2.2 Hz), 7.73 (d, 1H, J=8.8 Hz).

Step 2. 2-Methylsulfanyl-5-nitro-benzooxazole

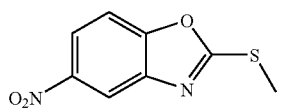

Suspend 5-nitro-3H-benzooxazole-2-thione (5.15 g, 26.3 mmol) in THF (150 mL). Cool in an ice bath to 5° C. and add sodium hydride (60% dispersion in mineral oil) (1.7 g, 42.5 mmol). Stir for 15 min at 5° C. Add dropwise iodomethane (5.0 mL, 80.1 mmol) dissolved in THF (30 mL) over 1 h. Continue to stir at room temperature for 4 h. Absorb the reaction mixture onto silica gel, and purify using silica gel chromatography, eluting with a gradient of EtOAc in hexane (0-60%) to afford the title compound (4.75 g, 86%). $^1$H NMR (400 MHz, DMSO-$d_6$): δ 8.47 (d, 1H, J=3.1 Hz), 8.24 (dd, 1H, J=9.0, 2.4 Hz), 7.89 (d, 1H, J=8.8 Hz), 2.81 (s, 3H).

Step 3. Dimethyl-[1-(5-nitro-benzooxazol-2-yl)-pyrrolidin-3-yl]-amine

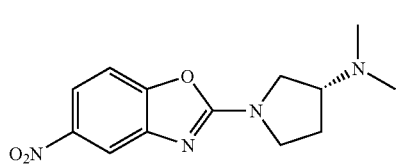

Suspend 2-methylsulfanyl-5-nitro-benzooxazole (1.68 g, 7.99 mmol) in toluene (8 mL). Add (3R)-(+)-3-(dimethylamino)pyrrolidine (1.8 mL) and heat to 70° C. overnight. Cool the reaction to room temperature, dilute with toluene (10 mL) and filter. Wash the product with toluene (5 mL) and hexane (10 mL). Dry on the filter flask for 30 min to afford the title compound (1.00 g, 45%). $^1$H NMR (400 MHz, DMSO-$d_6$): δ 8.03 (d, 1H, J=2.2 Hz), 7.94 (dd, 1H, J=8.6, 2.4 Hz), 7.62 (d, 1H, J=8.8 Hz), 3.81 (dd, 1H, J=10.1, 7.0 Hz), 3.75 (m, 1H), 3.57 (dt, 1H, J=10.0, 7.2 Hz), 3.34 (m, 1H), 2.86 (m, 1H), 2.21-2.13 (m, 7H), 1.87 (m, 1H).

Step 4. 2-(3-Dimethylamino-pyrrolidin-1-yl)-benzooxazol-5-ylamine

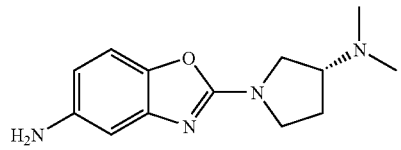

Combine dimethyl-[1-(5-nitro-benzooxazol-2-yl)-pyrrolidin-3-yl]-amine (1.00 g, 3.62 mmol) and Fe$^0$ (1.98 g, 35.4 mmol) in acetic acid (20 mL) and stir at 40° C. for 2 h. Dilute with water (50 mL) and filter through Celite®. Wash with copious amounts of water and MeOH. Make the filtrate alkaline with 5 N NaOH and extract twice with CH$_2$Cl$_2$ (2×). Concentrate in vacuo to afford the title compound (769 mg, 86%). $^1$H NMR (400 MHz, CDCl$_3$): δ 7.00 (d, 1H, J=8.4 Hz), 6.70 (d, 1H, J=2.2 Hz), 6.32 (dd, 1H, J=8.4, 2.6 Hz), 3.88 (dd, 1H, J=9.9, 7.1 Hz), 3.81 (m, 1H), 3.62-3.50 (m, 3H), 3.39 (dd, 1H, J=10.1, 8.8 Hz), 2.83 (m, 1H), 2.30 (s, 6H), 2.21 (m, 1H), 1.93 (m, 1H).

Step 5. N-[2-(3-Dimethylamino-pyrrolidin-1-yl)-benzooxazol-5-yl]-3-(4-trifluoromethyl-phenyl)-acrylamide

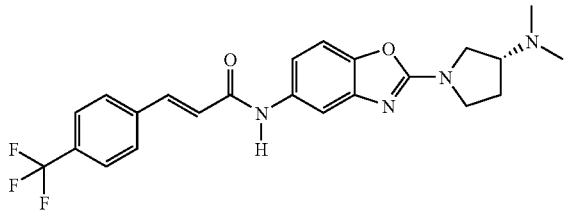

Prepare according to Method C (Example 9), using trans-4-trifluorocinnamic acid (150 mg, 0.694 mmol), oxalyl chloride (300 μL, 3.43 mmol), and 2-(3-dimethylamino-pyrrolidin-1-yl)-benzooxazol-5-ylamine (106 mg, 0.430 mmol) to afford the title compound (78 mg, 44%). mass spectrum (m/e): 445.3 [M+H], 443.3 [M−H]. $^1$H NMR (400 MHz, DMSO-$d_6$): δ 10.26 (s, 1H), 7.86-7.79 (m, 4H), 7.72 (d, 1H, J=2.3 Hz), 7.66 (d, 1H, J=15.8 Hz), 7.34 (d, 1H, J=8.8 Hz), 7.26 (dd, 1H, J=8.6, 2.0 Hz), 6.96 (d, 1H, J=15.8 Hz), 3.78 (dd, 1H, J=9.9, 7.0 Hz), 3.71 (m, 1H), 3.53 (m, 1H), 3.31 (m, 1H), 2.84 (m, 1H), 2.22-2.10 (m, 7H), 1.85 (m, 1H).

Example 28

N-[2-(3-Dimethylamino-pyrrolidin-1-yl)-benzooxazol-5-yl]-3-(4-methoxy-phenyl)-acrylamide

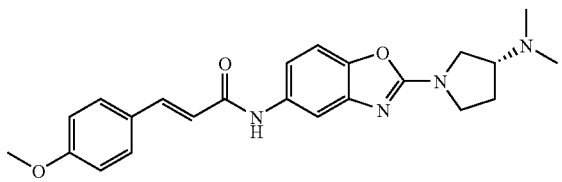

Prepare according to Method C (Example 9), using 4-methoxycinnamic acid (110 mg, 0.617 mmol), oxalyl chloride (300 μL, 3.43 mmol), and 2-(3-dimethylamino-pyrrolidin-1-yl)-benzooxazol-5-ylamine (99 mg, 0.402 mmol) to afford the title compound (118 mg, 72%). mass spectrum (m/e): 407.4 [M+H], 405.3 [M−H].

Example 29

N-[2-(3-Dimethylamino-pyrrolidin-1-yl)-benzooxazol-5-yl]-3-(4-fluoro-phenyl)-acrylamide

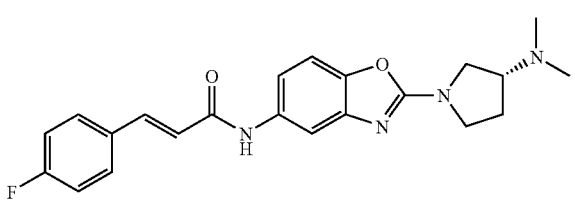

Prepare according to Method C (Example 9), using 4-fluorocinnamic acid (107 mg, 0.643 mmol), oxalyl chloride (300 μL, 3.43 mmol), and 2-(3-dimethylamino-pyrrolidin-1-yl)-benzooxazol-5-ylamine (97 mg, 0.399 mmol) to afford the title compound (109 mg, 69%). mass spectrum (m/e): 395.3 [M+H], 393.3 [M−H]. $^1$H NMR (400 MHz, CDCl$_3$): δ 7.68 (m, 1H), 7.53-7.35 (m, 4H), 7.17 (m, 1H), 7.07-6.95 (m, 2H), 6.49 (d, 1H, J=15.4 Hz), 3.94-3.77 (m, 2H), 3.59 (m, 1H), 3.44 (m, 1H), 2.89 (m, 1H), 2.31 (s, 6H), 2.24 (m, 1H), 1.96 (m, 1H).

Example 30

4'-Fluoro-biphenyl-4-carboxylic acid [2-(3-dimethylamino-pyrrolidin-1-yl)-benzooxazol-5-yl]-amide

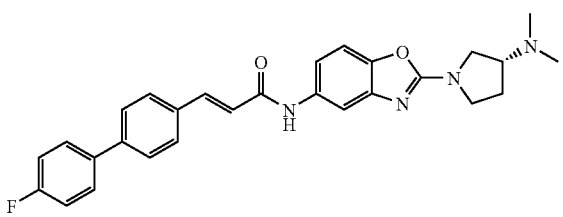

Combine 2-(3-dimethylamino-pyrrolidin-1-yl)-benzooxazol-5-ylamine (0.100 g, 0.406 mmol), 4-(4-fluorophenyl)benzoic acid (0.073 g, 0.338 mmol), and HATU (0.129 g, 0.338 mmol) in CH$_2$Cl$_2$ and add DIEA (0.18 mL, 1.01 mmol). Shake the mixture in a shaker block at 40° C. for 72 h. Dilute the reaction mixture with CH$_2$Cl$_2$ (30 mL), and wash with saturated NaHCO$_3$ (aqueous) (2×25 mL). Dry the organic phase over anhydrous sodium sulfate, filter, and concentrate in vacuo. Subject the crude product to flash column chromatography (40 g column) eluting with 8% MeOH/CH$_2$Cl$_2$, to yield the title compound as a bluish-white solid (0.116 g, 65%). mass spectrum (m/e): 445.3 [M+1], 443.3 [M−1]. $^1$H NMR (400 MHz, DMSO-d6): δ 10.23 (s, 1H), 8.05 (d, 2H, J=8.4 Hz), 7.85-7.79 (m, 4H), 7.75 (d, 1H, J=2.2 Hz), 7.41-7.30 (m, 4H), 3.79 (dd, 1H, J=9.9, 7.1 Hz), 3.72 (m, 1H), 3.54 (m, 1H), 3.31 (m, 1H), 2.86 (m, 1H), 2.25-2.12 (m, 7H), 1.86 (m, 1H).

Example 31

4'-Fluoro-biphenyl-4-carboxylic acid (2-{methyl-[3-(methyl-quinolin-2-yl-amino)-propyl]-amino}-benzothiazol-6-yl)-amide Step 1. 2-Chloro-benzothiazol-6-ylamine

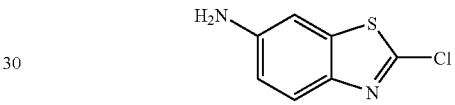

Suspend 2-Chloro-6-nitro-benzothiazole (21.43 g, 99.8 mmol) in glacial acetic acid (300 mL). Add elemental iron (12.9 g, 231 mmol) and stir at 40° C. for 5 h. Filter the reaction mixture through Celite®, concentrate in vacuo, and adsorb onto silica gel. Subject the residue to silica gel flash column chromatography in two portions [(120 g column, 0-10% CH$_3$OH/CH$_2$Cl$_2$), (120 g column, 0-5% CH$_3$O/CH$_2$Cl$_2$)] to yield the desired product (6.17 g, 33%). mass spectrum (m/e): 185.0 (M+1).

Step 2. 4'-Fluoro-biphenyl-4-carboxylic acid (2-chloro-benzothiazol-6-yl)-amide

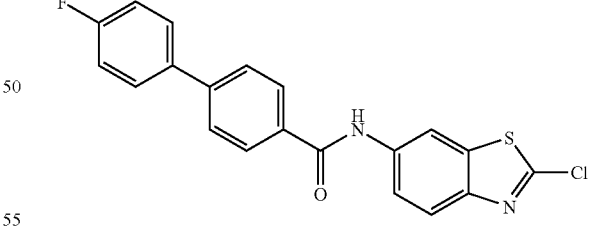

Add oxalyl chloride (10 mL, 114.6 mmol) and DMF (4 drops) to a stirring suspension of 4'-fluoro-biphenyl-4-carboxylic acid (4.9 g, 22.7 mmol) in CH$_2$Cl$_2$ (150 mL). Stir the reaction mixture at room temperature for 3 h. Concentrate the mixture in vacuo, add n-hexane, re-concentrate, and re-dissolve in CH$_2$Cl$_2$. Add the resultant 4'-fluoro-biphenyl-4-carbonyl chloride solution to a mixture of 2-chloro-benzothiazol-6-ylamine (3.31 g, 17.9 mmol) and pyridine (3.0 mL) in CH$_2$Cl$_2$ (150 mL). Stir the reaction mixture overnight at room temperature. Dilute the reaction mixture with CH$_2$Cl$_2$. Wash the reaction mixture twice with 1.0M HCl and once with 1.0M NaOH. Dry the mixture over Na₂SO₄, concentrate in vacuo, and triturate with MeOH to yield the desired product (6.34 g, 93%). ¹H NMR (400 MHz, DMSO-d6): δ10.59 (s, 1H), 8.69 (d, J=1.6 Hz, 1H), 8.09 (d, J=8.0 Hz, 2H), 7.96 (d, J=8.8 Hz, 1H), 7.87-7.79 (m, 5H), 7.38-7.31 (m, 2H).

Step 3. 4'-Fluoro-biphenyl-4-carboxylic acid (2-{methyl-[3-(methyl-quinolin-2-yl-amino)-propyl]-amino)-benzothiazol-6-yl}-amide Allow the mixture to warm to room temperature and stir overnight. Adsorb the reaction mixture onto silica gel and subject to flash column chromatography in 2 batches (330 g, 120 g columns, eluting with 10-50% ethyl acetate/n-hexane both times) to yield the desired product (4.93 g, 41%). ¹H NMR (400 MHz, DMSO-d6): δ 8.47 (d, J=2.4 Hz, 1H), 8.23 (dd, J=9.2, 2.6 Hz, 1H), 7.88 (d, J=8.8 Hz, 1H), 3.37 (q, J=6.8 Hz, 2H), 1.45 (t, J=7.6 Hz, 3H).

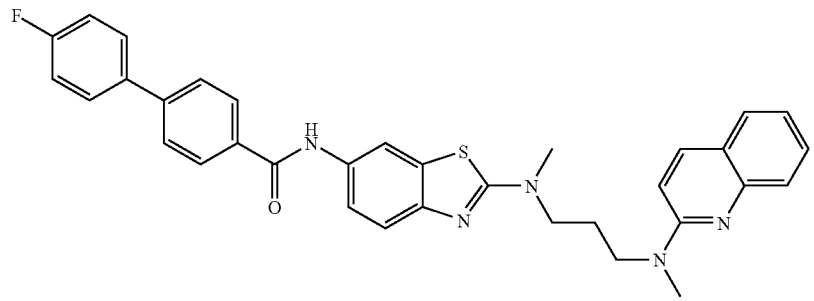

Add 4'-chloro-biphenyl-4-carboxylic acid (2-chloro-benzothiazol-6-yl)-amide (0.056 g, 0.146 mmol) to a mixture of N,N'-dimethyl-N-quinolin-2-yl-propane-1,3-diamine (0.100 g, 0.436 mmol) and anhydrous toluene (0.5 mL) in a sealed tube. Purge the mixture with dry nitrogen and seal the tube. Immerse the tube into a pre-heated (150° C.) oil bath and stir for 1.5 h. Cool the mixture to room temperature. Subject the mixture to silica gel flash column chromatography (5% MeOH/CH₂Cl₂) and then concentrate to a residue. Triturate the residue with MeOH to yield the desired product (0.046 mg, 55%). mass spectrum (m/e): 576.0 (M+1), 574.0 (M−1). ¹H NMR (400 MHz, DMSO-d6): 10.28 (s, 1H), 8.23 (d, J=2.0 Hz, 1H), 8.06 (d, J=8.4 Hz, 2H), 8.00 (d, J =8.8 Hz, 1H), 7.84-7.79 (m, 4H), 7.66 (d, J=8.0 Hz, 1H), 7.58-7.46 (m, 3H), 7.41 (d, J=8.8 Hz, 1H), 7.37-7.30 (m, 2H), 7.18-7.14 (m, 1H), 7.09 (d, J=9.2 Hz, 1H), 3.73 (t, J=2.4 Hz, 2H), 3.61 (t, J=6.8 Hz, 2H), 3.17 (s, 3H), 3.16 (s, 3H), 2.05-1.95 (m, 2H).

Example 32

Rac-4-Cyclohexyl-N-{2-[methyl-(1-methyl-pyrrolidin-3-ylmethyl)-amino]-benzooxazol-5-yl}-benzamide Step 1. 2-Ethylsulfanyl-5-nitrobenzooxazole

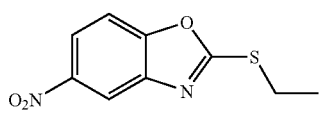

Dissolve 5-nitro-3H-benzooxazole-2-thione (10.58 g, 53.9 mmol) in anhydrous THF (300 mL). Cool the mixture to 0° C. in an ice bath. Add NaH (4.90 g, 60% dispersion in mineral oil) slowly. Stir the resulting mixture at 0° C. for 10 min. Add iodoethane (20.0 mL, 0.250 mmol) to the stirring mixture.

Step 2. Rac-Methyl-(1-methyl-pyrrolidin-3-ylmethyl)-5-nitro-benzooxazol-2-yl)-amine

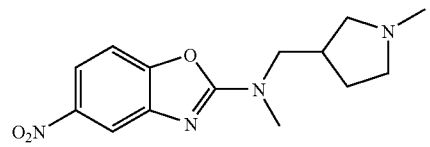

Dissolve 2-ethylsulfanyl-5-nitro-benzooxazole (1.78 g, 7.95 mmol) in anhydrous THF (10 mL) in a reaction tube and blow nitrogen into the vessel for 10 s. Add Rac-methyl-(1-methyl-pyrrolidin-3-ylmethyl)-amine (1.53 g, 11.93 mmol) to the solution. Quickly seal the vessel and immerse into a pre-heated oil bath (80° C.) and stir for 24 h. Concentrate the reaction mixture in vacuo, wash with 1.0M NaOH (2×50 mL), dry over Na₂SO₄, filter, and concentrate in vacuo. Subject the residue to silica gel flash column chromatography (120 g column, eluting with 2N NH₃ in MeOH/CH₂Cl₂) to yield the desired product (0.720 g, 31%). mass spectrum (mie): 291.3 (M+1).

Step 3. Rac-N²-Methyl-N²-(1-methyl-pyrrolidin-3-ylmethyl)-benzooxazole-2,5-diamine

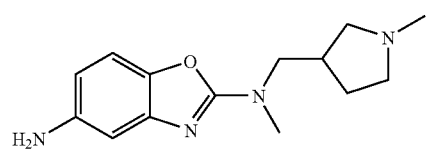

Dissolve rac-methyl-(1-methyl-pyrrolidin-3-ylmethyl)-(5-nitro-benzooxazol-2-yl)-amine (1.48 g, 5.09 mmol) in acetic acid (90 mL) and add Fe (1.42 g, 25.4 mmol) to the solution. Stir the mixture at 40° C. for 3 h. Filter the reaction mixture through Celite® and wash with H₂O/MeOH. Concentrate the reaction mixture in vacuo. Subject the residue to silica gel flash column chromatography (120 g column, 10% 2N NH₃ in MeOH/CH₂Cl₂) to yield the desired product (0.913 g, 69%). mass spectrum (m/e): 261.2 (M+1).

Step 4. 4-Cyclohexyl-N-{2-[methyl-(1-methyl-pyrrolidin-3-ylmethyl)-amino]-benzooxazol-5-yl}-benzamide

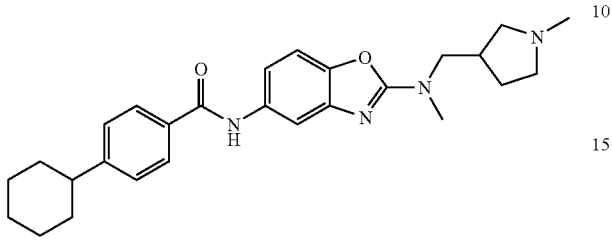

Combine rac-$N^2$-methyl-$N^2$-(1-methyl-pyrrolidin-3-ylmethyl)-benzooxazole-2,5-diamine (0.040 g, 0.154 mmol), 4-cyclohexylbenzoic acid (0.047 g, 0.230 mmol), HATU (0.058 g, 0.154 mmol), polystyrene-bound diisopropylamine (0.385 g, loading: 2.0 to 3.5 mmol/g), and CH₂Cl₂ (20 mL). Shake the mixture overnight at room temperature. Filter the mixture and wash the polystyrene resin with 1:1 CH₂Cl₂/MeOH. Subject the mixture to flash column chromatography (12 g column, eluting with 10% 2M NH₃ in MeOH/CH₂Cl₂) to yield a colorless oil. The oil was dissolved in CH₂Cl₂ and hexane added. The mixture was concentrated and dried under high vacuum to yield the desired product as a white solid (0.034 g, 50%). mass spectrum (m/e): 447.3 (M+1). ¹H NMR (400 MHz, CD₃OD): δ 7.89-7.85 (m, 2H), 7.71 (d, J=2.0 Hz, 1H), 7.39-7.28 (m, 4H), 3.59 (m, 2H), 3.23 (s, 3H), 2.83-2.58 (m, 6H), 2.39 (s, 3H), 2.13-2.01 (m, 1H), 1.94-1.84 (m, 4H), 1.83-1.76 (m, 1H), 1.67-1.57 (m, 1H), 1.57-1.41 (m, 4H), 1.40-1.28 (m, 1H).

Example 33

Rac-N-{2-[Methyl-(1-methyl-pyrrolidin-3-ylmethyl)-amino]-benzooxazol-5-yl}-3-(4-trifluoromethyl-phenyl)-acrylamide

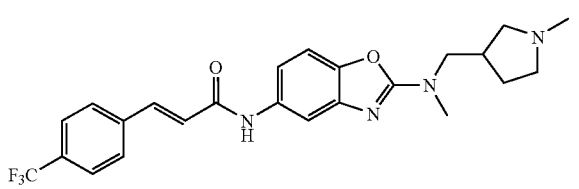

Combine rac-$N^2$-methyl-$N^2$-(1-methyl-pyrrolidin-3-ylmethyl)-benzooxazole-2,5-diamine (0.040 g, 0.154 mmol), 3-(4-trifluoromethyl-phenyl)-acrylic acid (0.050 g, 0.230 mmol), HATU (0.058 g, 0.154 mmol), polystyrene-bound diisopropylamine (0.385 g, loading: 2.0 to 3.5 mmol/g), and CH₂Cl₂ (20 mL). Shake the mixture overnight at room temperature. Filter the mixture and wash the polystyrene resin with 1:1 CH₂Cl₂/MeOH. Subject the mixture to flash column chromatography (12 g column, eluting with 10% 2M NH₃ in MeOH/CH₂Cl₂) to yield the product as a yellow-white solid (0.040 g, 57%). mass spectrum (m/e): 459.0 (M+1), 457.0 (M−1). ¹H NMR (400 MHz, CDCl₃): δ 7.75 (d, J=15.2 Hz, 1H), 7.61 (m, 4H), 7.53 (d, J=12.4 Hz, 2H), 7.37 (d, J=8.0 Hz, 1H), 7.20 (d, J=8.0 Hz, 1H), 6.64 (d, J=15.6 Hz, 1H), 3.62-3.49 (m, 2H), 3.20 (s, 3H), 2.77-2.55 (m, 4H), 2.44-2.37 (m, 1H), 2.38 (s, 3H), 2.09-1.98 (m, 1H), 1.63-1.53 (m, 1H).

Example 34

4'-Fluoro-biphenyl-4-carboxylic acid {2-[methyl-(1-methyl-pyrrolidin-3-ylmethyl)-amino]-benzooxazol-5-yl}-amide; Isomer 2

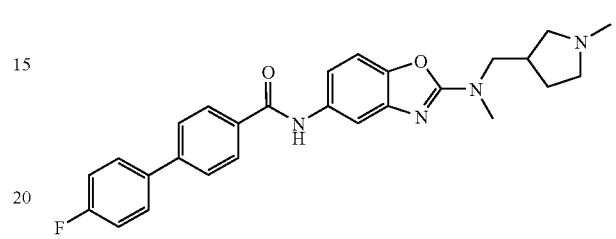

Combine rac-$N^2$-methyl-$N^2$-(1-methyl-pyrrolidin-3-ylmethyl)-benzooxazole-2,5-diamine (0.700 g, 2.69 mmol), 4'-fluoro-biphenyl-4-carboxylic acid (0.872 g, 4.03 mmol), HATU (1.43 g, 3.76 mmol), polystyrene-bound diisopropylamine (7.53 g, loading: 2.0 to 3.5 mmol/g), and CH₂Cl₂ (15 mL). Shake the mixture overnight at room temperature. Filter the mixture and wash the polystyrene resin with 1:1 CH₂Cl₂/MeOH. Subject the mixture to flash column chromatography on an ISCO Companion (120 g column, eluting with 20% 2M NH₃ in MeOH/CH₂Cl₂) to yield a mixture of products. Subject the mixture to flash column chromatography (3×40 g, eluting with 20% 2M NH₃ in MeOH/CH₂Cl₂) to yield a mixture of products. Concentrate the fractions and suspend the residue in anhydrous diethyl ether. Stir at room temperature for 3 d. Filter the mixture to yield the product as a white solid (0.375 g, 30%). Submit the racemic mixture to chiral chromatography to yield the product (0.187 g) as the second eluting enantiomer; mass spectrum (m/e): 459.2 (M+1), 457.3 (M−1). ¹H NMR (400 MHz, DMSO-d6): δ 10.22 (s, 1H), 8.07-8.03 (m, 2H), 7.85-7.79 (m, 4H), 7.73 (d, J=2.0 Hz, 1H), 7.40-7.31 (m, 4H), 3.50 (d, J=7.6 Hz, 2H), 3.13 (s, 3H), 2.65-2.56 (m, 1H), 2.54-2.47 (m, 2H), 2.43-2.36 (m, 1H), 2.29-2.24 (m, 1H), 2.23 (s, 3H), 1.93-1.84 (m, 1H), 1.49-1.40 (m, 1H).

Example 35

4'-Fluoro-biphenyl-4-carboxylic acid {2-[methyl-(1-methyl-pyrrolidin-3-ylmethyl)-amino]-benzooxazol-5-yl}-amide. Isomer 1

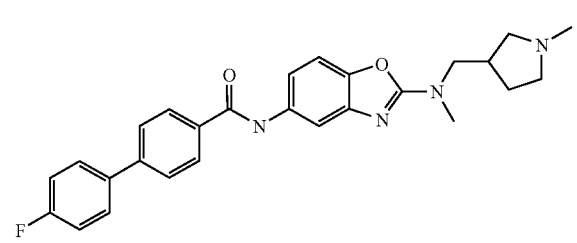

The title compound is prepared according to Example 34, yielding the first eluting isomer (0.188 g). mass spectrum (m/e): 459.2 (M+1), 457.3 (M−1). $^1$H NMR (400 MHz, DMSO-d6): δ 10.22 (s, 1H), 8.07-8.03 (m, 2H), 7.85-7.79 (m, 4H), 7.73 (d, J=2.0 Hz, 1H), 7.40-7.31 (m, 4H), 3.50 (d, J=7.6 Hz, 2H), 3.13 (s, 3H), 2.65-2.56 (m, 1H), 2.54-2.47 (m, 2H), 2.43-2.36 (m, 1H), 2.29-2.24 (m, 1H), 2.23 (s, 3H), 1.93-1.84 (m, 1H), 1.49-1.40 (m, 1H).

Example 36

Rac-2',4'-Dichloro-biphenyl-4-carboxylic acid {2-[methyl-(1-methyl-pyrrolidin-3-ylmethyl)-amino]-benzooxazol-5-yl}-amide

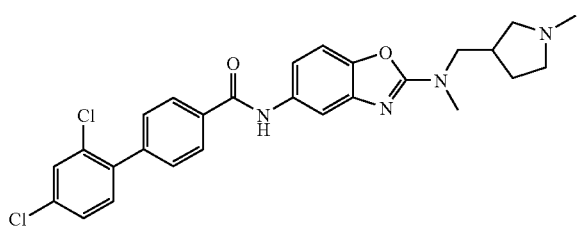

Combine rac-N$^2$-methyl-N$^2$-(1-methyl-pyrrolidin-3-ylmethyl)-benzooxazole-2,5-diamine (0.040 g, 0.154 mmol), 2',4'-dichloro-biphenyl-4-carboxylic acid (0.062 g, 0.230 mmol), HATU (0.058 g, 0.154 mmol), polystyrene-bound diisopropylamine (0.385 g, loading: 2.0 to 3.5 mmol/g), and CH$_2$Cl$_2$ (10 mL). Shake the mixture overnight at room temperature. Filter the mixture and wash the polystyrene resin with 1:1 CH$_2$Cl$_2$/MeOH. Subject the mixture to flash column chromatography on an ISCO Companion (12 g column, eluting with 10% 2M NH$_3$ in MeOH/CH$_2$Cl$_2$) to yield a colorless oil (0.036 g). Dissolve the oil in CH$_2$Cl$_2$, wash with 1.0M NaOH (3×25 mL), dry over Na$_2$SO$_4$, filter, concentrate in vacuo, and pump overnight on high vacuum to yield the desired product (0.031 g, 40%). mass spectrum (m/e): 509.0 (M+1), 507.0 (M−1). $^1$H NMR (400 MHz, DMSO-d6) δ 10.28 (s, 1H), 8.03 (d, J=8.8 Hz, 2H), 7.80-7.78 (m, 1H), 7.73-7.71 (m, 1H), 7.61-7.48 (m, 4H), 7.40-7.33 (m, 2H), 3.50 (d, J=8.0 Hz, 1H), 3.13 (s, 3H), 2.65-2.55 (m, 1H), 2.44-2.34 (m, 2H), 2.28-2.21 (m, 1H), 2.23 (s, 3H), 1.93-1.83 (m, 2H), 1.49-1.39 (m, 2H).

Example 37

N-{2-[Methyl-(1-methyl-pyrrolidin-3-ylmethyl)-amino]-benzooxazol-5-yl}-3-phenoxy-benzamide

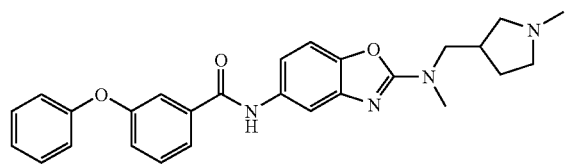

Combine rac-N$^2$-methyl-N$^2$-(1-methyl-pyrrolidin-3-ylmethyl)-benzooxazole-2,5-diamine (0.034 g, 0.131 mmol), 3-phenoxy-benzoic acid (0.042 g, 0.196 mmol), HATU (0.050 g, 0.131 mmol), polystyrene-bound diisopropylamine (0.327 g, loading: 2.0 to 3.5 mmol/g), and CH$_2$Cl$_2$ (10 mL). Shake the mixture overnight at room temperature. Filter the mixture and wash the polystyrene resin with 1:1 CH$_2$Cl$_2$/MeOH. Concentrate the solution to yield a yellow residue. Dilute with CH$_2$Cl$_2$ and wash with 1.0M NaOH (2×25 mL), dry over Na$_2$SO$_4$, filter, and concentrate in vacuo after adsorption onto silica gel. Subject the mixture to flash column chromatography on an ISCO Companion (4 g column, 10% 2M NH$_3$ in MeOH/CH$_2$Cl$_2$) to yield the desired compound as a white oil. Dilute with CH$_2$Cl$_2$ and n-hexane and concentrate in vacuo. Pump for 2 h to yield the desired compound as a white solid (0.027 g, 45%). mass spectrum (m/e): 457.3 (M+1), 455.3 (M−1). $^1$H NMR (400 MHz, CDCl$_3$): δ 7.84 (s, 1H), 7.56 (d, J=7.6 Hz, 1H), 7.51-7.45 (m, 2H), 7.41 (t, J=8.0 Hz, 1H), 7.37-7.29 (m, 3H), 7.20-7.10 (m, 3H), 7.04-7.00 (m, 2H), 3.59-3.48 (m, 2H), 3.18 (s, 3H), 2.74-2.50 (m, 4H), 2.38-2.33 (m, 1H), 2.35 (s, 3H), 2.05-1.95 (m, 1H), 1.59-1.49 (m, 1H).

Example 38

N-{2-[Methyl-(1-methyl-pyrrolidin-3-ylmethyl)-amino]-benzooxazol-5-yl}-4-phenoxy-benzamide

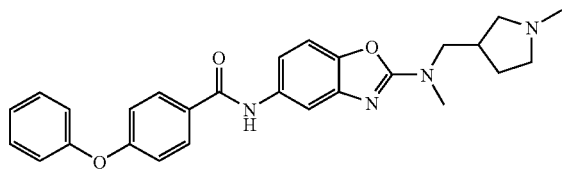

Combine rac-N$^2$-methyl-N$^2$-(1-methyl-pyrrolidin-3-ylmethyl)-benzooxazole-2,5-diamine (0.034 g, 0.131 mmol), 4-phenoxy-benzoic acid (0.042 g, 0.196 mmol), HATU (0.050 g, 0.131 mmol), polystyrene-bound diisopropylamine (0.327 g, loading: 2.0 to 3.5 mmol/g), and CH$_2$Cl$_2$ (10 mL). Shake the mixture overnight at room temperature. Filter the mixture and wash the polystyrene resin with 1:1 CH$_2$Cl$_2$/MeOH. Concentrate the solution in vacuo. Dilute with CH$_2$Cl$_2$, wash with 1.0M NaOH (2×25 mL), dry over Na$_2$SO$_4$, filter, and concentrate in vacuo. Subject the residue to silica gel flash column chromatography on an ISCO Companion (4 g column, eluting with 10% 2N NH$_3$ in MeOH/CH$_2$Cl$_2$) to yield the desired product as a white oil. Dissolve in CH$_2$Cl$_2$ and add n-hexane. Re-concentrate to yield the desired product as a white solid (0.031 g, 52%). mass spectrum (m/e): 457.3 (M+1), 455.3 (M−1). $^1$H NMR (400 MHz, DMSO-d6): δ 10.12 (s, 1H), 8.01-7.99 (m, 2H), 7.70-7.68 (m, 1H), 7.49-7.42 (m, 2H), 7.35-7.32 (m, 2H), 7.25-7.20 (m, 1H), 7.13-7.07 (m, 4H), 3.52-3.47 (d, J=8.0 Hz, 2H), 3.12 (s, 3H), 2.66-2.55 (m, 1H), 2.55-2.47 (m, 2H), 2.43-2.35 (m, 1H), 2.55-2.47 (m, 2H), 2.43-2.35 (m, 1H), 2.28-2.24 (m, 1H), 2.23 (s, 3H), 1.93-1.83 (m, 1H), 1.49-1.39 (m, 1H).

Example 39

Rac-6-(4-Fluoro-phenyl)-N-{2-[methyl-(1-methyl-pyrrolidin-3-ylmethyl)-amino]-benzooxazol-5-yl}-nicotinamide

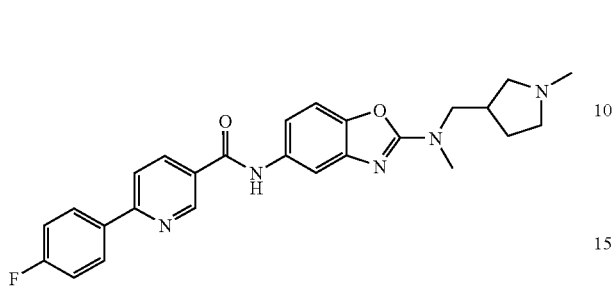

Combine rac-$N^2$-Methyl-$N^2$-(1-methyl-pyrrolidin-3-ylmethyl)-benzooxazole-2,5-diamine (0.034 g, 0.131 mmol), 6-(4-fluoro-phenyl)-nicotinic acid (0.043 g, 0.198 mmol), HATU (0.050 g, 0.131 mmol), polystyrene-bound diisopropylamine (0.327 g, loading: 2.0 to 3.5 mmol/g), and $CH_2Cl_2$ (10 mL). Shake the mixture overnight at room temperature. Filter the mixture and wash the polystyrene resin with 1:1 $CH_2Cl_2$/MeOH. Concentrate the solution in vacuo. Dilute with $CH_2Cl_2$, wash with 1.0M NaOH (2×25 mL), dry over $Na_2SO_4$, filter, and concentrate in vacuo. Subject the residue to silica gel flash column chromatography (4 g column, eluting with 10% 2N $NH_3$ in MeOH/$CH_2Cl_2$) to yield the desired product as an impure mixture. Re-subject the mixture to silica gel flash column chromatography (3×4 g columns, 5% 2N $NH_3$ in MeOH/$CH_2Cl_2$) to yield the desired product as a white oil (0.030 g, 51%). mass spectrum (m/e): 460.0 (M+1), 458.0 (M−1). $^1$H NMR (400 MHz, CDCl$_3$): δ 9.10 (s, 1H), 8.31 (s, 1H), 8.22 (dd, J=8.0, 2.4 Hz, 1H), 8.03-7.97 (m, 2H), 7.72 (d, J=8.4 Hz, 1H), 7.53 (s, 1H), 7.34 (d, J=8.4 Hz, 1H), 7.20-7.11 (m, 3H), 3.58-3.46 (m, 2H), 3.16 (s, 3H), 2.72-2.56 (m, 3H), 2.55-2.48 (m, 1H), 2.38-2.32 (m, 1H), 2.33 (s, 3H), 2.04-1.95 (m, 1H), 1.57-1.48 (m, 1H).

Example 40

4'-Fluoro-biphenyl-4-carboxylic acid {2-[methyl-(1-methyl-piperidin-4-yl)-amino]-benzooxazol-5-yl}-amide Step 1. Methyl-(1-methyl-piperidin-4-yl)-(5-nitro-benzooxazol-2-yl)-amine

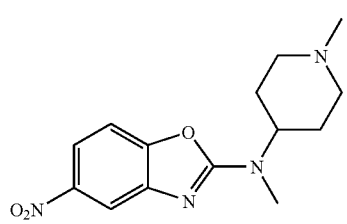

The title compound is prepared according to the procedure described in General Method A, using 2-ethylsulfanyl-5-nitrobenzooxazole (1.17 g, 5.23 mmol) and methyl-(1-methyl-piperidin-4-yl)-amine (1.37 mL, 9.42 mmol) in anhydrous THF (10 mL) at 100° C.: (0.608 g, 40%). mass spectrum (m/e): 291.0 (M+1).

Step 2. $N^2$-Methyl-$N^2$-(1-methyl-piperidin-4-yl)-benzooxazole-2,5-diamine

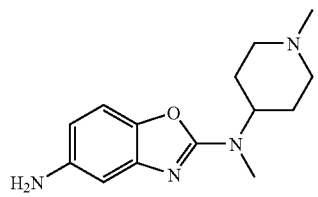

The title compound was prepared according to the procedure described in General Method B, using methyl-(1-methyl-piperidin-4-yl)-(5-nitro-benzooxazol-2-yl)-amine (0.583 g, 2.01 mmol), acetic acid (8 mL), and iron (1.12 g, 20.1 mmol) to provide product (0.474 g, 91%). mass spectrum (m/e): 261.2 (M+1).

Step 3. 4'-Fluoro-biphenyl-4-carboxylic acid {2-[methyl-(1-methyl-piperidin-4-yl)-amino]-benzooxazol-5-yl}-amide Add oxalyl chloride (0.16 mL, 1.82 mmol) and 3 drops of DMF to a stirring suspension of 4'-fluoro-biphenyl-4-carboxylic acid (0.197 g, 0.910 mmol) in $CH_2Cl_2$ (2.0 mL). Stir the reaction mixture at room temperature for 2 h, Concentrate the mixture in vacuo, add n-hexane, re-concentrate, and re-dissolve in $CH_2Cl_2$. Add the resultant 4'-fluoro-biphenyl-4-carbonyl chloride solution to a mixture of rac-$N^2$-methyl-$N^2$-(1-methyl-piperidin-4-yl)-benzooxazole-2,5-diamine (0.158 g, 0.607 mmol) and pyridine (0.05 mL) in $CH_2Cl_2$ (10 mL). Shake the reaction mixture overnight at room temperature. Wash the mixture with saturated $NaHCO_3$ (2×20 mL), dry the organic phase over $Na_2SO_4$, filter, and concentrate the mixture in vacuo. Subject the residue to silica gel flash column chromatography (3×4 g columns, eluting with 5% 2N $NH_3$ in MeOH/$CH_2Cl_2$) to yield the desired product as a white solid (0.106 g, 38%). mass spectrum (m/e): 459.0 (M+1), 457.0 (M−1). $^1$H NMR (400 MHz, CDCl$_3$): δ 7.95-7.90 (m, 3H), 7.63 (d, J=8.0 Hz, 2H), 7.60-7.54 (m, 2H), 7.52 (d, J=1.2 Hz, 1H), 7.36 (dd, J=8.8, 1.6 Hz, 1H), 7.21 (d, J=8.0 Hz, 1H), 7.18-7.11 (m, 2H), 4.21-4.11 (m, 1H), 3.07 (s, 3H), 2.97 (d, J=11.6 Hz, 2H), 2.32 (s, 3B), 2.21-2.12 (m, 2H), 2.00-1.88 (m, 2H), 1.83-1.75 (m, 2H).

Example 41

4-Cyclohexyl-N-{2-[methyl-(1-methyl-piperidin-4-yl)-amino]-benzooxazol-5-yl}-benzamide

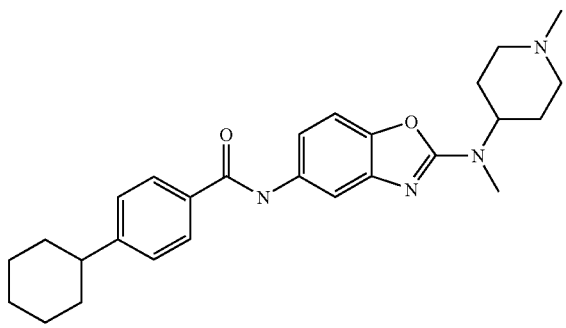

Add oxalyl chloride (0.16 mL, 1.82 mmol) and 3 drops of DMF to a stirring suspension of 4-cyclohexyl-benzoic acid (0.197 g, 0.910 mmol) in CH$_2$Cl$_2$ (2.0 mL). Stir the reaction mixture at room temperature for 2 h. Concentrate the mixture in vacuo, add n-hexane, re-concentrate, and re-dissolve in CH$_2$Cl$_2$. Add the resultant 4-cyclohexyl-benzoyl chloride solution to a mixture of rac-N$^2$-methyl-N$^2$-(1-methyl-piperidin-4-yl)-benzooxazole-2,5-diamine (0.158 g, 0.607 mmol) and pyridine (0.05 mL) in CH$_2$Cl$_2$ (10 mL). Shake the reaction mixture overnight at room temperature. Wash the mixture with saturated NaHCO$_3$ (aqueous) (2×20 mL), dry the organic phase over Na$_2$SO$_4$, filter, and concentrate the mixture in vacuo. Subject the residue to silica gel flash column chromatography (3×4 g columns, eluting with 5% 2N NH$_3$ in MeOH/CH$_2$Cl$_2$) to yield the desired product as a white solid (0.169 g, 62%). mass spectrum (m/e): 447.3 (M+1). $^1$H NMR (400 MHz, CDCl$_3$): δ 7.85 (s, 1H), 7.78 (d, J=8.4 Hz, 2H), 7.47 (d, J=2.0 Hz, 1H), 7.35 (dd, J=8.8, 2.0 Hz, 1H), 7.31-7.27 (m, 2H), 7.19 (d, J=8.8 Hz, 1H), 4.19-4.10 (m, 1H), 3.06 (s, 3H), 2.96 (d, J=12.0 Hz, 2H), 2.66-2.50 (m, 1H), 2.31 (s, 3H), 2.15 (dt, J=11.6, 2.4 Hz, 2H), 1.98-1.71 (m, 10H), 1.48-1.33 (m, 3H), 1.31-1.19 (m, 1H).

Example 42

4-Butyl-N-{2-[methyl-(1-methyl-piperidin-4-yl)-amino]-benzooxazol-5-yl}-benzamide

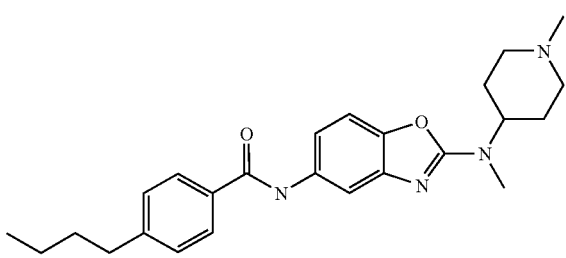

Add oxalyl chloride (0.16 mL, 1.82 mmol) and 3 drops of DMF to a stirring suspension of 4-butyl-benzoic acid (0.162 g, 0.910 mmol) in CH$_2$Cl$_2$ (2.0 mL). Stir the reaction mixture at room temperature for 2 h. Concentrate the mixture in vacuo, add n-hexane, re-concentrate, and re-dissolve in CH$_2$Cl$_2$. Add the resultant 4-butyl-benzoyl chloride solution to a mixture of rac-N$^2$-methyl-N$^2$-(1-methyl-piperidin-4-yl)-benzooxazole-2,5-diamine (0.158 g, 0.607 mmol) and pyridine (0.05 mL) in CH$_2$Cl$_2$ (10 mL). Shake the reaction mixture overnight at room temperature. Wash the mixture with saturated NaHCO$_3$ (aq) (2×20 mL), dry the organic phase over Na$_2$SO$_4$, filter, and concentrate the mixture in vacuo. Subject the residue to silica gel flash column chromatography (3×4 g columns, eluting with 5% 2N NH$_3$ in MeOH/CH$_2$Cl$_2$) to yield the desired product as an oil (0.098 g, 35%). mass spectrum (m/e): 421.0 (M+1). $^1$H NMR (400 MHz, CDCl$_3$): δ 7.84-7.78 (m, 1H), 7.78 (d, J=8.0 Hz, 2H), 7.48 (d, J=1.9 Hz, 1H), 7.35 (dd, J 8.8, 1.8 Hz, 1H), 7.27 (d, J=8.0 Hz, 1H), 7.20 (d, J=8.8 Hz, 1H), 4.21-4.11 (m, 1H), 3.07 (s, 3H), 2.97 (d, J=11.2 Hz, 2H), 2.66 (t, J=8.0 Hz, 2H), 2.32 (s, 3H), 2.17 (t, J=11.6 Hz, 2H), 2.01-1.87 (m, 2H), 1.83-1.75 (m, 2H), 1.65-1.56 (m, 2H), 1.40-1.30 (m, 2H), 0.92 (t, J=7.2 Hz, 3H).

Example 43

4-Cyclohexyl-N-{2-[methyl-(1-methyl-pyrrolidin-3-ylmethyl)-amino]-benzooxazol-5-yl}-benzamide; Isomer 1

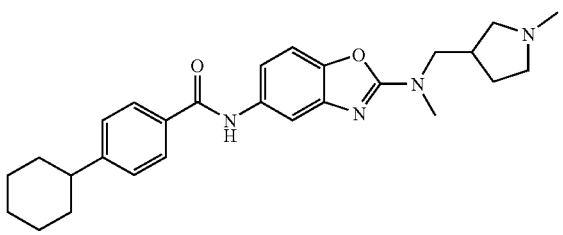

Combine rac-N$^2$-methyl-N$^2$-(1-methyl-pyrrolidin-3-ylmethyl)-benzooxazole-2,5-diamine (0.150 g, 0.576 mmol), 4-cyclohexyl-benzoic acid (0.177 g, 0.864 mmol), HATU (0.219 g, 0.576 mmol), polystyrene-bound diisopropylamine (1.44 g, loading: 2.0 to 3.5 mmol/g), and CH$_2$Cl$_2$ (20 mL). Shake the mixture overnight at room temperature. Add HATU (0.219 g, 0.576 mmol) and shake for 21 h at room temperature. Dilute with 1:1 CH$_2$Cl$_2$/MeOH, wash with 10M NaOH (equal volume), dry over Na$_2$SO$_4$, filter, and concentrate in vacuo. Subject the mixture to silica gel flash column chromatography (2×12 g columns, 5% 2M NH$_3$ in MeOH/CH$_2$Cl$_2$, then ramping to 10% after 10 min) to yield the desired product as a colorless oil (0.103 g, 40%). Subject the product to chiral preparative chromatography [Chiralpak AD-H column, (8×32 cm), eluting with 70/30 3 Å ethanol/ACN w/0.2% dimethylethylamine; Flow rate=350 mL/min] to yield isomer 1 (0.039 g). mass spectrum (m/e): 447.3 (M+1). $^1$H NMR (400 MHz, CDCl$_3$): δ 7.83 (s, 1H), 7.80-7.76 (m, 2H), 7.48 (d, J=2.0 Hz, 1H), 7.35 (dd, J=8.6, 1.8 Hz, 1H), 7.31-7.27 (m, 2H), 7.20 (d, J=8.4 Hz, 1H), 3.61-3.46 (m, 2H), 3.19 (s, 3H), 2.77-2.51 (m, 6H), 2.42-2.37 (m, 1H), 2.37 (s, 3H), 2.07-1.97 (m, 1H), 1.91-1.80 (m, 4H), 1.76 (d, J=12.8 Hz, 1H), 1.61-1.52 (m, 1H), 1.48-1.22 (m, 4H).

Example 44

4-Cyclohexyl-N-{2-[methyl-(1-methyl-pyrrolidin-3-ylmethyl)-amino]-benzooxazol-5-yl}-benzamide; Isomer 2

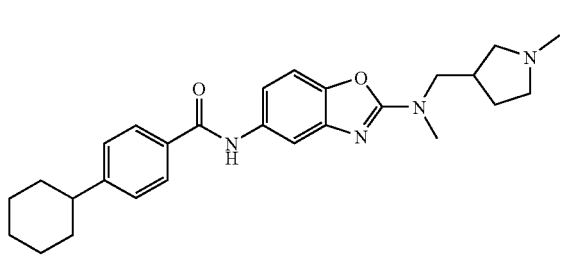

The title compound is prepared according to Example 43. Chiral preparative chromatography yielded the second eluting enantiomer (0.040 g). mass spectrum (m/e): 447.3 (M+1). $^1$H NMR (400 MHz, CDCl$_3$): δ 7.83 (s, 1H), 7.80-7.76 (m, 2H), 7.48 (d, J=2.0 Hz, 1H), 7.35 (dd, J=8.6, 1.8 Hz, 1H), 7.31-7.27 (m, 2H), 7.20 (d, J=8.4 Hz, 1H), 3.61-3.46 (m, 2H), 3.19 (s, 3H), 2.77-2.51 (m, 6H), 2.42-2.37 (m, 1H), 2.37 (s, 3H), 2.07-1.97 (m, 1H), 1.91-1.80 (m, 4H), 1.76 (d, J=12.8 Hz, 1H), 1.61-1.52 (m, 1H), 1.48-1.22 (m, 4H).

Example 45

N-{2-[Methyl-(1-methyl-pyrrolidin-3-ylmethyl)-amino]-benzooxazol-5-yl}-3-(4-trifluoromethyl-phenyl)-acrylamide

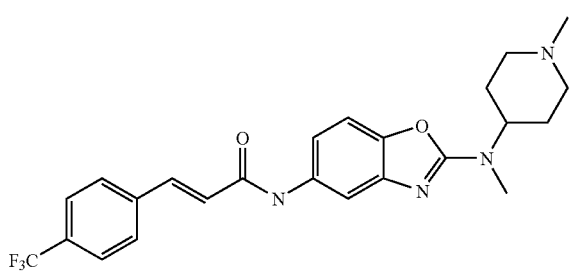

Add oxalyl chloride (0.20 mL, 2.30 mmol) and 3 drops of DMF to a stirring suspension of 3-(4-trifluoromethyl-phenyl)-acrylic acid (0.249 g, 1.15 mmol) in CH$_2$Cl$_2$ (5.0 mL). Stir the reaction mixture at room temperature for 2 h. Concentrate the mixture in vacuo, add n-hexane, re-concentrate, and re-dissolve in CH$_2$Cl$_2$. Add the resultant 3-(4-trifluoromethyl-phenyl)-acryloyl chloride solution to a mixture of rac-N$^2$-methyl-N$^2$-(1-methyl-piperidin-4-yl)-benzooxazole-2,5-diamine (0.158 g, 0.607 mmol) and pyridine (0.06 mL) in CH$_2$Cl$_2$ (5.0 mL). Shake the reaction mixture overnight at room temperature. Filter the reaction mixture and wash the product with CH$_2$Cl$_2$. Dry the product on high vacuum to yield the desired product as an off-white solid (0.321 g, 91%). mass spectrum (m/e): 459.0 (M+1), 457.0 (M−1). $^1$H NMR (400 MHz, CD$_3$OD): δ 8.93-8.89 (m, 1H), 8.71 (dt, J=8.0, 1.8 Hz, 1H), 8.17-8.13 (m, 1H), 7.85-7.72 (m, 4H), 7.55 (d, J=8.8 Hz, 1H), 7.44 (dd, J=8.8, 1.8 Hz, 1H), 6.94 (d, J=15.8 Hz, 1H), 4.57-4.47 (m, 1H), 3.75-3.67 (m, 2H), 3.36-3.29 (m, 2H), 3.28 (s, 3H), 2.96 (s, 3H), 2.41-2.28 (m, 2H), 2.27-2.18 (m, 2H).

Example 46

N-{2-[Methyl-(1-methyl-piperidin-4-yl)-amino]-benzooxazol-5-yl}-3-phenoxy-benzamide

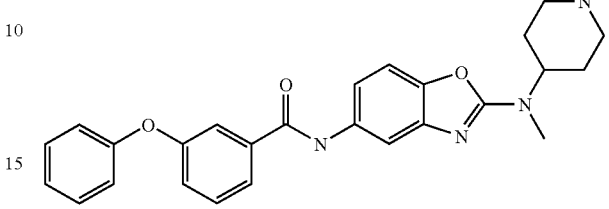

Add oxalyl chloride (0.20 mL, 2.30 mmol) and 3 drops of DMF to a stirring suspension of 3-phenoxy-benzoic acid (0.247 g, 1.15 mmol) in CH$_2$Cl$_2$ (5.0 mL). Stir the reaction mixture at room temperature for 2 h. Concentrate the mixture in vacuo, add n-hexane, re-concentrate, and re-dissolve in CH$_2$Cl$_2$. Add the resultant 3-phenoxy-benzoyl chloride solution to a mixture of rac-N$^2$-methyl-N$^2$-(1-methyl-piperidin-4-yl)-benzooxazole-2,5-diamine (0.200 g, 0.768 mmol) and pyridine (0.06 mL) in CH$_2$Cl$_2$ (5.0 mL). Shake the reaction mixture overnight at room temperature. Wash the mixture with saturated NaHCO$_3$ (aqueous) (3×25 mL), dry the organic phase over Na$_2$SO$_4$, filter, and concentrate the mixture in vacuo. Subject the residue to silica gel flash column chromatography (5×4 g columns, eluting with 5% 2N NH$_3$ in MeOH/CH$_2$Cl$_2$) to yield the desired product as a white solid (0.163 g, 46%). mass spectrum (m/e): 457.0 (M+1), 455.0 (M−1). $^1$H NMR (400 MHz, CD$_3$OD): δ 7.72-7.67 (m, 2H), 7.60-7.57 (m, 1H), 7.51 (t, J=7.9 Hz, 1H), 7.44-7.38 (m, 2H), 7.35-7.28 (m, 2H), 7.22-7.15 (m, 2H), 7.09-7.05 (m, 2H), 4.18-4.09 (m, 1H), 3.12 (s, 3H), 3.06-3.00 (m, 2H), 2.35 (s, 3H), 2.24 (dt, J=12.4, 2.4 Hz, 2H), 2.03-1.92 (m, 2H), 1.87-1.80 (m, 2H).

Example 47

Biphenyl-4-carboxylic acid {2-[methyl-(1-methyl-piperidin-4-yl)-amino]-benzooxazol-5-yl}-amide

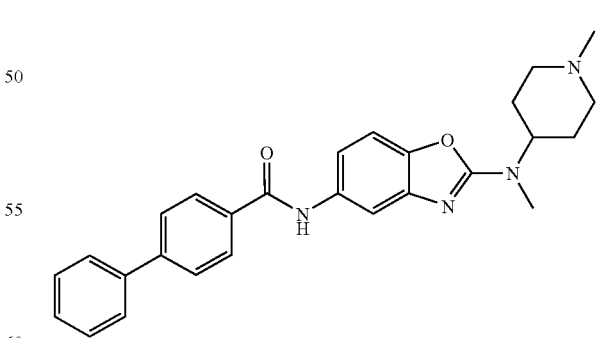

Add oxalyl chloride (0.20 mL, 2.30 mmol) and 3 drops of DMF to a stirring suspension of Biphenyl-4-carboxylic acid (0.240 g, 1.15 mmol) in CH$_2$Cl$_2$ (5.0 mL). Stir the reaction mixture at room temperature for 2 h. Concentrate the mixture in vacuo, add n-hexane, re-concentrate, and re-dissolve in CH$_2$Cl$_2$. Add the resultant biphenyl-4-carbonyl chloride solution to a mixture of rac-N²-methyl-N²-(1-methyl-piperidin-4-yl)-benzooxazole-2,5-diamine (0.200 g, 0.768 mmol) and pyridine (0.06 mL) in CH₂Cl₂ (10 mL). Shake the reaction mixture overnight at room temperature. Wash the mixture with saturated NaHCO₃ (aqueous) (2×25 mL), dry the organic phase over Na₂SO₄, filter, and concentrate the mixture in vacuo. Subject the residue to silica gel 130 flash column chromatography (5×4 g columns, eluting with 5% 2N NH₃ in MeOH/CH₂Cl₂) to yield the desired product (0.168 g, 50%). mass spectrum (m/e): 441.3 (M+1). ¹H NMR (400 MHz, CD₃OD): δ 8.01-7.97 (m, 2H), 7.74-7.70 (m, 3H), 7.67-7.64 (m, 2H), 7.48-7.42 (m, 2H), 7.39-7.31 (m, 2H), 7.26 (d, J=8.4 Hz, 1H), 4.12-4.02 (m, 1H), 3.06 (s, 3H), 2.97 (d, J=12.0 Hz, 2H), 2.30 (s, 3H), 2.17 (dt, J=12.4, 2.8 Hz, 2H), 1.91 (dq, J=12.0, 4.0 Hz, 2H), 1.76 (d, J=12.6 Hz, 2H).

Example 48

4'-Fluoro-biphenyl-4-carboxylic acid (2-{[2-(acetyl-methyl-amino)-ethyl]-methyl-amino}-benzothiazol-6-yl)-amide Step 1. N,N'-Dimethyl-N-(6-nitro-benzothiazol-2-yl)-ethane-1,2-diamine

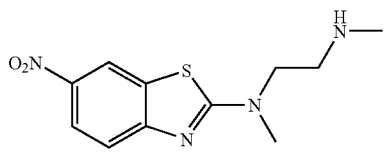

Dissolve 2-chloro-6-nitro-benzothiazole (2.20 g, 10.3 mmol) in THF (50 mL). Add N,N'-dimethyl-ethane-1,2-diamine (10.0 mL) and stir overnight at room temperature. Concentrate the reaction mixture in vacuo (adsorbing onto silica gel). Subject the mixture to silica gel flash column chromatography (120 g column, eluting with 10% 2N NH₃ in MeOH/CH₂Cl₂) to yield the desired product (0.500 g, 18%). mass spectrum (m/e): 267.3 (M+1).

Step 2. N-Methyl-N-{2-[methyl-(6-nitro-benzothiazol-2-yl)-amino]-ethyl}-acetamide

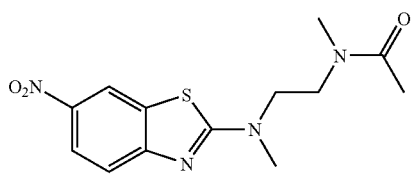

Dissolve N,N'-dimethyl-N-(6-nitro-benzothiazol-2-yl)-ethane-1,2-diamine (0.255 g, 0.957 mmol) in CH₂Cl₂ (10 mL) and add pyridine (0.1 mL, 1.2 mmol). Add acetyl chloride (0.102 mL, 1.43 mmol) and shake the mixture overnight at room temperature. Concentrate the reaction mixture in vacuo (adsorbing onto silica gel) and subject the mixture to silica gel flash column chromatography (40 g column, eluting with 1-10% MeOH/CH₂Cl₂) to yield the desired product (0.295 g, 100%). mass spectrum (m/e): 309.2 (M+1).

Step 3. N-{2-[(6-Amino-benzothiazol-2-yl)-methyl-amino]-ethyl}-N-methyl-acetamide

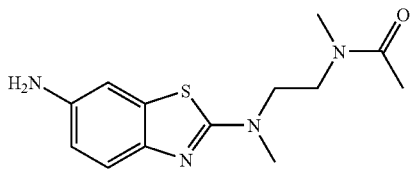

Shake a mixture of N-methyl-N-{2-[methyl-(6-nitro-benzothiazol-2-yl)-amino]-ethyl}-acetamide (0.30 g, mmol) and Pd/C (5%, 0.1515 g) in absolute ethanol (50 mL) and anhydrous THF (20 mL) under 60 psi H₂(g) at room temperature for 18 h. Filter the mixture and concentrate in vacuo. Residue re-subjected to hydrogenation using Pd/C (0.2101 g) in absolute ethanol (50 mL) and THF (10 mL) to yield the desired product (0.209 g). Adsorb onto silica gel and subject to silica gel flash column chromatography (12 g column, eluting with 1-5% MeOH/CH₂Cl₂). Adsorbed on a Silicycle cartridge (Si-Tosic Acid, 35 mL, 10 g) washing with MeOH and eluted with 2N NH₃ in MeOH. The product is 70% pure by LC-MS (0.146 g, %). mass spectrum (m/e): 279.0 (M+1). Used without further purification.

Step 4. 4'-Fluoro-biphenyl-4-carboxylic acid (2-{[2-(acetyl-methyl-amino)-ethyl]-methyl-amino}-benzothiazol-6-yl)-amide

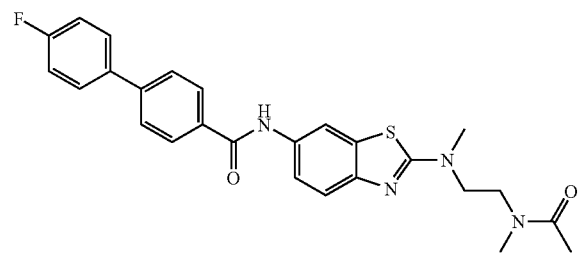

Add oxalyl chloride (0.20 mL, 2.30 mmol) and 4 drops of DMF to a stirring suspension of 4'-fluoro-biphenyl-4-carboxylic acid (0.243 g, 1.13 mmol) in CH₂Cl₂ (5.0 mL). Stir the reaction mixture at room temperature for 2 h. Concentrate the mixture in vacuo, add n-hexane, re-concentrate, and re-dissolve in CH₂Cl₂. Add the resultant 4'-fluoro-biphenyl-4-carbonyl chloride solution to a mixture of rac-N-{2-[(6-amino-benzothiazol-2-yl)-methyl-amino]-ethyl}-N-methyl-acetamide (0.146 g, 0.524 mmol) and pyridine (0.06 mL) in CH₂Cl₂ (10 mL). Shake the reaction mixture overnight at room temperature. Subject the residue to silica gel flash column chromatography (3×4 g columns, eluting with 5-10% ethyl acetate/n-hexane to remove impurities, then flushing off product with 2N NH₃/MeOH). Triturate the residue with CH₂Cl₂ to yield the desired product as a white solid (0.110 g, 44%). mass spectrum (m/e): 477.0 (M+1).

Example 49

4-Butyl-N-{2-[(2-dimethylamio-ethyl)-methyl-amino]-benzooxazol-5-yl}-benzamide; Hydrochloride Step 1. N,N,N'-Trimethyl-N'-(5-nitro-benzooxazol-2-yl)-ethane-1,2-diamine

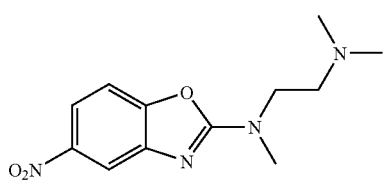

The title compound was prepared according to the procedure described in General Method A using 2-methylsulfanyl-5-nitro-benzooxazole (5.0 g, 23.8 mmol) and N,N,N'-Trimethyl-ethane-1,2-diamine (15.4 mL, 118.9 mmol) at 140° C. The product was purified by silica gel flash column chromatography (330 g column, eluting with 5% 2N $NH_3$ in MeOH/$CH_2Cl_2$) to yield the desired product (2.8 g, 44%). mass spectrum (m/e): 265.3 (M+1).

Step 2. $N^2$-(2-Dimethylamino-ethyl)-$N^2$-methyl-benzooxazole-2,5-diamine

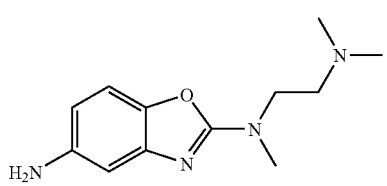

The title compound was prepared according to the procedure described in General Method B using N,N,N'-Trimethyl-N'-(5-nitro-benzooxazol-2-yl)-ethane-1,2-diamine (4.131 g, 15.63 mmol), acetic acid (50 mL), and Fe (8.72 g, 78.15 mmol), stirring for 3 h: (3.57 g, 98%). mass spectrum (m/e): 265.3 (M+1).

Step 3. 4-Butyl-N-{2-[(2-dimethylamino-ethyl)-methyl-amino]-benzooxazol-5-yl}-benzamide; Hydrochloride

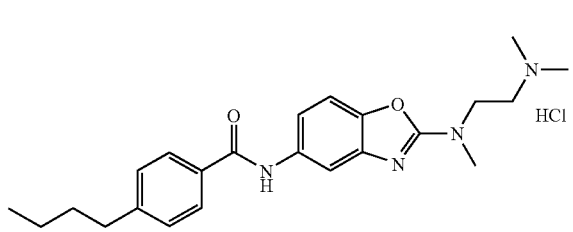

The title compound is prepared according to the procedure described in Method C, using $N^2$-(2-Dimethylamio-ethyl)-$N^2$-methyl-benzooxazole-2,5-diamine (0.548 g, 2.34 mmol), 4-N-butylbenzoic acid (0.500 g, 2.81 mmol), oxalyl chloride (0.37 mL, 4.21 mmol), and pyridine (0.19 mL, 2.34 mmol): (0.146 g, 14%). mass spectrum (m/e): 395.3 (M+1). $^1$H NMR (400 MHz, DMSO-d6): δ 10.21 (br s, 1H), 10.17 (s, 1H), 7.90-7.86 (m, 2H), 7.82-7.80 (m, 1H), 7.40-7.38 (m, 2H), 7.36-7.32 (m, 2H), 3.92 (t, J=6.4 Hz, 2H), 3.42 (q, J=5.6 Hz, 2H), 3.17 (s, 3H), 2.86 (d, J=4.8 Hz, 6H), 2.66 (t, J=7.6 Hz, 2H), 1.63-1.54 (m, 2H), 1.37-1.27 (m, 2H), 0.91 (t, J=7.6 Hz, 3H).

Example 50

4-Cyclohexyloxy-N-(2-[(2-dimethylamino-ethyl)-methyl-amino]-benzooxazol-5-yl)-benzamide; Hydrochloride

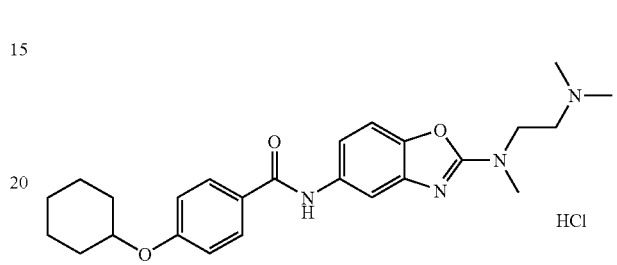

The title compound is prepared according to the procedure described in Method C, using $N^2$-(2-dimethylamino-ethyl)-$N^2$-methyl-benzooxazole-2,5-diamine (approximately 0.206 g, 0.878 mmol), 4-cyclohexyloxy-benzoic acid (0.232 g, 1.05 mmol), oxalyl chloride (0.14 mL, 1.58 mmol), and pyridine (0.07 mL, 0.878 mmol): (0.394 g, approx 100%). mass spectrum (m/e): 437.0 (M+1). $^1$H NMR (400 MHz, DMSO-d6): δ 10.19 (br s, 1H), 10.07 (s, 1H), 7.95-7.91 (m, 2H), 7.81-7.79 (m, 1H), 7.37 (d, J=1.3 Hz, 2H), 7.06-7.02 (m, 2H), 4.51-4.43 (m, 1H), 3.92 (t, J=6.4 Hz, 2H), 3.41 (q, J=5.6 Hz, 2H), 3.17 (s, 3H), 2.86 (d, J=4.8 Hz, 6H), 1.99-1.91 (m, 2H), 1.76-1.68 (m, 2H), 1.59-1.22 (m, 6H).

Example 51

N-{2-[(2-Dimethylamino-ethyl)-methyl-amino]-benzooxazol-5-yl}-6-(4-fluoro-phenyl)-nicotinamide; Hydrochloride

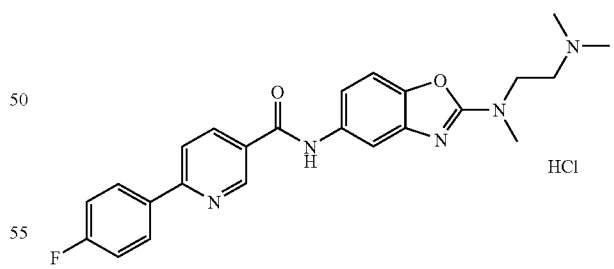

The title compound is prepared according to the procedure described in Method C, using $N^2$-(2-dimethylamino-ethyl)-$N^2$-methyl-benzooxazole-2,5-diamine (approximately 0.250 g, 1.07 mmol), 6-(4-fluoro-phenyl)-nicotinic acid (0.278 g, 2.56 mmol), oxalyl chloride (0.17 mL, 3.84 mmol), and pyridine (0.09 mL, 1.11 mmol): (0.096 g, 19%). mass spectrum (m/e): 434.0 (M+1), 432.3 (M−1). $^1$H NMR (400 MHz, DMSO-d6): δ 10.42 (s, 1H), 9.28 (br s, 1H), 9.18 (d, J=2.2 Hz, 1H), 8.41-8.36 (m, 1H), 8.28-8.22 (m, 2H), 8.15 (d, J=8.6 Hz, 1H), 7.83 (d, J=1.8 Hz, 1H), 7.44-7.34 (m, 4H), 3.90 (t, J=6.0 Hz, 2H), 3.43 (t, J=6.4 Hz, 2H), 3.16 (s, 3H), 2.91 (s, 6H).

Example 52

4'-Fluoro-biphenyl-4-carboxylic acid {2-[(2-dimethylamino-ethyl)-methyl-amino]-benzooxazol-5-yl}-amide; Hydrochloride

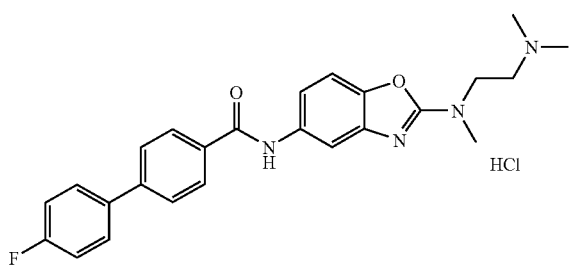

The title compound is prepared according to the procedure described in Method C, using $N^2$-(2-dimethylamino-ethyl)-$N^2$-methyl-benzooxazole-2,5-diamine (approximately 0.748 g, 3.19 mmol), 4'-fluoro-biphenyl-4-carboxylic acid (0.829 g, 2.56 mmol), oxalyl chloride (0.50 mL, 5.75 mmol), and pyridine (0.26 mL, 3.19 mmol): (1.38 g, 57%). mass spectrum (m/e): 433.3 (M+1), 431.3 (M−1). $^1$H NMR (400 MHz, DMSO-d6): δ 10.30 (s, 1H), 10.15 (br s, 1H), 8.09-8.04 (m, 2H), 7.85-7.78 (m, 5H), 7.45-7.38 (m, 2H), 7.37-7.31 (m, 2H), 3.92 (t, J=6.4 Hz, 2H), 3.45-3.39 (m, 2H), 3.18 (s, 3H), 2.87 (d, J=4.4 Hz, 6H).

Example 53

6-(4-Fluoro-phenyl)-N-{2-[methyl-(1-methyl-piperidin-4-yl)-amino]-benzooxazol-5-yl}-nicotinamide; Hydrochloride

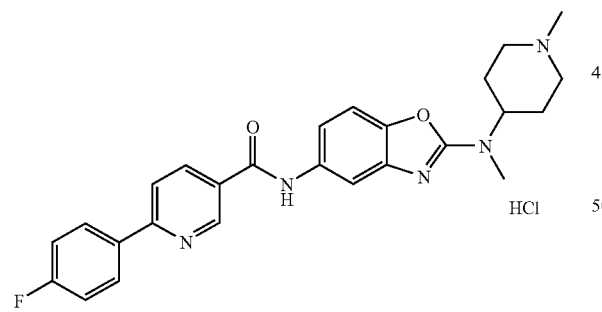

The title compound is prepared according to the procedure described in Method C, using $N^2$-methyl-$N^2$-(1-methyl-piperidin-4-yl)-benzooxazole-2,5-diamine (0.394 g, 1.51 mmol), 6-(4-fluoro-phenyl)-nicotinic acid (0.365 g, 1.68 mmol), oxalyl chloride (0.44 mL, 5.04 mmol); no pyridine used: (0.092 g, 12%). mass spectrum (m/e): 460.3 (M+1), 458.3 (M−1). $^1$H NMR (400 MHz, DMSO-d6): δ 10.51 (br s, 1H), 10.48 (s, 1H), 9.20 (d, J=2.2 Hz, 1H), 8.42 (dd, J=8.0, 2.0 Hz, 1H), 8.28-8.22 (m, 2H), 8.15 (d, J=8.0 Hz, 1H), 7.82 (s, 1H), 7.44-7.34 (m, 4H), 4.43-4.33 (m, 1H), 3.49 (d, J=11.6 Hz, 2H), 3.23-3.12 (m, 2H), 3.04 (s, 3H), 2.75 (d, J=4.8 Hz, 3H), 2.30-2.18 (m, 2H), 1.94 (d, J=12.4 Hz, 2H).

Example 54

N-{2-[(2-Dimethylamino-ethyl)-methyl-amino]-benzooxazol-5-yl}-3-phenoxy-benzamide; Hydrochloride

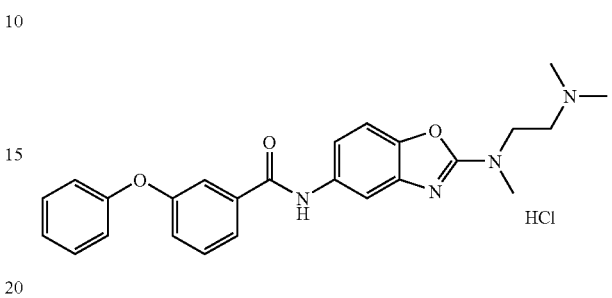

The title compound is prepared according to the procedure described in Method C, using $N^2$-(2-dimethylamino-ethyl)-$N^2$-methyl-benzooxazole-2,5-diamine (0.490 g, 2.09 mmol), 3-phenoxy-benzoic acid (0.537 g, 2.51 mmol), oxalyl chloride (0.55 mL, 6.30 mmol), and pyridine (0.17 mL, 2.10 mmol): (0.058 g, 6%). mass spectrum (m/e): 431.3 (M+1). $^1$H NMR (400 MHz, DMSO-d6): δ 10.28 (s, 1H), 10.15 (br s, 1H), 7.80-7.74 (m, 2H), 7.59-7.52 (m, 2H), 7.46-7.40 (m, 2H), 7.40-7.35 (m, 2H), 7.25-7.17 (m, 2H), 7.12-7.05 (m, 2H), 3.92 (t, J=6.0 Hz, 2H), 3.45-3.38 (m, 2H), 3.17 (s, 3H), 2.86 (d, J=4.4 Hz, 6H).

Example 55

N-{2-[(2-Dimethylamino-ethyl)-methyl-amino]-benzooxazol-5-yl})phenoxy-benzamide; Hydrochloride

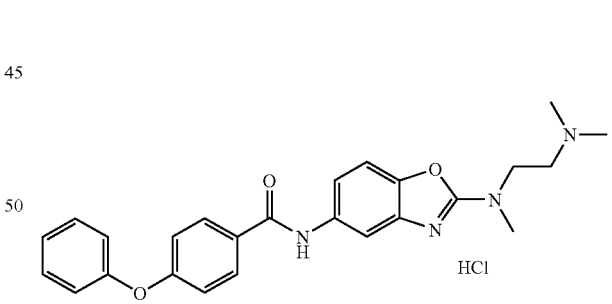

The title compound is prepared according to the procedure described in Method C, using $N^2$-(2-dimethylamino-ethyl)-$N^2$-methyl-benzooxazole-2,5-diamine (0.490 g, 2.09 mmol), 4-phenoxy-benzoic acid (0.537 g, 2.51 mmol), oxalyl chloride (0.55 mL, 6.30 mmol), and pyridine (0.17 mL, 2.10 mmol): (0.063 g, 7%). mass spectrum (m/e): 431.3 (M+1). $^1$H NMR (400 MHz, DMSO-d6): δ 10.20 (s, 1H), 10.09 (br s, 1H), 8.03-7.98 (m, 2H), 7.82-7.80 (m, 1H), 7.49-7.43 (m, 2H), 7.39 (s, 2H), 7.26-7.20 (m, 1H), 7.13-7.07 (m, 4H), 3.92 (t, J=7.2 Hz, 2H), 3.45-3.42 (m, 2H), 3.17 (s, 3H), 2.87 (d, J=4.8 Hz, 6H).

Example 56

Biphenyl-4-carboxylic Acid {2-[(2-dimethylamino-ethyl)-methyl-amino]-benzooxazol-5-yl}-amide; Hydrochloride

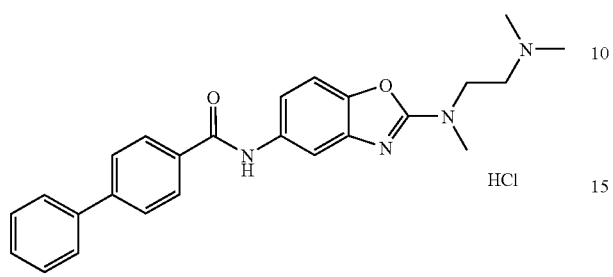

The title compound is prepared according to the procedure described in Method C, using $N^2$-(2-dimethylamino-ethyl)-$N^2$-methyl-benzooxazole-2,5-diamine (0.509 g, 2.17 mmol), biphenyl-4-carboxylic acid (0.516 g, 2.61 mmol), oxalyl chloride (0.57 mL, 6.51 mmol), and pyridine (0.18 mL, 2.17 mmol): (0.085 g, 9%). mass spectrum (m/e): 415.3 (M+1). $^1$H NMR (400 MHz, DMSO-d6): δ 10.32 (s, 1H), 10.23 (br s, 1H), 8.10-8.05 (m, 2H), 7.88-7.82 (m, 3H), 7.78-7.74 (m, 2H), 7.52 (t, J=7.2 Hz, 2H), 7.47-7.40 (m, 3H), 3.94 (t, J=6.4 Hz, 2H), 3.46-3.40 (m, 2H), 3.19 (s, 3H), 2.87 (d, J=4.8 Hz, 6H).

Example 57

5-(4-Fluoro-phenyl)-pyrazine-2-carboxylic acid {2-[(2-dimethylamino-ethyl)-methyl-amino]-benzooxazol-5-yl}-amide; Hydrochloride Step 1. 5-Chloro-pyrazine-2-carboxylic acid methyl ester Reflux a mixture of 5-Hydroxy-pyrazine-2-carboxylic acid (6.568 g, 46.88 mmol), thionyl chloride (51 mL, 703.2 mmol), and DMF (0.50 mL) for 4 h. Cool the mixture to room temperature, concentrate in vacuo, and pump on high vacuum for 3 h. Dilute the mixture with MeOH (25 mL) and add pyridine (4.5 mL, 55.7 mmol). Stir the mixture overnight at room temperature. Adsorb the reaction mixture onto silica gel and subject the mixture to flash column chromatography (330 g column, 25%-60% ethyl acetate/n-hexane) to yield the desired product (7.380 g, 91%). mass spectrum (m/e): 173.0 (M+1).

Step 2. 5-Chloro-pyrazine-2-carboxylic Acid

Dissolve 5-chloro-pyrazine-2-carboxylic acid methyl ester (10.0 g, 57.9 mmol) in THF (65 mL) and MeOH (65 mL). Cool the solution to 0° C. before adding 1N NaOH (63.7 mL) with stirring. Warm the mixture to room temperature and stir for 5 h. Concentrate the mixture in vacuo to 1/3 volume. Quench with 1N HCl (75 mL) to form a white precipitate. Dilute with $CH_2Cl_2$ (200 mL) and filter. Wash the filter cake with water and $CH_2Cl_2$. Separate the phases, dry the organic phase over $MgSO_4$, filter, and concentrate. Add the aqueous layer to the concentrated organic residue and concentrate. Purify by silica gel flash column chromatography, eluting with 40% ethyl acetate/n-hexane, followed by 10% MeOH, 3% acetic acid and 87% $CH_2Cl_2$. Collect the mixed fractions and concentrate. Take up the resulting solid with $CH_2Cl_2$ (50 mL) and $H_2O$ (50 mL) and stir. Filter the solid and add it to the first filter cake. Add 5.0N NaOH to the filtrate to make the solution basic. Separate the two layers. Discard the organic layer, add 5.0N HCl to the aqueous layer until acidic. Extract with $CH_2Cl_2$ (3×100 mL). Dry the organic layer over $Na_2SO_4$, filter, and concentrate. Add the solid to the pure fractions from the column. Combine the pure filter cakes with the pure fractions from the column, yielding the desired product (8.46 g, 92%). mass spectrum (exact mass): 157.99.

Step 3. 5-Chloro-pyrazine-2-carboxylic acid {2-[(2-dimethylamino-ethyl)-methyl-amino]-benzooxazol-5-yl}-amide

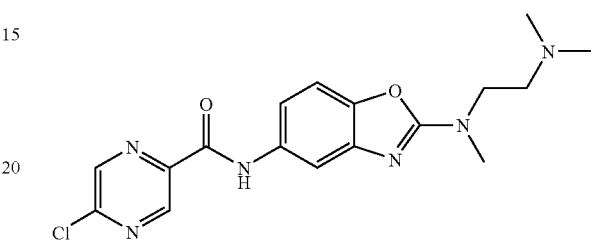

Method E: The titled compound is prepared using $N^2$-(2-dimethylamino-ethyl)-$N^2$-methyl-benzooxazole-2,5-diamine (0.250 g, 1.07 mmol), 5-chloro-pyrazine-2-carboxylic acid (0.186 g, 1.17 mmol), HATU (0.487 g, 1.28 mmol), and DMAP (0.012 g, 0.107 mmol) in $CH_3CN$ (10 mL) at room temperature. The reaction time was prolonged to 24 h and the compound was purified by silica gel flash column chromatography (40 g column, 5-10% MeOH/$CH_2Cl_2$) to yield an impure mixture (98 mg). mass spectrum (m/e): 375.0 (M+1). The mixture is used directly in the next reaction.

Step 4. 5-(4-Fluoro-phenyl)-pyrazine-2-carboxylic acid {2-[(2-dimethylamino-ethyl)methyl-amino]-benzooxazol-5-yl}-amide; Hydrochloride

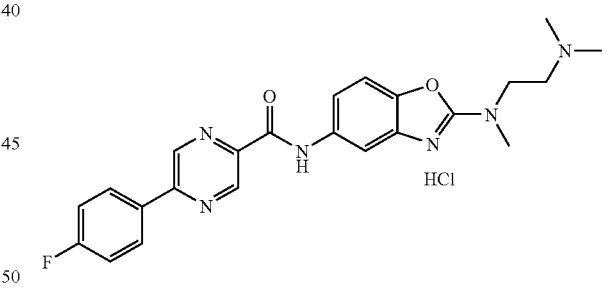

Dissolve the impure mixture from above (0.098 g) in 1,4-dioxane (15 mL) and water (3.0 mL). Add 4-fluoro-phenylboronic acid (0.037 g, 0.262 mmol), tetrakis(triphenylphosphine)palladium (0) (0.030 g, 0.026 mmol), and potassium carbonate (0.108 g, 0.784 mmol) to the solution, degas the mixture thrice, back-filling with an Ar-filled balloon each time. Reflux the mixture for 15 h. Adsorb the reaction mixture onto silica gel and concentrate in vacuo. Subject the mixture to silica gel flash column chromatography (40 g column, eluting with 0-10% 2N $NH_3$ in MeOH/$CH_2Cl_2$) to yield an impure mixture. Load the mixture onto a cartridge with DMSO and subject to reverse-phase flash column chromatography (Analogix SuperFlash™ SF40-152 g (Sepra C10), 5% $CH_3CN$/0.03% HCl(aqueous) for 5.0 min, 5% $CH_3CN$/0.03% HCl(aq)-100% $CH_3CN$ over 25.0 min) to yield the desired product (0.016 g, approx. 13%). mass spectrum (m/e): 435.3 (M+1). ¹H NMR (400 MHz, CD₃OD): δ 9.36 (s, 1H), 9.23 (s, 1H), 8.30-8.24 (m, 2H), 8.21 (s, 1H), 7.62 (m, 2H), 7.31 (t, J=8.8 Hz, 2H), 4.16 (br s, 2H), 3.62 (br s, 2H), 3.41 (s, 3H), 3.31 (s, 6H).

Example 58

N-{2-[(2-Dimethylamino-ethyl)-methyl-amino]-benzooxazol-5-yl}-4-isobutoxy-benzamide; Hydrochloride

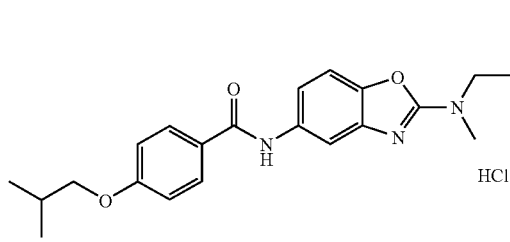

The title compound is prepared using N²-(2-dimethylamino-ethyl)-N²-methyl-benzooxazole-2,5-diamine (0.244 g, 1.04 mmol), 4-isobutoxy-benzoic acid (0.303 g, 1.56 mmol), HATU (0.396 g, 1.04 mmol), and DMAP (0.012 g, 0.104 mmol) in CH₃CN (10 mL): (0.095 g, 20%). mass spectrum (m/e): 411.2 (M+1). ¹H NMR (400 MHz, DMSO-d6): δ 10.26 (br s, 1H), 10.11 (s, 1H), 7.98-7.93 (m, 2H), 7.83 (br s, 1H), 7.41-7.38 (m, 2H), 7.07-7.03 (m, 2H), 3.94 (t, J=6.8 Hz, 2H), 3.83 (d, J=6.4 Hz, 2H), 3.44-3.40 (m, 2H), 3.18 (s, 3H), 2.86 (d, J=4.8 Hz, 6H), 2.04 (septet, J=6.8 Hz, 1H), 1.00 (d, J=6.4 Hz, 6H).

Example 59

5-(4-Fluoro-phenyl)-pyrazine-2-carboxylic acid {2-[methyl-(1-methyl-piperidin-4-yl)-amino]-benzooxazol-5-yl}-amide; Hydrochloride Step 1. 5-Chloro-pyrazine-2-carboxylic acid {2-[methyl-(1-methyl-piperidin-4-yl)-amino]-benzooxazol-5-yl}-amide

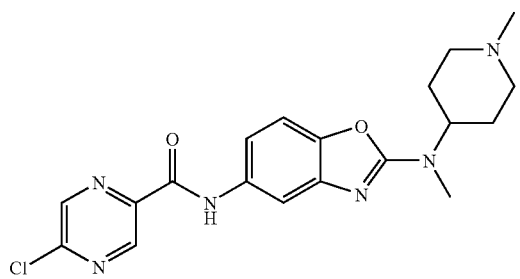

The title compound was prepared using N²-Methyl-N²-(1-methyl-piperidin-4-yl)-benzooxazole-2,5-diamine (0.368 g, 1.41 mmol), 5-Chloro-pyrazine-2-carboxylic acid (0.247 g, 1.55 mmol), HATU (0.645 g, 1.70 mmol), and DMAP (0.016 g, 0.141 mmol) in CH₃CN (20 mL). The compound was subjected to flash column chromatography (120 g column, 2-8% 2N NH₃ in MeOH/CH₂Cl₂) to yield an impure mixture, which was carried on to the next reaction (0.316 g).

Step 2. 5-(4-Fluoro-phenyl)-pyrazine-2-carboxylic acid {2-[methyl-(1-methyl-piperidin-4-yl)-amino]-benzooxazol-5-yl}-amide; Hydrochloride

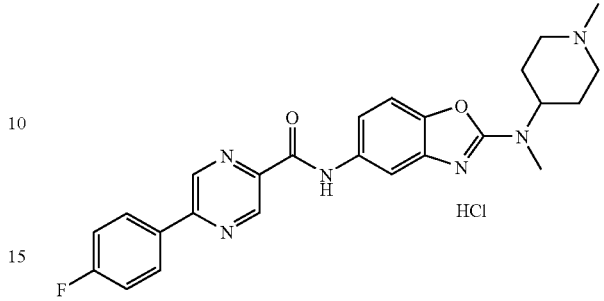

The impure mixture from above (0.316 g) was dissolved in 1,4-dioxane (15 mL) and H₂O (3.0 mL). Add 4-Fluoro-phenylboronic acid (0.037 g, 0.262 mmol), Tetrakis(triphenylphosphine)palladium (0) (0.030 g, 0.026 mmol), and potassium carbonate (0.108 g, 0.784 mmol) to the solution, degas the mixture thrice, back-filling with an argon-filled balloon each time. Reflux the mixture for 15 h. Adsorb the reaction mixture onto silica gel and concentrate in vacuo. Subject the mixture to silica gel flash column chromatography (40 g column, eluting with 0-10% 2N NH₃ in MeOH/CH₂Cl₂) to yield an impure mixture. Load the mixture onto a cartridge with DMSO and subject to reverse-phase flash column chromatography (Analogix SuperFlash™ SF40-152 g (SepraC10), 5% CH₃CN/0.03% HCl (aqueous) for 5 min, 5% CH₃CN/0.03% HCl (aqueous)-100% CH₃CN over 25 min) to yield the desired product (0.067 g, approx. 17%). mass spectrum (m/e): 461.0 (M+1). ¹ᴴNMR (400 MHz, CD₃OD): δ 9.37 (d, J=1.0 Hz, 1H), 9.24 (d, J=1.0 Hz, 1H), 8.31-8.25 (m, 3H), 7.73 (dd, J=8.8 Hz, 1.9 Hz, 1H), 7.64 (d, J=9.0 Hz, 1H), 7.35-7.28 (m, 2H), 4.62-4.51 (m, 1H), 3.72 (d, J=12.4 Hz, 2H), 3.37-3.31 (m, 2H), 3.32 (s, 3H), 2.96 (s, 3H), 2.44-2.31 (m, 2H), 2.24 (d, J=13.6 Hz, 2H).

Example 60

2',4'-Difluoro-biphenyl-4-carboxylic acid {2-[methyl-(1-methyl-piperidin-4-yl)-amino]-benzooxazol-5-yl}-amide; Hydrochloride Step 1. 2',4'-Difluoro-biphenyl-4-carboxylic Acid Methyl Ester

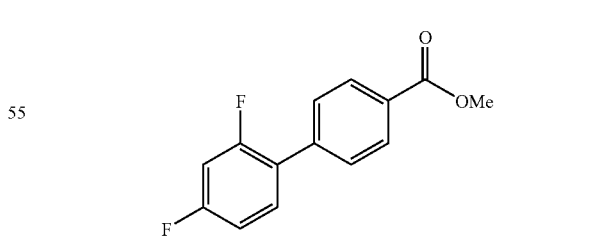

Dissolve 2,4-difluoro-1-iodo-benzene (0.25 mL, 2.08 mmol) in anhydrous 1,2-dimethoxyethane (30 mL). Add 4-methoxycarbonyl-phenyl-boronic acid (0.375 g, 2.08 mmol), cesium fluoride (1.58 g, 10.42 mmol), and dichloro[1,1'-bis(diphenylphosphino)ferrocene]palladium (II) dichloromethane adduct (0.170 g, 0.208 mmol). Degas the mixture thrice and back-fill with nitrogen. Immerse the mixture into a pre-heated (85° C.) oil bath and stir overnight. Filter the hot mixture through Celite® and concentrate in vacuo. Subject the residue to silica gel flash column chromatography (40 g column, 0-10% ethyl acetate/n-hexane) to yield the desired product (0.441 g, 85%). mass spectrum (n/e): 249.0 (M+1).

Step 2. 2',4'-Difluoro-biphenyl-4-carboxylic Acid

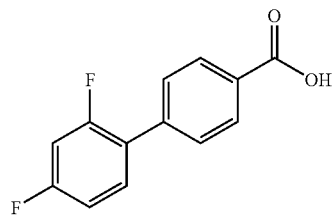

Dissolve 2',4'-difluoro-biphenyl-4-carboxylic acid methyl ester (0.426 g, 1.716 mmol) in THF (5 mL) and add a solution of NaOH (0.164 g, 4.12 mmol) in water (5.0 mL). Stir the mixture for 3 d at 40° C. Concentrate in vacuo to remove THF, add 1.0M HCl until pH 2, adsorb the mixture onto silica gel, and subject the mixture to flash column chromatography (40 g column, eluting with 50% ethyl acetate/n-hexane to 100% ethyl acetate) to yield the desired-product (0.373 g, 93%). mass spectrum (m/e): 233.3 (M−1).

Step 3. 2',4'-Difluoro-biphenyl-4-carboxylic acid {2-[methyl-(1-methyl-piperidin-4-yl)-amino]-benzooxazol-5-yl}-amide; Hydrochloride

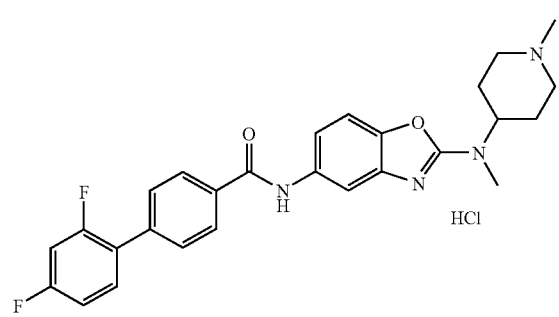

The title compound is prepared using $N^2$-methyl-$N^2$-(1-methyl-piperidin-4-yl)-benzooxazole-2,5-diamine (0.178 g, 0.684 mmol), 2',4'-Difluoro-biphenyl-4-carboxylic acid (0.160 g, 0.684 mmol), HATU (0.260 g, 0.684 mmol), DMAP (0.008 g, 0.068 mmol), and $CH_3CN$ (5.0 mL): (0.273 g, 78%). mass spectrum (m/e): 477.0 (M+1). $^1$H NMR (400 MHz, DMSO-d6): δ 10.59 (br s, 1H), 10.35 (s, 1H), 8.09-8.05 (m, 2H), 7.83 (d, J=2.2 Hz, 1H), 7.71-7.64 (m, 3H), 7.47-7.39 (m, 3H), 7.25 (dt, J=8.6, 2.6 Hz, 1H), 4.44-4.34 (m, 1H), 3.49 (d, J=12.0 Hz, 2H), 3.23-3.12 (m, 2H), 2.75 (d, J=4.4 Hz, 2H), 2.31-2.18 (m, 2H), 1.95 (d, J=13.2 Hz, 2H).

Example 61

Biphenyl-4-carboxylic acid {2-[methyl-(1-methyl-piperidin-3-yl)-amino]-benzooxazol-5-yl}-amide Hydrochloride (Isomer 1 and 2)

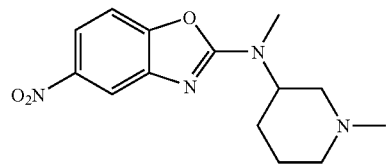

Step 1. Methyl-(5-nitro-benzooxazol-2-yl)-amine

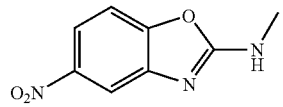

Place 2-methylsulfanyl-5-nitro-benzooxazole (2.00 g, 9.51 mmol) in a sealed tube. Add 2M ammonia in methanol and place the reaction under nitrogen. Seal tightly and heat to 100° C. for 18 h. Cool to rt (room temperature) and triturate the reaction with methanol. Filter off solid and wash with methanol. Chromatograph (silica gel, eluting with 0-10% 2M $NH_3$ in MeOH:DCM (dichloromethane) to yield 902 mg (49%) of the title compound: mass spectrum (ion-spray): (m/z)=194.0 (M+1).

Step 2. Methyl-(1-methyl-piperidin-3-yl)-(5-nitro-benzooxazol-2-yl)-amine

Place 1-methyl-piperidin-3-ol in DCM (10 mL). Add diisopropylethylamine (DIEA) (1.84 mL, 11.15 mmol) followed by methanesulfonyl chloride (0.866 mL, 11.15 mmol). Stir at rt for 17 h. Add DCM (10 mL) and wash the organic layer with 1N NaOH (20 mL). Collect the organic layer, dry over $MgSO_4$, filter, and concentrate in vacuo. Place methyl-(5-nitro-benzooxazol-2-yl)-amine (600 m g, 3.11 mmol) in DMF (10 mL). Add 60% NaH in mineral oil (124 mg, 3.11 mmol) and stir for 10 min. Then add methanesulfonic acid 1-methyl-piperidin-3-yl ester (1.80 g, 9.30 mmol) dissolved in DMF (5 mL). Heat the reaction to 80° C. for 19 h. Cool to rt and add ethyl acetate (50 mL) and water (50 mL). Separate the organic layer and wash with water (2×25 mL), then brine (25 mL). Collect the organic layer, dry over $MgSO_4$, filter, and concentrate in vacuo. Chromatograph (silica gel, eluting with 0-10% 2M $NH_3$ in MeOH:DCM, then 10% 2M $NH_3$ in MeOH:DCM) to yield 445 mg (49%) of the title compound: mass spectrum (ion-spray): (m/z)=291.3 (M+1).

Step 3. N²-Methyl-N²-(1-methyl-piperidin-3-yl)-benzooxazole-2,5-diamine

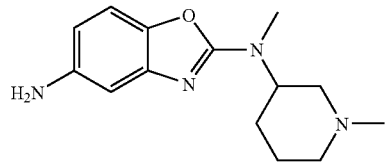

Place methyl-(1-methyl-piperidin-3-yl)-(5-nitro-benzooxazol-2-yl)-amine (440 mg, 1.51 mmol) and iron powder (423 mg, 7.58 mmol) in acetic acid (10 mL). Heat the reaction to 40° C. for 2 h. Cool to rt and then load onto a Varian™ SCX column. Wash the column with methanol and DCM. Flush the compound off the column by eluting with 2M NH₃ in methanol. Collect filtrate and concentrate in vacuo. Chromatograph (silica gel, eluting with 0-10% 2M NH₃ in MeOH:DCM, then 10% 2M NH₃ in MeOH:DCM) to yield 385 mg (98%) of the title compound: mass spectrum (ion-spray): (m/z)=261.3 (M+1).

Example 61a

Biphenyl-4-carboxylic acid {2-[methyl-(1-methyl-piperidin-3-yl)-amino]-benzooxazol-5-yl}-amide Hydrochloride (Isomer 1 and Isomer 2)

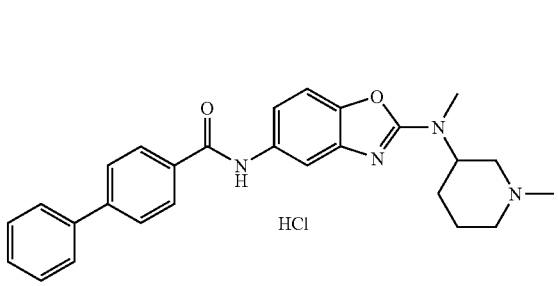

Place N²-methyl-N²-(1-methyl-piperidin-3-yl)-benzooxazole-2,5-diamine (190 mg, 0.730 mmol), 4-dimethylaminopyridine (DMAP) (16 mg, 0.146 mmol), O-(7-azabenzotriazol-1-yl)-N,N,N',N'-tetramethyluronium hexafluorophosphate (HATU) (333 mg, 0.876 mmol), and biphenyl-4-carboxylic acid (173 mg, 0.876 mmol) in acetonitrile (5 mL). Heat the reaction to 60° C. for 17 h. Cool to rt and chromatograph (silica gel, eluting with 0-10% 2M NH₃ in MeOH:DCM) to yield 206 mg (59%) of the title compound as a racemate. Purify by chiral chromatography using single-injection with three-pass cycle separation utilizing 50/50 acetonitrile:3 Å ethanol with 0.2% dimethylethylamine at 400 mL/min on a Chiralpak AD-H column. Dissolve the two enantiomers in DCM and add 4N HCl in dioxane (1.05 molar equivalents). Concentrate in vacuo to yield isomer #1 (30 mg) and isomer #2 (28 mg): mass spectrum (ion-spray): (m/z)= 441.0 (M+1).

Example 61b 4'-Fluoro-biphenyl-4-carboxylic acid {2-[methyl-(1-methyl-piperidin-3-yl-amino]-benzooxazol-5-yl}-amide, Isomer 1 and Isomer 2)

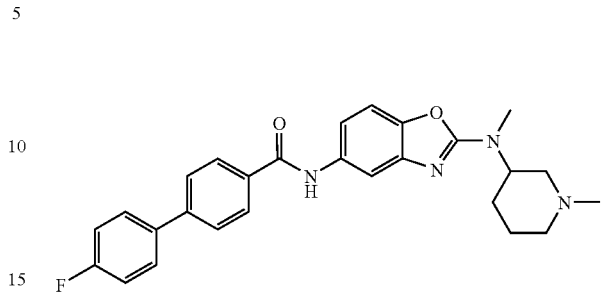

The title compound is prepared according to the procedure described in Example 61a to yield isomer #1 (20 mg) and isomer #2 (19 mg): mass spectrum (ion-spray): (m/z)=459.2 (M+1).

Example 62

4'-Fluoro-biphenyl-4-carboxylic acid {2-[methyl-(2-pyrrolidin-1-yl-ethyl)-amino]-benzooxazol-5-yl}-amide

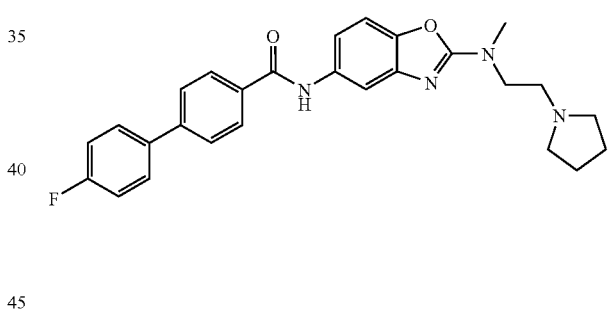

Step 1. Methyl-(5-nitro-benzooxazol-2-yl)-2-pyrrolidin-1-yl-ethyl)-amine

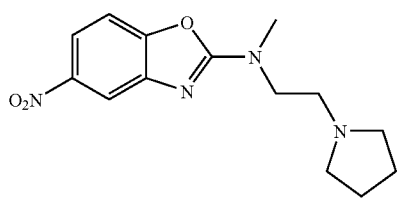

The title compound is prepared according to the procedure described in Example 61, Step 2 using 2-pyrrolidin-1-yl-ethanol (537 mg, 4.66 mmol), methanesulfonyl chloride (0.434 mL, 5.59 mmol), DIEA (0.924 mL, 5.59 mmol), methyl-(5-nitro-benzooxazol-2-yl)-amine (300 mg, 1.55 mmol), and 60% NaH in mineral oil (62 mg, 1.55 mmol) to yield 170 mg (38%) of product: mass spectrum (ion-spray): (m/z)=291.3 (M+1).

Step 2. N²-Methyl-N²-(2-pyrrolidin-1-yl-ethyl)-benzooxazole-2,5-diamine

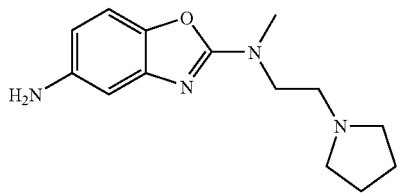

The title compound is prepared according to the procedure outlined in Example 61, Step 3 using methyl(5-nitro-benzooxazol-2-yl)-(2-pyrrolidin-1-yl-ethyl)-amine (160 mg, 0.55 mmol), iron powder (154 mg, 2.75 mmol), and acetic acid (5 mL) to yield 60 mg (42%) of product: mass spectrum (ion-spray): (m/z)=261.2 (M+1).

Step 3. 4'-Fluoro-biphenyl-4-carboxylic acid {2-[methyl-(2-pyrrolidin-1-yl-ethyl)-amino]-benzooxazol-5-yl}-amide The title compound is prepared according to the procedure outlined in Example 61a to yield the title compound 102 mg (90%). mass spectrum (ion-spray): (m/z)=459.2 (M+1).

General Method F

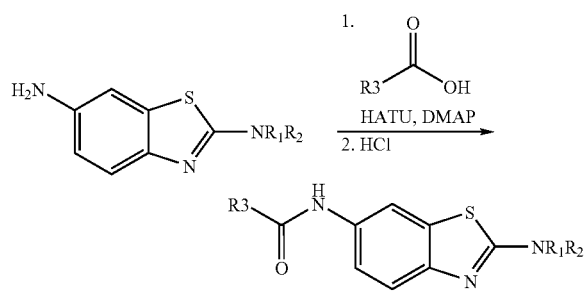

Place benzothiazole-2,6-diamine (1.0 equiv), DMAP (0.1 equiv), HATU (1.3 equiv), and carboxylic acid (1.3 equiv) in CH₂Cl₂ (11 mL/mmol of benzothiazole-2,6-diamine). Shake the reaction mixture overnight at room temperature. Chromatograph (silica gel, eluting with 0-10% 2M NH₃ in MeOH/DCM) to yield the desired product.

For racemic mixture separation into enantiomers: Chromatograph via single injection, three-pass, recycle separation utilizing 50/50 Acetonitrile/3 Å ethanol with 0.2% dimethylethylamine at 400 ml/min. on a Chiralpak AD-H column.

For hydrochloride salt formation: Dissolve the product into MeOH or Et₂O/THF and add HCl (1.05 equiv., 11.0M in Et₂O or 4.0M in 1,4-dioxane). Stir for 20 min at room temperature, concentrate in vacuo or decant the solvent and pump on high vacuum for several hours to yield the desired product.

General Method G

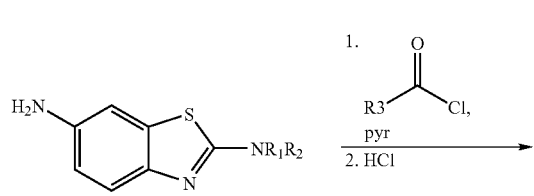

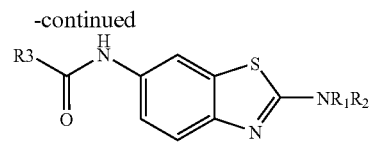

Add oxalyl chloride (3.0 equiv) and 5 drops of DMF to a stirring suspension of carboxylic acid (1.2 equiv) in CH₂Cl₂ (5.5 mL/mmol benzothiazole-2,5-diamine). Stir the reaction mixture at room temperature for 3 h. Concentrate the mixture in vacuo, add n-hexane, re-concentrate, and re-dissolve in CH₂Cl₂ (3 mL/mmol of benzothiazole-2,5-diamine). Add the resultant carbonyl chloride solution to a mixture of benzothiazole-2,5-diamine (1.0 equiv) and pyridine (1.0 equiv) in CH₂Cl₂ (5.5 mL/mmol of benzothiazole-2,5-diamine). Stir the reaction mixture at room temperature for 18 h. If product precipitates, filter the reaction mixture and wash the product with CH₂Cl₂. Dry the product on high vacuum to yield the desired product. If the product is soluble, wash the mixture with saturated NaHCO₃(aq), dry the organic phase over Na₂SO₄, filter, and concentrate the mixture in vacuo. Subject the residue to silica gel flash column chromatography (eluting with 0-10% 2N NH₃ in MeOH/CH₂Cl₂) to yield the desired product. For racemic mixture separation into enantiomers: Chromatograph via single injection, three-pass, recycle separation utilizing 50/50 Acetonitrile/3 Å ethanol with 0.2% dimethylethylamine at 400 ml/min. on a Chiralpak AD-H column.

For hydrochloride salt formation: Dissolve the product into MeOH or Et₂O/THF and add HCl (1.05 equiv., 1.0M in Et₂O or 4.0M in 1,4-dioxane). Stir for 20 min at room temperature, concentrate in vacuo or decant the solvent and pump on high vacuum for several hours to yield the desired product.

Example 63

4'-Fluoro-biphenyl-4-carboxylic acid [2-(methyl-pyrrolidin-3-ylmethyl-amino)-benzothiazol-6-yl]-amide,

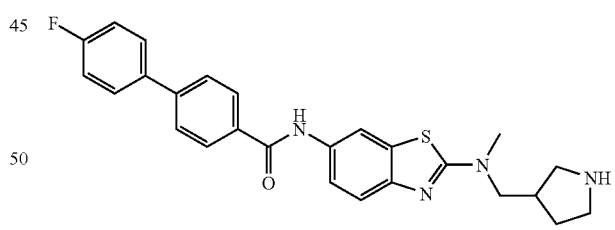

Step 1. 3-[(6-Nitro-benzothiazol-2-ylamino)-methyl]-pyrrolidine-1-carboxylic acid tert-butyl ester

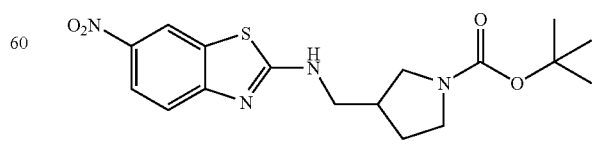

Prepare employing 2-chloro-6-nitrobenzothiazole (10.68 g, 49.8 mmol), 3-aminomethyl-pyrrolidine-1-carboxylic acid tert-butyl ester (10.0 g, 49.9 mmol), and triethylamine (7 mL, 50.2 mmol) in THF (500 mL) heated to 100° C. to 150° C. with overnight stirring. Cool to room temperature and neutralize to pH7 using 5N HCl. Extract the aqueous layer with ethyl acetate. Wash the organic layer with brine, collect the organic layer, dry over anhydrous magnesium sulfate, filter, and concentrate to yield 10.7 g (57%) of the title compound. $^1$H NMR $\delta_H$ (400 MHz, DMSO) 8.82 (s, 1H), 8.68 (s, 1H), 8.08 (dd, J=2.4, 8.8 Hz, 1H), 7.44 (d, J=8.8 Hz, 1H), 3.41 (m, 2H), 3.37 (m, 1H), 3.29 (m, 1H), 2.99 (m, 1H), 2.48 (m, 2H), 1.95 (m, 1H), 1.62 (m, 1H). 1.37 (s, 9H).

Step 2. 3-{[Methyl-(6-nitro-benzothiazol-2-yl)-methyl-amino]-methyl}-pyrrolidine-1-carboxylic Acid Tert-Butyl Ester

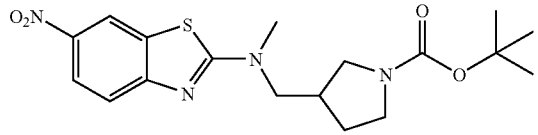

Dissolve 3-[(6-nitro-benzothiazol-2-ylamino)-methyl]-pyrrolidine-1-carboxylic acid tert-butyl ester (5.55 g, 14.7 mmol) in DMF (30 mL) and cool to 5° C. Add 60% NaH in mineral oil (1.12 g, 16.13 mmol) and stir for 5 min. Add iodomethane (6.0 mL, 74 mmol) and stir at 5° C. for 30 min. Quench the reaction with water and dilute with ethyl acetate. Wash the organic layer with water (5×20 mL), then wash with brine. Collect the organic layer, dry over Na$_2$SO$_4$, filter, and concentrate in vacuo. Chromatograph (silica gel, eluting with 20-60% Ethyl acetate:Hexane) to yield 1.96 g (34%) of the title compound. mass spectrum (ion-spray): (m/z)=393.3 (M+1).

Step 3. 3-{[(6-Amino-benzothiazol-2-yl)-methyl-amino]-methyl}-pyrrolidine-1-carboxylic Acid Tert-Butyl Ester

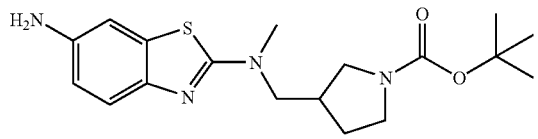

The title compound is prepared according to the procedure described in Example 1, Step 3, employing 3-{[methyl-(6-nitro-benzothiazol-2-yl)-methyl-amino]-methyl}-pyrrolidine-1-carboxylic acid tert-butyl ester (1.96 g, 4.99 mmol) to yield 1.55 g (86%) of the product. mass spectrum (ion-spray): (m/z)=363.3 (M+1).

Step 4. 3-[({6-{(4'-Fluoro-biphenyl-4-carbonyl)-amino]-benzothiazol-2-yl}-methyl-amino)-methyl]-pyrrolidine-1-carboxylic Acid Tert-Butyl Ester

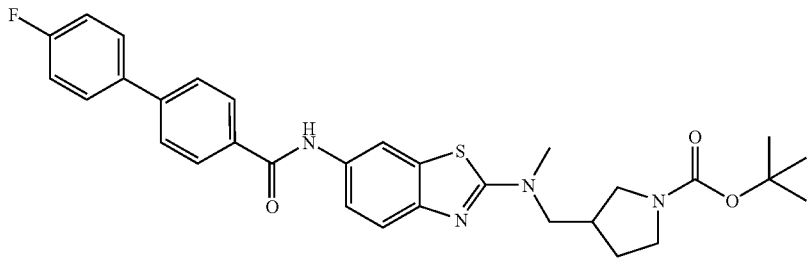

The title compound is prepared according to the procedure described in General Method G employing 3-{[(6-amino-benzothiazol-2-yl)-methyl-amino]-methyl}-pyrrolidine-1-carboxylic acid tert-butyl ester (1.55 g, 4.23 mmol) to yield 1.92 g (81%) of the product: mass spectrum (ion-spray): (m/z) 461.2 (M+1-Boc).

Step 6. 4'-Fluoro-biphenyl-4-carboxylic acid [2-(methyl-pyrrolidin-3-ylmethyl-amino)-benzothiazol-6-yl]-amide Place 3-[({6-{(4'-fluoro-biphenyl-4-carbonyl)-amino]-benzothiazol-2-yl}-methyl-amino)-methyl]-pyrrolidine-1-carboxylic acid tert-butyl ester in DCM (50 mL). Add trifluoroacetic acid (100 mL) and stir at rt for 6 h. Concentrate in vacuo and then add DCM:Hexane and concentrate in vacuo. Dissolve the residue in 1:1 MeOH:DCM and add polyvinyl pyridine (3 g) and stir for 15 min. Filter the solution and wash the resin with DCM. Collect the filtrate and concentrate in vacuo to yield 1.50 g (95%) of the title compound. mass spectrum (ion-spray): (m/z)=461.0 (M+1).

Example 64

4'-Fluoro-biphenyl-4-carboxylic Acid {2-[(1-isopropyl-pyrrolidin-3-ylmethyl)-methyl-amino]-benzothiazol-6-yl}-amide

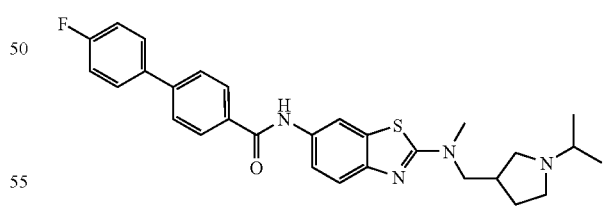

Place 4'-fluoro-biphenyl-4-carboxylic acid [2-(methyl-pyrrolidin-3-ylmethyl-amino)-benzothiazol-6-yl]-amide (16 mg, 0.035 mmol), 2-iodopropane (0.007 mL, 0.070 mmol), and potassium carbonate (15 mg, 0.108 mmol) in DMF (2 mL) and stir at rt for 3 d. Dilute the reaction with ethyl acetate and wash the organic layer with water (5 times). Chromatograph (silica gel, eluting with 10% 2M NH$_3$ in MeOH:DCM) to yield 16 mg (91%) of the title compound: mass spectrum (ion-spray): (m/z)=503.3 (M+1).

Example 65

4'-Fluoro-biphenyl-4-carboxylic acid {2-[(1-ethyl-pyrrolidin-3-ylmethyl)-methyl-amino]-benzothiazol-6-yl}-amide

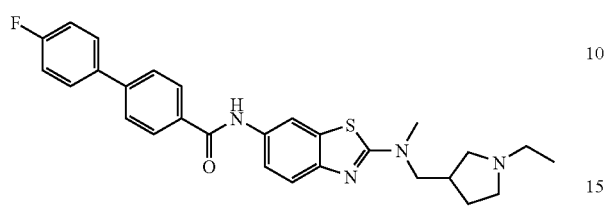

Place 4'-fluoro-biphenyl-4-carboxylic acid [2-(methyl-pyrrolidin-3-ylmethyl-amino)-benzothiazol-6-yl]-amide (123 mg, 0.267 mmol) in THF (3 mL) and cool to 0° C. Add acetaldehyde (0.040 mL, 0.716 mmol) and sodium triacetoxyborohydride (88 mg, 0.415 mmol). Stir at 0° C. for 10 min. Dilute with DCM and wash with 1N NaOH. Collect the organic layer and chromatograph (silica gel, eluting with 10% 2M NH₃ in MeOH:DCM) to yield 102 mg (78%) of the title compound: mass spectrum (ion-spray): (m/z)=489.0 (M+1).

Example 66

4'-Fluoro-biphenyl-4-carboxylic acid {2-[(1-acetyl-pyrrolidin-3-ylmethyl)-methyl-amino]-benzothiazol-6-yl}-amide

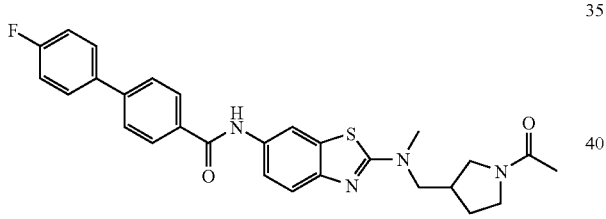

Add acetyl chloride and stir overnight at rt. Chromatograph (silica gel, eluting with 10% 2M NH₃ in MeOH:DCM) to yield 18 mg (20%) of the title compound: mass spectrum (ion-spray): (m/z)=503.0 (M+1).

Intermediate 1

Methyl-(6-nitro-benzothiazol-2-yl)-amine

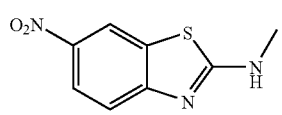

Place 2-chloro-6-nitro-benzothiazole (5.82 g, 27.1 mmol) in THF (130 mL). Add 40% methylamine in water (7 mL) and stir until the product precipitates out. Concentrate in vacuo and then triturate with methanol. Filter off the product and wash with methanol, Dry thoroughly to yield 4.99 g (88%) of the title compound: mass spectrum (ion-spray): (m/z)=210.0 (M+1).

Intermediate 2

Methyl-(6-nitro-benzothiazol-2-yl)-(2-pyrrolidin-1-yl-ethyl)-amine

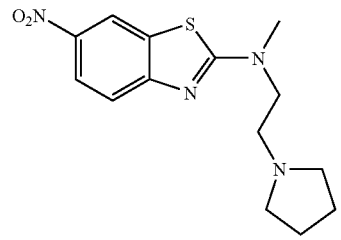

The title compound is prepared according to the general procedure outlined in Example 61, Step 2, utilizing methyl-(6-nitro-benzothiazol-2-yl)-amine (1.15 g, 5.50 mmol) to yield 320 mg (19%) of product. mass spectrum (ion-spray): (m/z)=307.3 (M+1).

Intermediate 3

Methyl-(1-methyl-piperidin-3-yl)-(6-nitro-benzothiazol-2-yl)-amine

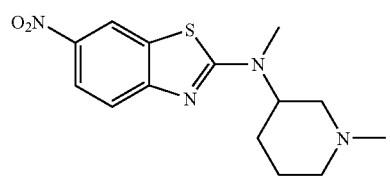

The title compound is prepared according to the general procedure outlined in Example 61, Step 2, utilizing methyl-(6-nitro-benzothiazol-2-yl)-amine (1.14 g, 5.45 mmol) to yield 420 mg (25%) of product: mass spectrum (ion-spray): (m/z)=307.3 (M+1).

Intermediate 4

Methyl-(2-morpholin-4-yl-ethyl)-(6-nitro-benzothiazol-2-yl)-amine

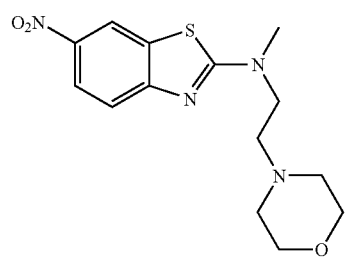

The title compound is prepared according to the general procedure outlined in Example 61, Step 2, utilizing methyl- (6-nitro-benzothiazol-2-yl)-amine (1.18 g, 5.64 mmol) and N-(2-chloroethyl)-morpholine hydrochloride (2.45 g, 13.17 mmol) to yield 1.43 g (79%) of the product. mass spectrum (ion-spray): (m/z)=323.2 (M+1).

Intermediate 5

Methyl-(6-nitro-benzothiazol-2-yl)-(2-piperidin-1-yl-ethyl)-amine

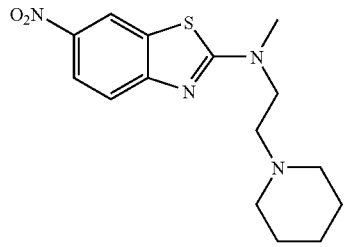

The title compound is prepared according to the general procedure outlined in Example 61, Step 2, utilizing methyl (6-nitro-benzothiazol-2-yl)-amine (979 mg, 4.68 mmol) and N-(2-chloroethyl)-piperidine hydrochloride (2.01 g, 10.92 mmol) to yield 1.43 g (79%) of the product. mass spectrum (ion-spray): (m/z)=321.3 (M+1).

The following compounds, Intermediates 6 to 9, are prepared according to the procedure outlined in Example 1, Step 3.

Intermediate 6

$N^2$-Methyl-$N^2$-(2-pyrrolidin-1-yl-ethyl)-benzothiazole-2,6-diamine

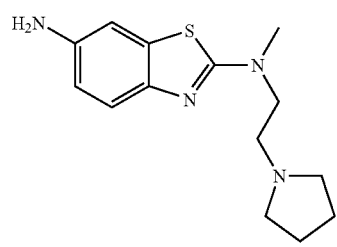

Mass spectrum (ion-spray): (m/z)=277.3 (M+1).

Intermediate 7

$N^2$-Methyl-$N^2$-(1-methyl-piperidin-3-yl)-benzothiazole-2,6-diamine

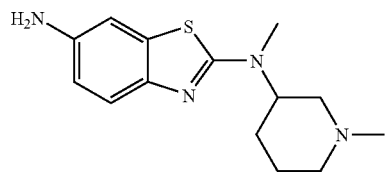

$^1$H NMR (400 MHz, CDCl$_3$): δ 7.32 (d, J=8.8 Hz, 1H), 6.93 (s, 1H), 6.65 (dd, J=2.4, 8.4 Hz, 1H), 3.79 (m, 1H), 3.45 (m, 1H), 3.24 (m, 1H), 3.22 (s, 3H), 2.85 (bs, 1H), 2.50 (s, 3H), 2.35 (m, 1H), 2.04 (m, 1H), 1.87 (m, 1H), 1.75 (m, 2H).

Intermediate 8

$N^2$-Methyl-$N^2$-(2-morpholin-4-yl-ethyl)-benzothiazole-2,6-diamine

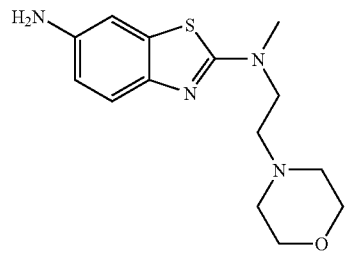

$^1$H NMR (400 MHz, DMSO): δ 7.10 (d, J=8.4 Hz, 1H), 6.85 (s, 1H), 6.50 (dd, J=2.0, 8.8 Hz, 1H), 4.80 (bs, 2H), 3.53 (m, 6H), 3.05 (s, 3H), 2.52 (m, 2H), 2.40 (m, 4H), 2.48 (m, 2H).

Intermediate 9

$N^2$-Methyl-$N^2$-(2-piperidin-1-yl-ethyl)-benzothiazole-2,6-diamine

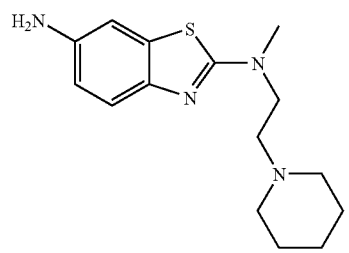

$^1$H NMR (400 MHz, DMSO): δ 7.23 (d, J=8.4 Hz, 1H), 7.01 (s, 1H), 6.73 (dd, J=2.0, 8.4 Hz, 1H), 3.65 (m, 2H), 3.34 (s, 3H), 2.65 (m, 2H), 2.55 (bs, 4H), 1.61 (m, 4H), 1.47 (m, 2H).

The following compounds, Examples 67 to 70, are prepared according to the procedure outlined in General Method G using the appropriate intermediate from above.

Example 67

4'-Fluoro-biphenyl-4-carboxylic acid {2-[methyl-(2-pyrrolidin-1-yl-ethyl)-amino]-benzothiazol-6-yl}-amide

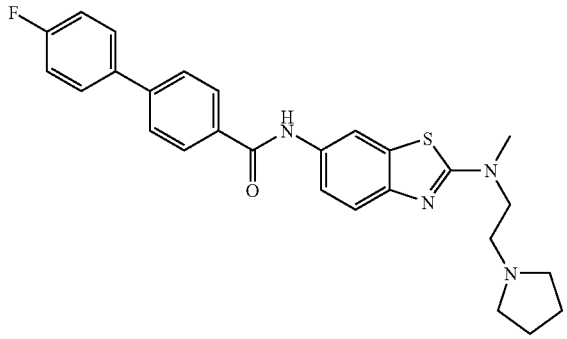

Mass spectrum (ion-spray): (m/z)=475.0 (M+1).

Example 68

4'-Fluoro-biphenyl-4-carboxylic acid {2-[methyl-(1-methyl-piperidin-3-yl)-amino]-benzothiazol-6-yl}-amide

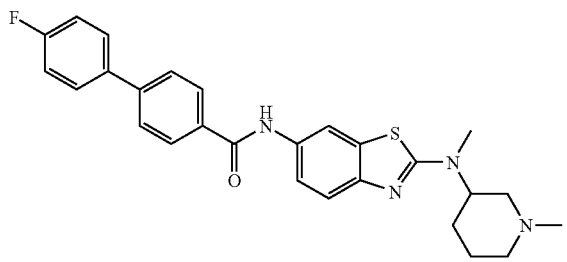

Mass spectrum (ion-spray): (m/z)=475.0 (M+1).

Example 69

4'-Fluoro-biphenyl-4-carboxylic acid {2-[methyl-(2-morpholin-4-yl-ethyl)-amino]-benzothiazol-6-yl}-amide

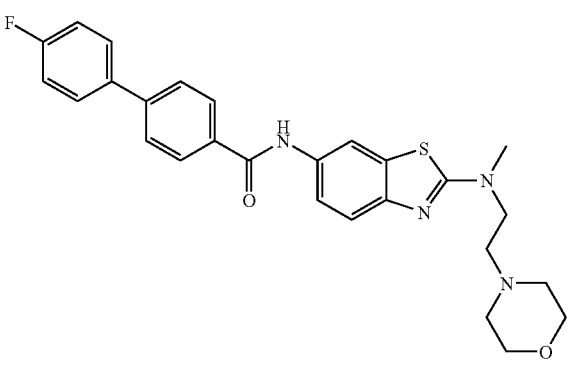

Mass spectrum (ion-spray): (m/z)=491.0 (M+1).

Example 70

4'-Fluoro-biphenyl-4-carboxylic acid {2-[methyl-(2-piperidin-1-yl-ethyl)-amino]-enzothiazol-6-yl}-amide

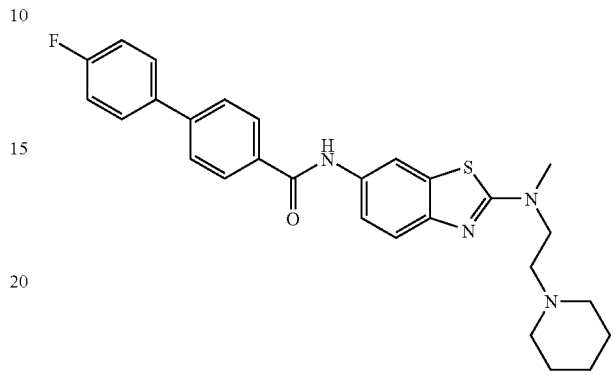

Mass spectrum (ion-spray): (m/z)=489.0 (M+1).

The following compounds, Intermediates 10 and 11, are prepared according to the procedure outlined in General Method A.

Intermediate 10

N,N-Diethyl-N'-methyl-N'-(5-nitro-benzooxazol-2-yl)-propane-1,3-diamine

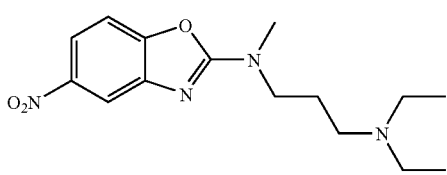

Mass spectrum (ion-spray): (m/z)=307.3 (M+1).

Intermediate 11

N,N,N'-Trimethyl-N'-(5-nitro-benzooxazol-2-yl)-propane-1,3-diamine

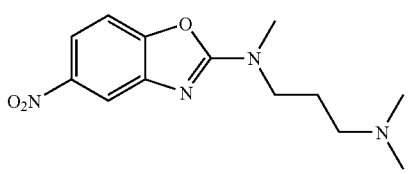

Mass spectrum (ion-spray): (m/z)=279.3 (M+1).

The following compounds, Intermediates 12 and 13, are prepared according to the procedure outlined in General Method B, utilizing the appropriate reagent or intermediate.

Intermediate 12

N²-(3-Diethylamino-propyl)-N²-methyl-benzooxazole-2,5-diamine

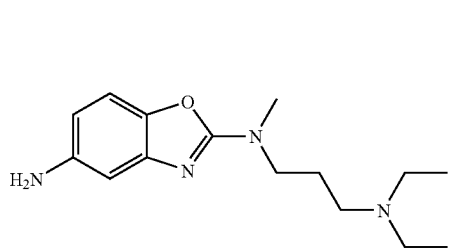

¹H NMR (400 MHz, CDCl₃): δ 6.99 (d, J=8.4 Hz, 1H), 6.69 (s, 1H), 6.32 (dd, J=2.4, 8.4 Hz, 1H), 3.54 (m, 4H), 3.15 (s, 3H), 2.53 (m, 6H), 1.02 (t, J=7.2 Hz, 6H).

Intermediate 13

N²-(3-Dimethylamino-propyl)-N²-methyl-benzooxazole-2,5-diamine

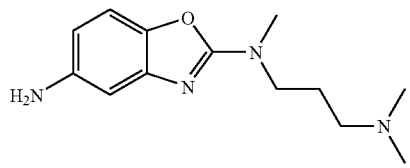

¹H NMR (400 MHz, CDCl₃): δ 6.99 (d, J=8.4 Hz, 1H), 6.69 (s, 1H), 6.32 (dd, J=2.4, 8.4 Hz, 1H), 3.55 (m, 4H), 3.16 (s, 3H), 2.33 (m, 2H), 2.23 (s, 6H).

The following compounds, Examples 71 and 72, are prepared according to the procedure outlined in General Method E utilizing an appropriate reagent and/or intermediate.

Example 71

N-{2-[Methyl-(1-methyl-pyrrolidin-3-ylmethyl)-amino]-benzooxazol-5-yl}-3-phenoxy-benzamide Hydrochloride, Isomer 1

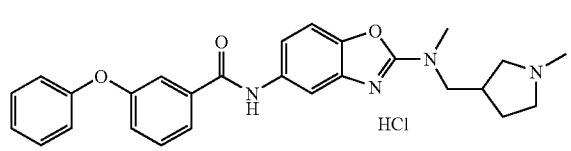

Mass spectrum (ion-spray): (m/z)=457.3 (M+1).

Example 72

N-{2-[Methyl-(1-methyl-pyrrolidin-3-ylmethyl)-amino]-benzooxazol-5-yl}-3-phenoxy-benzamide Hydrochloride, Isomer 2

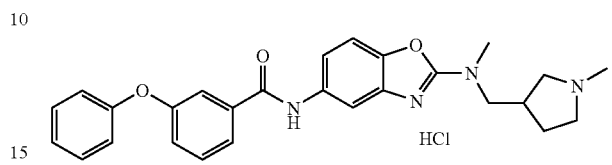

Mass spectrum (ion-spray): (m/z)=457.3 (M+1).

The following compounds, Examples 73 to 86, were prepared according to the procedure outlined in General Method C, utilizing appropriate reagents and/or intermediates:

Example 73

4'-Fluoro-biphenyl-4-carboxylic acid {2-[methyl-(1-methyl-pyrrolidin-3-ylmethyl)-amino]-benzooxazol-5-yl}-amide Hydrochloride, Isomer 1

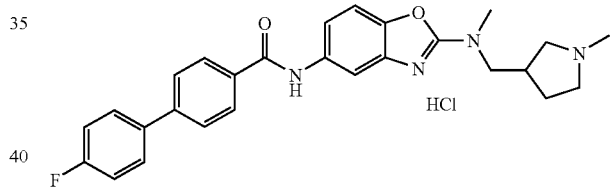

Mass spectrum (ion-spray): (m/z)=459.2 (M+1), Retention time 4.38 min.

Example 74

4'-Fluoro-biphenyl-4-carboxylic acid {2-[methyl-(1-methyl-pyrrolidin-3-ylmethyl)-amino]-benzooxazol-5-yl}-amide Hydrochloride, Isomer 2

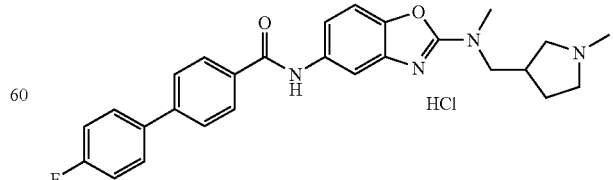

Mass spectrum (ion-spray): (m/z)=459.2 (M+1), Retention time=4.38 min.

Example 75

4'-Fluoro-biphenyl-4-carboxylic acid {2-[methyl-(1-methyl-piperidin-4-yl)-amino]-benzooxazol-5-yl}-amide Hydrochloride

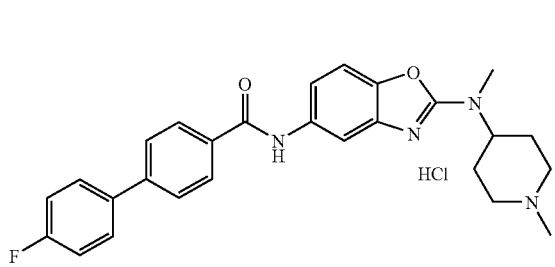

Mass spectrum (ion-spray): (m/z)=459.2 (M+1), Retention time=4.39 min.

Example 76

5-(4-Fluoro-phenyl)-pyridine-2-carboxylic Acid {2-[(2-dimethylamino-ethyl)-methyl-amino]-benzooxazol-5-yl}-amide Hydrochloride

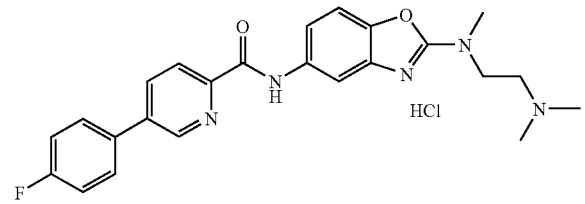

Mass spectrum (ion-spray): (m/z)=434.2 (M+1), Retention time=4.32 min.

Example 77

4'-Fluoro-biphenyl-4-carboxylic Acid {2-[(2-dimethylamino-ethyl)-methyl-amino]-benzooxazol-5-yl}-amide

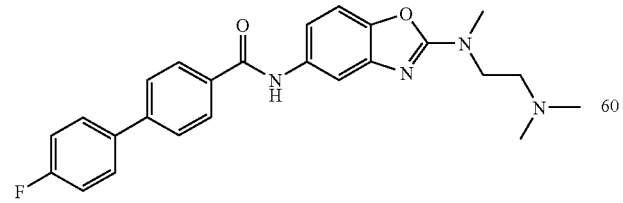

Mass spectrum (ion-spray): (m/z)=433.0 (M+1), Retention time=4.54 min.

Example 78

N-{2-[(2-Dimethylamino-ethyl)-methyl-amino]-benzooxazol-5-yl}-3-(4-trifluoromethyl-phenyl)-acrylamide

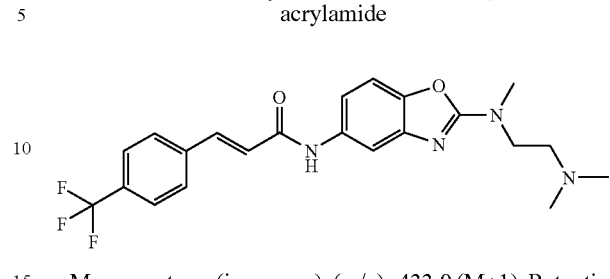

Mass spectrum (ion-spray): (m/z)=433.0 (M+1), Retention time=4.55 min.

Example 79

4-Cyclohexyl-N-{2-[(2-dimethylamino-ethyl)-methyl-amino]-benzooxazol-5-yl}-benzamide

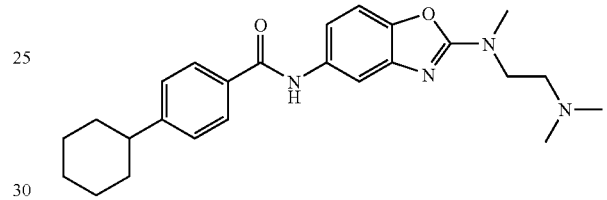

Mass spectrum (ion-spray): (m/z)=421.0 (M+1), Retention time=5.08 min.

Example 80

N-{2-[(3-Diethylamino-propyl)-methyl-amino]-benzooxazol-5-yl}-3-(4-trifluoromethyl-phenyl)-acrylamide

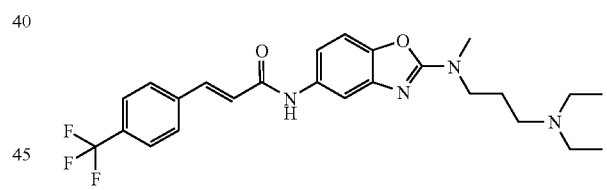

Mass spectrum (ion-spray): (m/z)=475.0 (M+1), Retention time=4.81 min.

Example 81

4'-Fluoro-biphenyl-4-carboxylic acid {2-[(3-diethylamino-propyl)-methyl-amino]-benzooxazol-5-yl}-amide

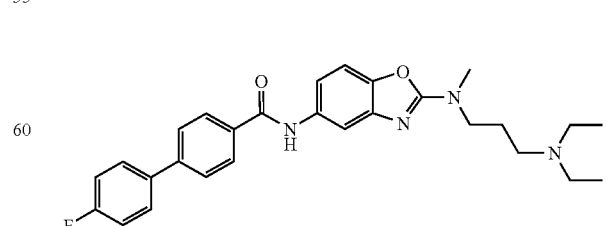

Mass spectrum (ion-spray): (m/z)=475.0 (M+1), Retention time=4.81 min.

Example 82

N-{2-[(3-Diethylamino-propyl)-methyl-amino]-benzooxazol-5-yl}-3-phenoxy-benzamide Hydrochloride

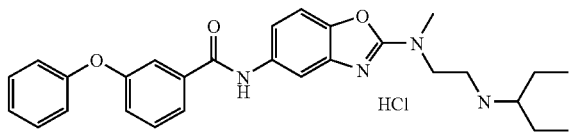

Mass spectrum (ion-spray): (m/z)=473.0 (M+1), Retention time=4.86 min.

Example 83

4-Cyclohexyl-N-{2-[(3-diethylamino-propyl)-methyl-amino]-benzooxazol-5-yl}-benzamide Hydrochloride

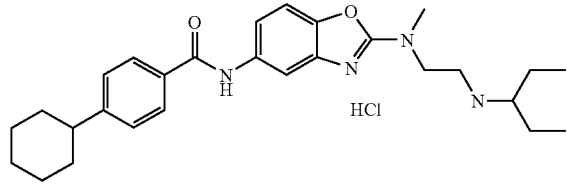

Mass spectrum (ion-spray): (m/z)=463.2 (M+1), Retention time=4.86 min.

Example 84

4-Cyclohexyl-N-{2-[(3-dimethylamino-propyl)-methyl-amino]-benzooxazol-5-yl}-benzamide

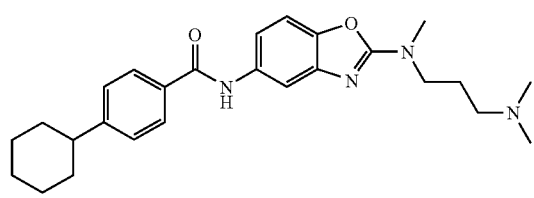

Mass spectrum (ion-spray): (m/z)=435.2 (M+1), Retention time=5.15 min.

Example 85

N-{2-[(3-Dimethylamino-propyl)-methyl-amino]-benzooxazol-5-yl}-3-(4-trifluoromethyl-phenyl)-acrylamide

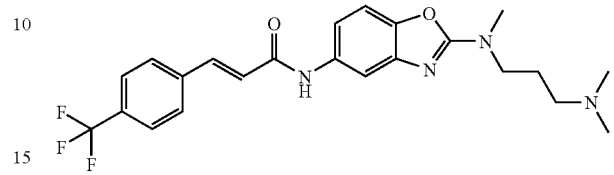

Mass spectrum (ion-spray): (m/z) 447.0 (M+1), Retention time=4.68 min.

Example 86

N-{2-[(3-Dimethylamino-propyl)-methyl-amino]-benzooxazol-5-yl}-3-phenoxy-benzamide Hydrochloride

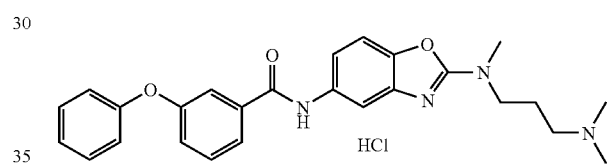

Mass spectrum (ion-spray): (m/z)=445.0 (M+1), Retention time=4.67 min.

Example 87

4'-Fluoro-biphenyl-4-carboxylic acid {2-[(3-diethylamino-propyl)-methyl-amino]-benzothiazol-6-yl}-amide Hydrochloride

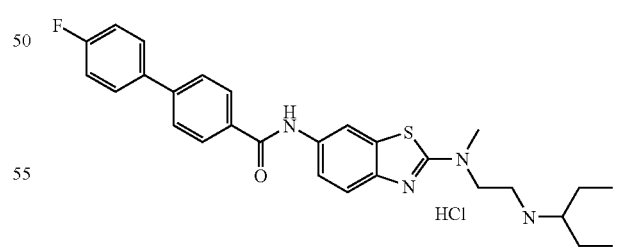

The title compound is prepared according to the general procedure outlined in Example 31, Step 3 to yield 2.04 g (98%) of product: Mass spectrum (ion-spray): (m/z)=491.3 (M+1), Retention time=4.71 min.

The following compounds, Examples 88 to 97 are prepared according to the procedure outlined in General Method F using the appropriate intermediates.

Example 88

3',4'-Dichloro-biphenyl-4-carboxylic acid {2-[(2-dimethylamino-ethyl)-methyl-amino]-benzothiazol-6-yl}-amide

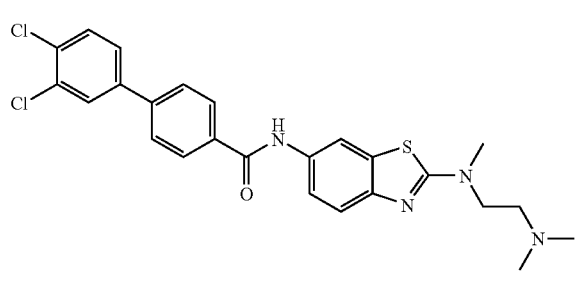

Mass spectrum (ion-spray): (m/z)=499.0 (M+1), Retention time=5.28 min.

Example 89

Biphenyl-4-carboxylic Acid {2-[(2-dimethylamino-ethyl)-methyl-amino]-benzothiazol-6-yl}-amide

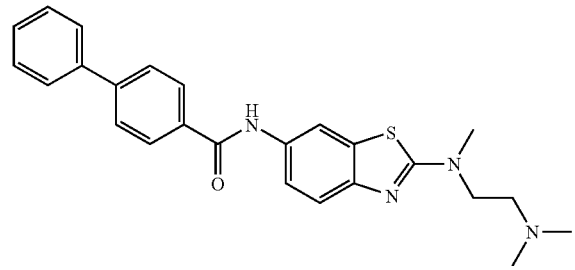

Mass spectrum (ion-spray): (m/z)=431.0 (M+1), Retention time=4.53 min.

Example 90

5-(4-Fluoro-phenyl)-thiophene-2-carboxylic Acid {2-[(2-dimethylamino-ethyl)-methyl-amino]-benzothiazol-6-yl}-amide

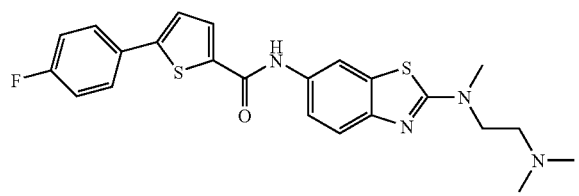

Mass spectrum (ion-spray): (m/z) 455.0 (M+1), Retention time=4.61 min.

Example 91

N-{2-[(2-Dimethylamino-ethyl)-methyl-amino]-benzothiazol-6-yl}-6-(4-fluoro-phenyl)-nicotinamide

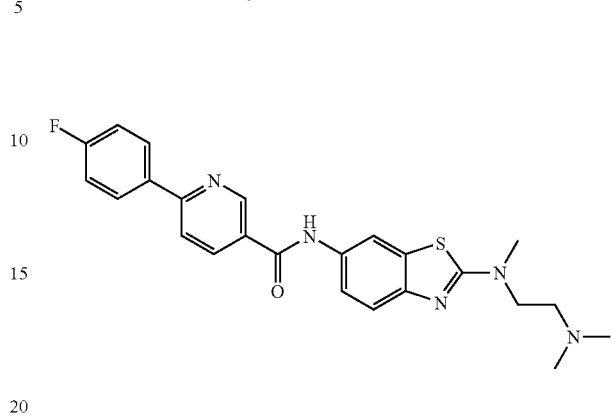

Mass spectrum (ion-spray): (m/z)=450.0 (M+1), Retention time=4.17 min.

Example 92

5-Phenyl-thiophene-2-carboxylic acid {2-[(2-dimethylamino-ethyl)-methyl-amino]-benzothiazol-6-yl}-amide

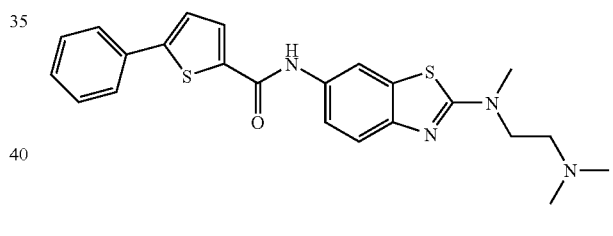

Mass spectrum (ion-spray): (m/z)=437.0 (M+1), Retention time=4.51 min.

Example 93

4-Butyl-N-{2-[(2-dimethylamino-ethyl)-methyl-amino]-benzothiazol-6-yl}-benzamide Hydrochloride

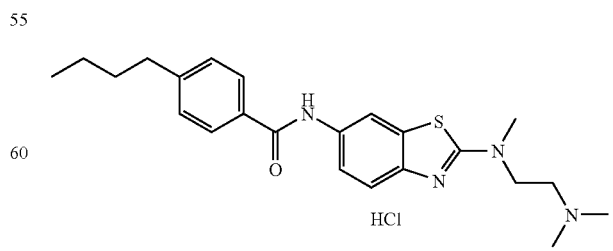

Mass spectrum (ion-spray): (m/z)=411.2 (M+1), Retention time=4.74 min.

Example 94

N-{2-[(2-Dimethylamino-ethyl)-methyl-amino]-benzothiazol-6-yl}-6-phenyl-niotinamide

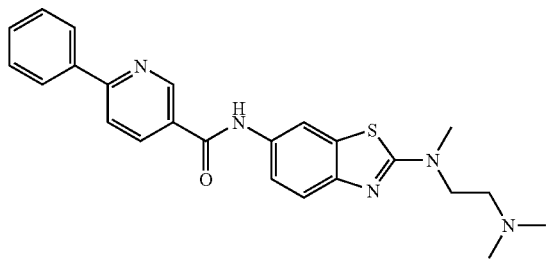

Mass spectrum (ion-spray): (m/z)=432.0 (M+1), Retention time=4.00 min.

Example 95

4'-Fluoro-biphenyl-4-carboxylic Acid {2-[(3-dimethylamino-propyl)-methyl-arm-o]-benzothiazol-6-yl}-amide

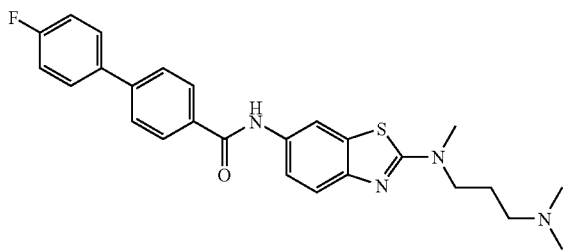

Mass spectrum (ion-spray): (m/z)=463.0 (M+1), Retention time=4.62 min.

Example 96

N-{2-[(3-Dimethylamino-propyl)-methyl-amino]-benzothiazol-6-yl}-3-(4-fluoro-phenyl)-acrylamide

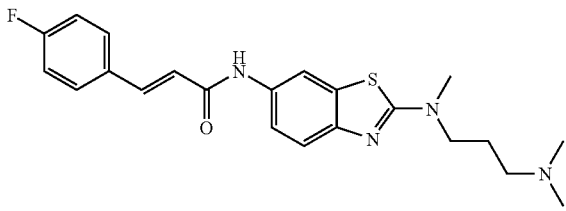

Mass spectrum (ion-spray): (m/z)=413.0 (M+1), Retention time=4.02 min.

Example 97

4'-Fluoro-biphenyl-4-carboxylic acid {2-[(2-diethylamino-ethyl)-methyl-amino]-benzothiazol-6-yl}-amide

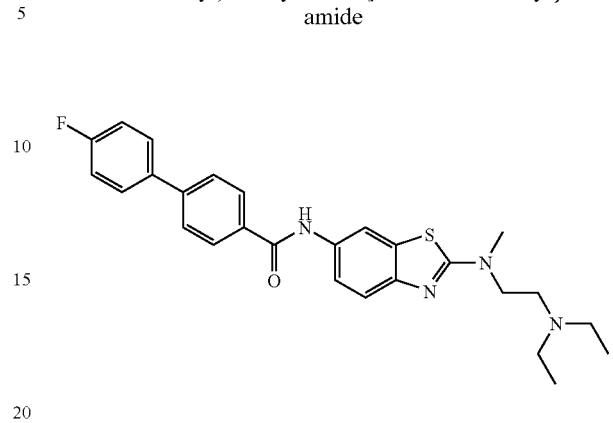

Mass spectrum (ion-spray): (m/z)=477.0 (M+1), Retention time=4.72 min.

Example 98

N-(2-Chloro-benzothiazol-6-yl)-3-(4-fluoro-phenyl)-acrylamide

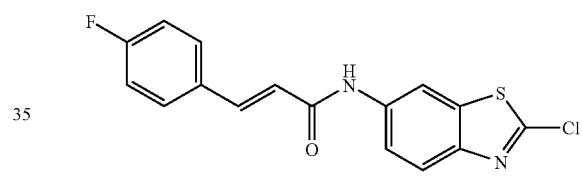

The title compound is prepared according to the general procedure outlined in Example 31, Step 2 to yield 5.80 g (37%) of product: $^1$H NMR (400 MHz, DMSO): δ 8.58 (s, 1H), 7.90 (d, J=8.8 Hz, 1H), 7.67 (m, 4H), 7.62 (d, J=15.6 Hz, 1H), 7.27 (t, J=8.8 Hz, 2H), 6.78 (d, J=15.6 Hz, 6H), 1.02 (t, J=7.2 Hz, 6H).

The following compounds, Examples 99 to 103, are prepared according to the general procedure outlined in Example 31, Step 3 using appropriate reagents and/or intermediates.

Example 99

3-(4-Fluoro-phenyl)-N-{2-[methyl-(1-methyl-pyrrolidin-3-ylmethyl)-amino]-benzothiazol-6-yl}-acrylamide, Isomer 1

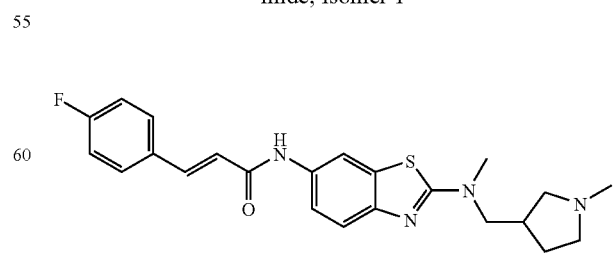

Mass spectrum (ion-spray): (m/z)=425.0 (M+1), Retention time=4.

Example 100

3-(4-Fluoro-phenyl)-N-{2-[methyl-(1-methyl-pyrrolidin-3-ylmethyl)-amino]-benzothiazol-6-yl}-acrylamide, Isomer 2

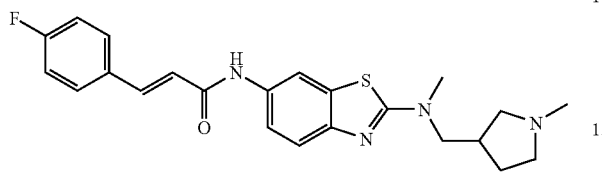

Mass spectrum (ion-spray): (m/z)=425.0 (M+1), Retention time 4.

Example 101

N-[2-(2-Dimethylamino-ethylamino)-benzothiazol-6-yl]-3-(4-fluoro-phenyl)-acrylamide

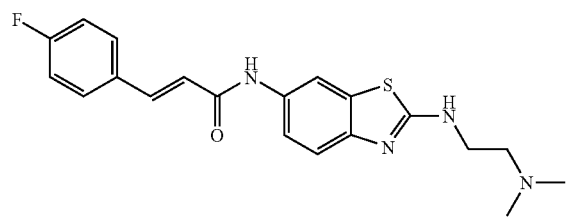

Mass spectrum (ion-spray): (m/z)=485.3 (M+1).

Example 102

4'-Fluoro-biphenyl-4-carboxylic acid [2-(2-dimethylamino-ethylamino)-benzothiazol-6-yl]-amide

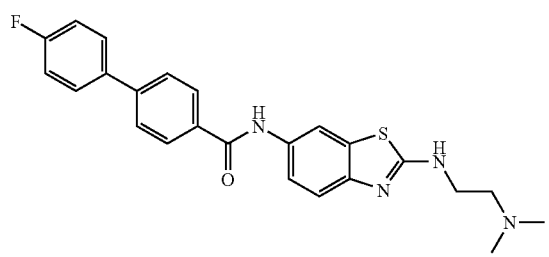

Mass spectrum (ion-spray): (m/z)=435.0 (M+1), Retention time 4.35 min.

Example 103

4'-Fluoro-biphenyl-4-carboxylic acid {2-[methyl-1-methyl-piperidin-4-yl)-amino]-benzothiazol-6-yl}-amide

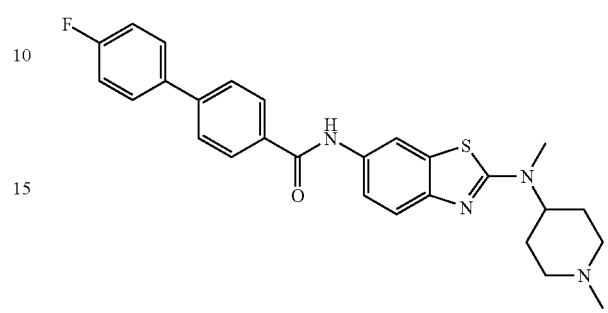

Mass spectrum (ion-spray): (m/z)-475.0 (M+1), Retention time=4.58 min.

The following compounds, Examples 104 to 107, are prepared according to the procedure outlined in General Method G using the appropriate intermediates and/or reagents.

Example 104

4'-Fluoro-biphenyl-4-carboxylic acid {2-[methyl-(1-methyl-pyrrolidin-3-ylmethyl)-amino]-benzothiazol-6-yl}-amide Hydrochloride (Isomer 2)

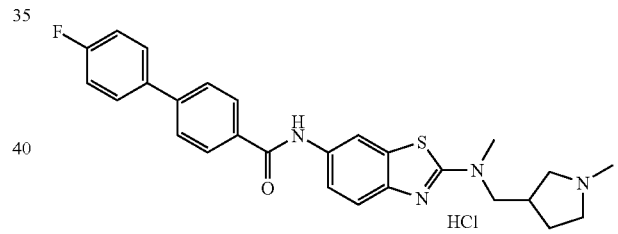

Mass spectrum (ion-spray): (m/z)=475.3 (M+1), Retention time=4.56 min.

Example 105

4'-Fluoro-biphenyl-4-carboxylic acid {2-[methyl-(1-methyl-pyrrolidin-3-ylmethyl)-amino]-benzothiazol-6-yl}-amide (Isomer 1)

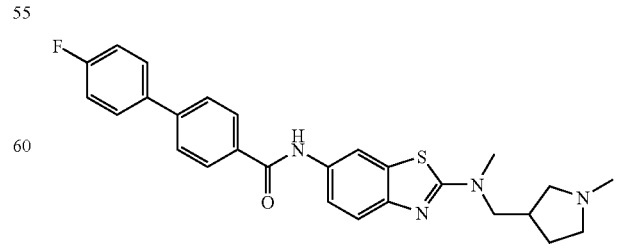

Mass spectrum (ion-spray): (m/z)=475.0 (M+1), Retention time=4.61 min.

Example 106

4'-Fluoro-biphenyl-4-carboxylic Acid {2-[methyl-(1-methyl-pyrrolidin-3-yl)-amino]-benzothiazol-6-yl}-amide (Isomer 1)

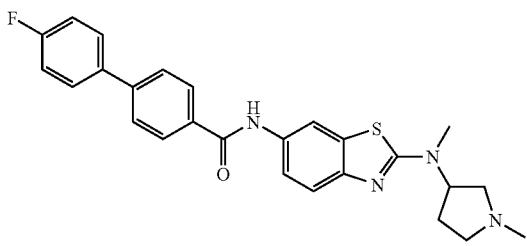

Mass spectrum (ion-spray): (m/z)=461.0 (M+1), Retention time=4.59 min.

Example 107

4'-Fluoro-biphenyl-4-carboxylic Acid {2-[methyl-(1-methyl-pyrrolidin-3-yl)-amino]-benzothiazol-6-yl}-amide (Isomer 2)

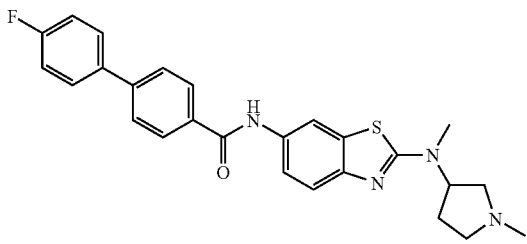

Mass spectrum (ion-spray): (m/z)=461.0 (M+1), Retention time=4.60 min.

Example 108

4'-Fluoro-biphenyl-4-carboxylic acid (2-[(2-dimethylamino-ethyl)-methyl-amino]-7-methyl-benzothiazol-6-yl)-amide

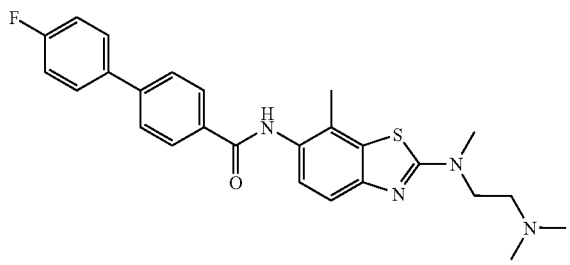

Step 1. 7-Methyl-6-nitro-benzothiazol-2-ylamine

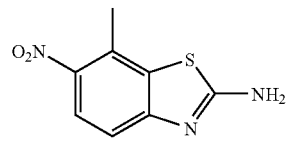

Place 3-methyl-4-nitro-phenylamine (14.60 g, 96.1 mmol) and potassium thiocyanate (34.70 g, 357.1 mmol) in acetic acid (250 mL). Stir vigorously and add bromine (5.0 mL, 97.6 mmol) dissolved in acetic acid (50 mL) dropwise. Stir at rt (room temperature). overnight. Concentrate in vacuo, dilute with DCM, and wash with 1N NaOH. Collect the organic layer and concentrate in vacuo. Triturate the residue with water and then dry in a vacuum oven at 45° C. overnight to yield 10.12 g (50%) of a 5:2 ratio of desired product:regioisomer: $^1$H NMR (400 MHz, DMSO) δ 8.18 (bs, 2H), 7.95 (d, J=8.8 Hz, 1H), 7.28 (d, J=3.2 Hz, 1H), 2.61 (s, 3H).

Step 2. 2-Chloro-7-methyl-6-nitro-benzothiazole

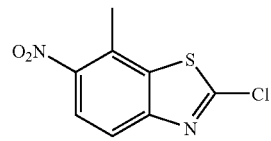

Suspend 7-methyl-6-nitro-benzothiazol-2-ylamine (5.17 g, 24.7 mmol) in conc. HCl (70 mL) and water (70 mL). Add copper (1) chloride (542 mg, 5.47 mmol) followed by slow addition of sodium nitrite (17.4 g, 252 mmol). Stir at rt for 2 h and then add water (100 mL). Filter the solid and dry in a vacuum oven at 40° C. overnight to yield 4.45 g (79%) of the title compound: $^1$H NMR $δ_H$ (400 MHz, DMSO) 8.16 (d, J=9.2 Hz, 1H), 8.01 (d, J=8.8 Hz, 1H), 2.71 (s, 3H).

Step 3. N,N,N'-Trimethyl-N-1-(7-methyl-6-nitro-benzothiazol-2-yl)-ethane-1,2-diamine

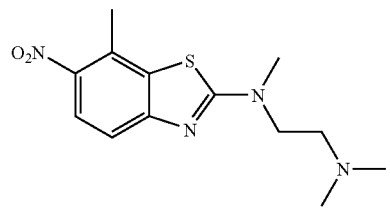

The title compound is prepared according to the procedure outlined in Example 1, Step 2 to yield 2.55 g (78%) of product: mass spectrum (ion-spray): (m/z)=295.1 (M+1).

Step 4. N,N,N'-Trimethyl-N'-(6-amino-7-methyl-benzothiazol-2-yl)-ethane-1,2-diamine

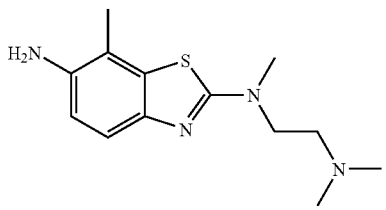

The title compound is prepared according to the procedure outlined in Example 1, Step 3 to yield 2.22 g (78%) of product. $^1$H NMR (400 MHz, CDCl$_3$): δ 7.25 (m, 1H), 6.69 (d, J=8.4 Hz, 1H), 3.63 (m, 2H), 3.47 (bs, 2H), 3.18 (s, 3H), 2.64 (bs, 2H), 2.34 (s, 6H), 2.27 (s, 3H).

Step 5. 4'-Fluoro-biphenyl-4-carboxylic acid {2-[(2-dimethylamino-ethyl)-methyl-amino]-7-methyl-benzothiazol-6-yl}-amide

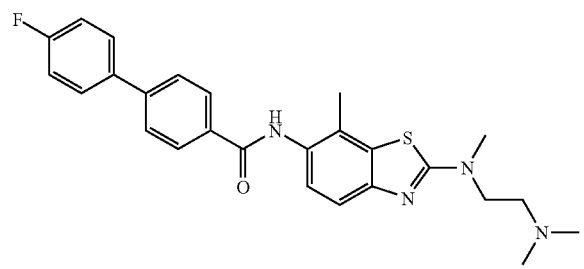

The title compound is prepared from the product of Step 4 above according to the procedure outlined in General Method G to yield 54 mg (4%) of the product: Mass spectrum (ion-spray): (m/z)=463.0 (M+1), Retention time=4.51 min.

Example 109

5-(4-Fluoro-phenyl)-pyrazine-2-carboxylic acid {2-[(2-dimethylamino-ethyl)-methyl-amino]-benzothiazol-6-yl}-amide

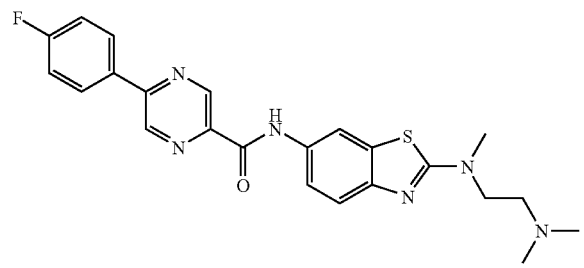

Step 1. 5-Chloro-pyrazine-2-carboxylic acid {2-[(2-dimethylamino-ethyl)-methyl-amino]-benzothiazol-6-yl}-amide

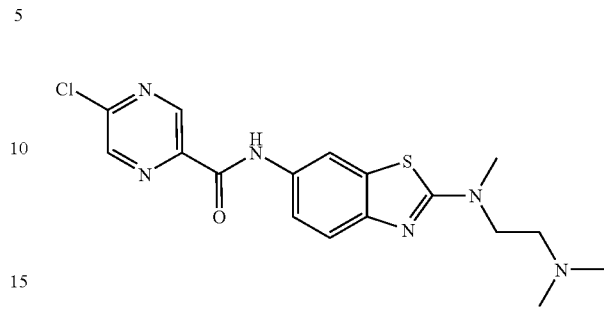

The title compound is prepared according to the procedure of General Method F using appropriate reagents and intermediates disclosed herein or known to one of skill in the art. Mass spectrum (ion-spray): (m/z)=391.0 (M+1).

Step 2

Place 5-chloro-pyrazine-2-carboxylic acid {2-[(2-dimethylamino-ethyl)-methyl-amino]-benzothiazol-6-yl}-amide (73 mg, 0.187 mmol), Pd(PPh$_3$)$_4$ (29 mg, 0.025 mmol), 4-fluorophenyl boronic acid (27 mg, 0.193 mmol), and potassium carbonate (134 mg, 0.97 mmol) in a solution of 1,4-dioxane (5 mL) and water (1 mL): Heat the reaction to reflux overnight. Chromatograph (silica gel, eluting with 7-17% MeOH:DCM) to yield 21 mg (25%) of the title compound. mass spectrum (ion-spray): (m/z)=503.0 (M+1). Retention time=4.51 min.

Example 110

N-{2-[(2-Dimethylamino-ethyl)-methyl-amino]-benzothiazol-6-yl}-3-phenoxy-benzamide

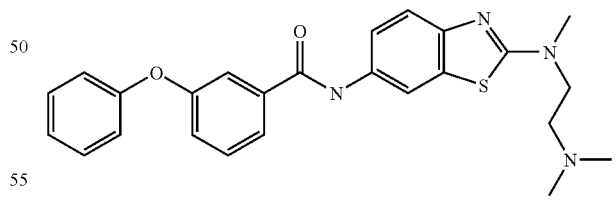

The title compound is prepared by following General Method A, using 3-phenoxy-benzoic acid (0.22 g, 1.04 mmol), and N*2*-(2-dimethylamino-ethyl)-N*2*-methyl-benzothiazole-2,6-diamine (0.20 g, 0.80 mmol) to afford an off-white solid (0.19 g, 53%). LC/MS: Retention time=4.45 nm in; (m/z): calcd for C$_{25}$H$_2$(N$_4$O$_2$S (M+H)$^+$: 447.6; found: 447.3.

Example 111

4-Cyclohexyl-N-{2-[(2-dimethylamino-ethyl)-methyl-amino]-benzothiazol-6-yl}-benzamide

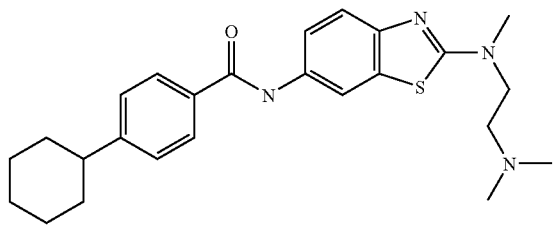

The title compound is prepared by following General Method A, using 4-cyclohexyl-benzoic acid (0.16 g, 0.78 mmol), and N*2*-(2-Dimethylamino-ethyl)-N*2*-methyl-benzothiazole-2,6-diamine (0.15 g, 0.60 mmol) to afford a white solid (0.076 g, 29%). LC/MS: Retention time 5.00 min; (m/z): calcd for $C_{25}H_{32}N_4OS$ (M+H)$^+$: 437.6; found: 437.0.

Example 112

N-{2-[(2-Dimethylamino-ethyl)-methyl-amino]-benzothiazol-6-yl}-4-thiophen-2-yl-benzamide

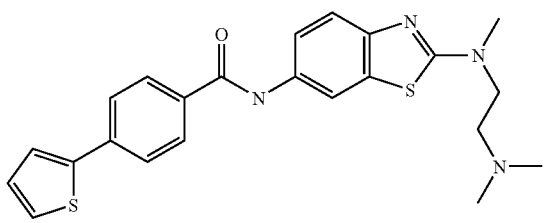

The title compound is prepared by following General Method A, using 4-thiophen-2-yl-benzoic acid (0.098 g, 0.48 mmol), and N*2*-(2-dimethylamino-ethyl)-N*2*-methyl-benzothiazole-2,6-diamine (0.10 g, 0.40 mmol) to afford the title compound as a white solid. LC/MS: Retention time=4.37 min; (m/z): calcd for $C_{23}H_{24}N_4OS_2$ (M+H)$^+$: 437.6; found: 437.3.

Example 113

2-Methyl-biphenyl-4-carboxylic Acid {2-[(2-dimethylamino-ethyl)-methyl-amino]-benzothiazol-6-yl}-amide Step 1. 2-Methyl-biphenyl-4-carboxylic Acid Methyl Ester

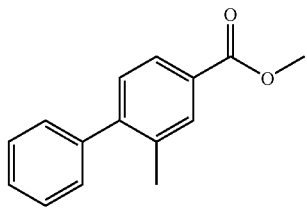

A solution of 4-bromo-3-methyl-benzoic acid methyl ester (1.0 g, 4.36 mmol) and phenylboronic acid (0.64 g, 5.24 mmol) in n-PrOH (15 mL) is treated with 2 M $Na_2CO_3$ (4.4 mL), and purged with $N_2$ for 10 min, and $Pd(PPh_3)_4$ (25 mg, 0.22 mmol) is then added. The reaction is refluxed overnight. Organic solvent is removed in vacuo, the residue is extracted with $CH_2Cl_2$ (30 mL), washed with 10% $Na_2CO_3$ (30 mL), $H_2O$ (30 mL); dried with $Na_2SO_4$ and concentrated. Purification of the crude material by chromatography affords the title compound (0.10 g, 10%).

Step 2. 2-Mehyl-biphenyl-4-carboxylic Acid

A solution of 2-methyl-biphenyl-4-carboxylic acid methyl ester (0.10 g, 0.44 mmol) in $CH_3OH$ (5 mL) and $H_2O$ (0.5 mL) is reacted with NaOH (88 mg, 2.2 mmol) at reflux for 2 h. Organic solvent is removed in vacuo, the residue is diluted with $H_2O$, and extracted with $Et_2O$. The aqueous layer is acidified with 5 M HCl, extracted with $Et_2O$, dried with $MgSO_4$, filtered and concentrated to give the title compound as a white solid (72 mg, 77%).

Step 3. 2-Methyl-biphenyl-4-carboxylic Acid {2-[(2-dimethylamino-ethyl)-methyl-amino]-benzothiazol-6-yl}-amide The title compound is prepared by following General Method A, using 2-methyl-biphenyl-4-carboxylic acid (0.072 g, 0.34 mmol), and N*2*-(2-dimethylamino-ethyl)-N*2*-methyl-benzothiazole-2,6-diamine (0.065 g, 0.26 mmol) to give 0.036 g, (31%) of product. LC/MS: Retention time=4.80 min; (m/z): calcd for $C_2H_{28}N_4OS$ (M+H)$^+$: 445.6; found: 445.0.

Example 114

4-Cyclopentyl-N-{2-[(2-dimethylamino-ethyl)-methyl-amino]-benzothiazol-6-yl}-benzamide Step 1. 4-Cyclopent-1-enyl-benzoic Acid

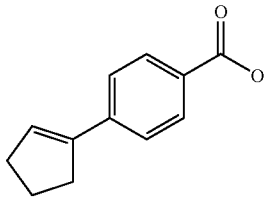

In a sealed tube is added 4-iodobenzoic acid (5.0 g, 20.16 mmol), cyclopentene (17.8 mL, 2101.6 mmol), Et₃N (8.4 mL, 60.48 mmol) in toluene (100 mL). It is purged with N₂ for 15 min. Pd(OAc)₂ (0.23 g, 1.01 mmol) and P(o-Tol)₃ (0.61 g, 2.01 mmol) are added. The reaction is stirred at 120° C. overnight. It is diluted with EtOAc, washed with 1M HCl, H₂O, and brine. Purification of the crude material by chromatography gives the title compound (2.63 g, 69%).

Step 2. 4-Cyclopentyl-benzoic Acid

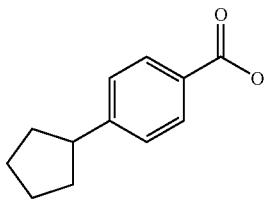

A solution of 4-cyclopent-1-enyl-benzoic acid (2.6 g, 13.8 mmol) in EtOH (20 mL) is hydrogenated with 10% Pd/C (0.25 g) at 20 psi H₂ for 2 h. It is filtered through Celite® and concentrated to give 2.46 g (95%) of the title compound. LC/MS (m/z): calcd for $C_{12}H_{14}O_2$ (M−H)⁻: 189.2; found: 189.2.

Step 3. 4-Cyclopentyl-N-{2-[(2-dimethylamino-ethyl)-methyl-amino]-benzothiazol-6-yl}-benzamide

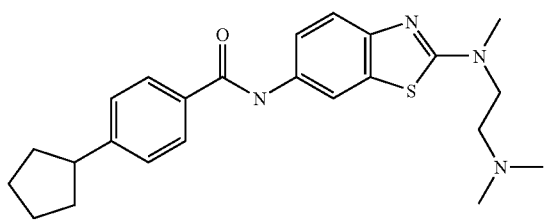

The title compound is prepared by following General Method A, using 4-cyclopentyl-benzoic acid (0.099 g, 0.52 mmol), and N*2*-(2-Dimethylamino-ethyl)-N*2*-methyl-benzothiazole-2,6-diamine (0.10 g, 0.40 mmol) to give 0.38 g (23%) of product. LC/MS: Retention time=4.97 min; (m/z): calcd for $C_{24}H_{30}N_4OS$ (M+H)⁺: 423.6; found: 423.0.

Example 115

4-Cyclohex-2-enyl-N-(2-[(2-dimethylamino-ethyl)-methyl-amino]-benzothiazol-6-yl)-benzamide Step 1. 4-Cyclohex-2-enyl-benzoic Acid

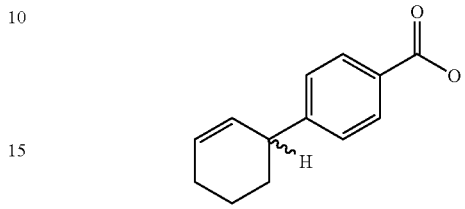

The title compound is prepared by following a procedure analogous to Example 114, Step 1, and using 4-iodobenzoic acid (3.0 g, 12.10 mmol), and cyclohexene (12.3 mL) to give the product (0.40 g, 1.98 mmol, 16%).

Step 2. 4-Cyclohex-2-enyl-N-{2-[(2-dimethylamino-ethyl)-methyl-amino]-benzothiazol-6-yl}-benzamide

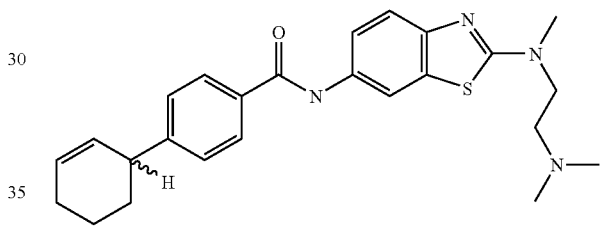

The title compound is prepared by following General Method A, using 4-cyclohex-2-enyl-benzoic acid (0.079 g, 0.39 mmol), and N*2*-(2-Dimethylamino-ethyl)-N*2*-methyl-benzothiazole-2,6-diamine (0.73 g, 0.30 mmol) to give the product (0.041 g, 31%). LC/MS: Retention time=5.09 min; (m/z): calcd for $C_{25}H_{30}N_4OS$ (M+H)⁺: 435.6; found: 435.0.

Example 116

2'-Chloro-4'-methoxy-biphenyl-4-carboxylic acid {2-[methyl-(1-methyl-pyrrolidin-3-yl)-amino]-benzothiazol-6-yl}-amide Step 1. 2'-Chloro-4'-methoxy-biphenyl-4-carboxylic Acid Methyl Ester

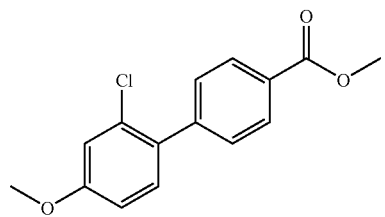

The title compound is prepared by following a procedure analogous to Example 113, Step 1, using 1-bromo-2-chloro-4-methoxy-benzene (10.0 g, 45.15 mmol) and 4-boronic acid-benzoic methyl ester (8.94 g, 49.67 mmol) to give 6.3 g (50.4%) of product. LC/MS (m/z): calcd for $C_{15}H_{13}ClO_3$ (M+H)$^+$: 277.7; found: 277.2.

Step 2. 2'-Chloro-4'-methoxy-biphenyl-4-carboxylic Acid

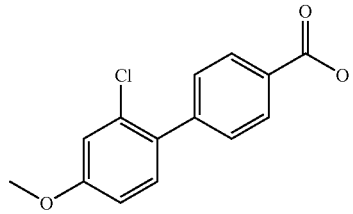

The title compound is prepared by following a procedure analogous to Example 113, Step 2, using 2'-chloro-4'-methoxy-biphenyl-4-carboxylic acid methyl ester (1.92 g, 6.94 mmol) to afford 1.65 g (91%) of product.

Step 3. 2'-Chloro-4'-methoxy-biphenyl-4-carboxylic acid {2-[methyl-(1-methyl-pyrrolidin-3-yl)-amino]-benzothiazol-6-yl}-amide

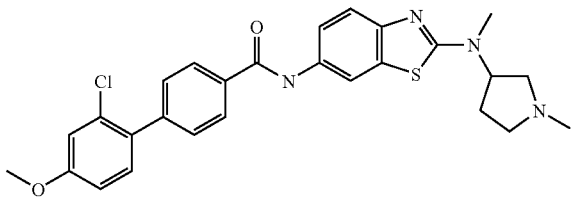

The title compound is prepared by following Method A, using 2'-chloro-4'-methoxy-biphenyl-4-carboxylic acid (0.26 g, 0.99 mmol), and isomer-1 of N*2*-Methyl-N*2*-(1-methyl-pyrrolidin-3-yl)-benzothiazole-2,6-diamine (0.20 g, 0.76 mmol) to afford the product (0.125 g, 32%). LC/MS: Retention time=5.27 min; (m/z): calcd for $C_{27}H_{27}ClN_4O_2S$. m/e: 507.1; found: 507.0.

Example 117

4'-Fluoro-biphenyl-4-carboxylic acid {2-[methyl-(1-methyl-pyrrolidin-3-yl)-amino]-benzothiazol-6-yl}-amide Hydrochloride Salt

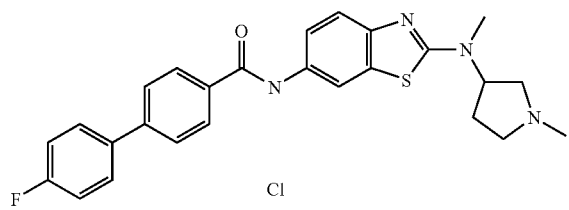

The title compound is prepared by following Method C, using 4'-fluoro-biphenyl-4-carboxylic acid (3.46 g, 16.01 mmol), oxalyl chloride (4.65 mL, 53.36 mmol) and isomer-2 of N*2*-methyl-N*2*-(1-methyl-pyrrolidin-3-yl)-benzothiazole-2,6-diamine (2.80 g, 10.76 mmol) to give 4'-fluoro-biphenyl-4-carboxylic acid {2-[methyl-(1-methyl-pyrrolidin-3-yl)-amino]-benzothiazol-6-yl}-amide (2.41 g, 49%). The material is dissolved in THF (100 mL), and 1.0 M HCl in EtOH is added to adjusted the pH to 1. The resulting solid is collected and recrystallized from EtOH/Heptane to give 2.03 g (78%). LC/MS: Retention time=5.06 min; (m/z): calcd for, C26H25FN4OS (M+H)$^+$: 461.6; found: 461.0.

Example 118

4-Cyclohexyloxy-N-{2-[(2-dimethylamino-ethyl)-methyl-amino]-benzothiazol-6-yl}-benzamide

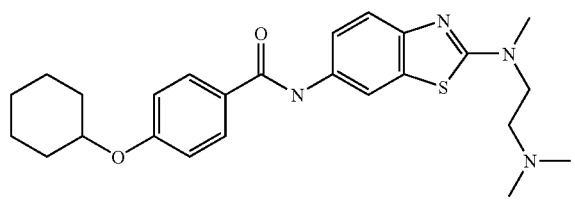

The title compound is prepared by following Method A, using 4-cyclohexyloxy benzoic acid (0.20 g, 0.91 mmol), and N*2*-(2-Dimethylamino-ethyl)-N*2*-methyl-benzothiazole-2,6-diamine (0.17 g, 0.68 mmol) to afford the 0.15 g (36%). LC/MS: Retention time=5.23 min; (m/z): calcd for $C_{25}H_{32}N_4O_2S$: 453.6; found: 453.0.

Example 119

4-Cyclohexylmethoxy-N-{2-[(2-dimethylamino-ethyl)-methyl-amino]-benzothiazol-6-yl}-benzamide

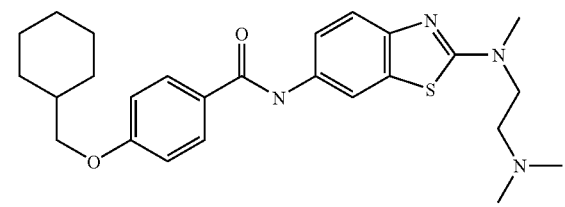

The title compound is prepared by following Method A, using 4-cyclohexylmethoxy-benzoic acid (Crooks, S. L.; Merrill, B. A.; Wightman, P. D. WO 9603983 A1.) (0.20 g, 0.86 mmol), and N*2*-(2-dimethylamino-ethyl)-N*2*-methyl-benzothiazole-2,6-diamine (0.17 g, 0.68 mmol) to afford 0.12 g (38%). LC/MS: Retention time=5.67 min; (m/z): calcd for $C_{26}H_{34}N_4O_2S$ (M+H)$^+$: 467.7; found: 467.0.

Example 120

2',4'-dichloro-biphenyl-4-carboxylic acid (2-[(2-dimethylamino-ethyl)-methyl-amino]-benzothiazol-6-yl)-amide Hydrochloride Salt Step 1. 2',4'-Dichloro-biphenl-4-carboxylic Acid

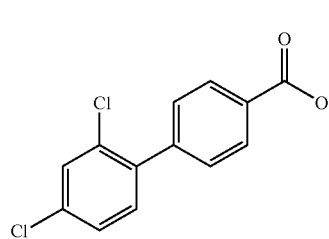

A solution of 2,4-dichlorophenyl boronic acid (3.96 g, 15.11 mmol) and 4-Iodo-benzoic acid methyl ester (2.88 g, 15.11 mmol), $K_2CO_3$ (7.31 g, 52.89 mmol) in 1,4-dioxane (85 mL), and water (20 mL) is purged with nitrogen for 10 min. $Pd(PPh_3)_4$ (0.87 g, 0.756 mmol) is added and the resulting reaction mixture is refluxed overnight. The reaction is diluted with water and extracted with $Et_2O$. The combined organic layers are washed with water, dried with $MgSO_4$, and concentrated. The crude material is purified by chromatography to give the title compound (2.20 g, 50%). LC/MS (m/z): calcd for $C_{13}H_{18}Cl_2O_2$: 267.1; found: 266.9.

Step 2. 2',4'-Dichloro-biphenyl-4-carboxylic acid {2-[(2-dimethylamino-ethyl)-methyl-amino]-benzothiazol-6-yl}-amide Hydrochloride Salt

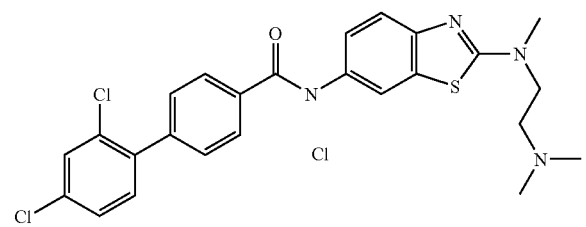

The title compound is prepared by following Method C, using 2',4'-dichloro-biphenyl-4-carboxylic acid (6.40 g, 23.97 mmol), $(COCl)_2$ (7.0 mL, 79.9 mmol) and N*2*-(2-dimethylamino-ethyl)-N*2*-methyl-benzothiazole-2,6-diamine (4.0 g, 15.9 mmol) top afford 2',4'-dichloro-biphenyl-4-carboxylic acid {2-[(2-dimethylamino-ethyl)-methyl-amino]-benzothiazol-6-yl}-amide (4.19 g, 54%). The material is dissolved in THF (100 mL), and followed by addition of 1.0 M HCl in EtOH (8.5 mL). The resulting solid is collected to give the 4.27 g (93%) of the hydrochloride salt. LC/MS, Retention time=5.17 min; (m/z): calcd for $C_{25}H_{24}Cl_2N_4OS$ 499.5; found: 499.0.

Example 121

2'-Chloro-4'-ethoxy-biphenyl-4-carboxylic Acid {2-[(2-dimethylamino-ethyl)-methyl-amino]-benzothiazol-6-yl}-amide Hydrochloride Salt

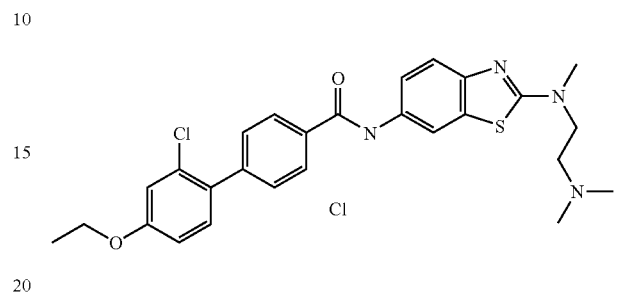

Step 1. 2'-Chloro-4'-ethoxy-biphenyl-4-carboxylic Acid Methyl Ester

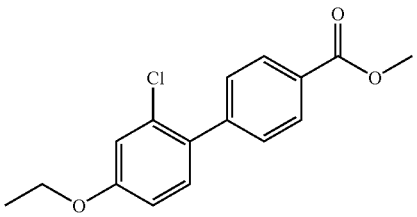

The title compound is prepared by following a procedure analogous to Example 113, Step 1, using 1-bromo-2-chloro-4-ethoxy-benzene (2.65 g, 11.25 mmol) and 4-boronic acid-benzoic methyl ester (2.23 g, 12.28 mmol) to afford 2.34 g (72%). LC/MS (m/z): calcd for $C_{16}H_{15}ClO_3$ (M+H)$^+$: 291.8; found: 291.3.

Step 2. 2'-Chloro-4'-ethoxy-biphenyl-4-carboxylic Acid.

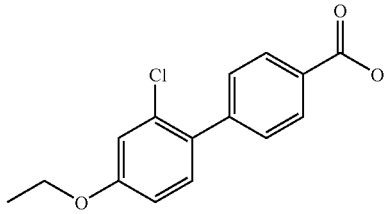

The title compound is prepared by following a procedure analogous to Example 113, Step 2, using 2'-chloro-4'-ethoxy-biphenyl-4-carboxylic acid methyl ester (2.34 g, 8.07 mmol) to afford 1.21 g (54%). LC/MS (m/z): calcd for $C_{15}H_{13}ClO_3$ (M−H)$^−$: 275.7; found: 275.3.

Step 3. 2'-Chloro-4'-ethoxy-biphenyl-4-carboxylic acid {2-[(2-dimethylamino-ethyl)-methyl-amino]-benzothiazol-6-yl}-amide Hydrochloride Salt

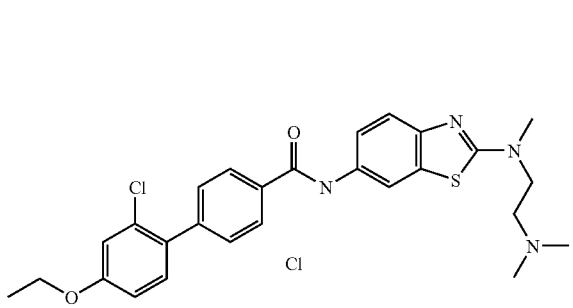

The title compound is prepared by following Method A, using 2'-chloro-4'-ethoxy-biphenyl-4-carboxylic acid (0.48 g, 1.73 mmol), and N*2*-(2-dimethylamino-ethyl)-N*2*-methyl-benzothiazole-2,6-diamine (0.33 g, 1.33 mmol) to afford 2'-chloro-4'-ethoxy-biphenyl-4-carboxylic acid {2-[(2-dimethylamino-ethyl)-methyl-amino]-benzothiazol-6-yl}-amide (0.48 g, 71%). The material is dissolved in EtOH and treated with 1.0 M HCl in EtOH (0.94 mL). Organic solvent is removed in vacuo, the residue is dissolved in i-PrOH, heptane is added and the resulting precipitate is collected to give 0.43 g (84%) of the hydrochloride salt. LC/MS: Retention time=5.51 min; (m/z): calcd for $C_{27}H_{29}ClN_4O_2S$ (M+H)$^+$: 510.1; found: 510.0.

Example 122

2'-Chloro-4'-isopropoxy-biphenyl-4-carboxylic acid {2-[(2-dimethylamino-ethyl)-methyl-amino]-benzothiazol-6-yl}-amide Hydrochloride Step 1. 2'-Chloro-4'-isopropoxy-biphenyl-4-carboxylic Acid Methyl Ester

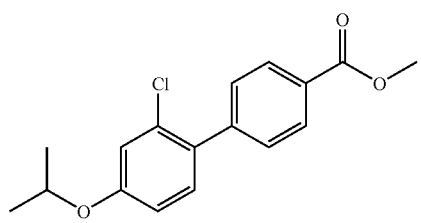

The title compound is prepared by following a procedure analogous to Example 113, Step 1, using 1-bromo-2-chloro-4-isopropoxy-benzene (1.0 g, 4.01 mmol) and 4-boronic acid-benzoic methyl ester (0.79 g, 4.41 mmol) to give 1.0 g (86%).

Step 2. 2'-Chloro-4'-isopropthoxy-biphenyl-4-carboxylic Acid

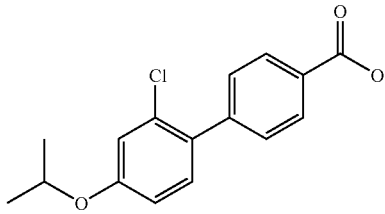

The title compound is prepared by following a procedure analogous to Example 113, Step 1, using 2'-chloro-4'-isopropoxy-biphenyl-4-carboxylic acid methyl ester (1.0 g, 3.44 mmol) to afford 0.90 g (90%). LC/MS (m/z): calcd for $C_{16}H_{15}ClO_3$ (M−H)$^−$: 289.7; found: 289.2.

Step 3. 2'-Chloro-4'-isopropoxy-biphenyl-4-carboxylic acid {2-[(2-dimethylamino-ethyl)-methyl-amino]-benzothiazol-6-yl}-amide Hydrochloride

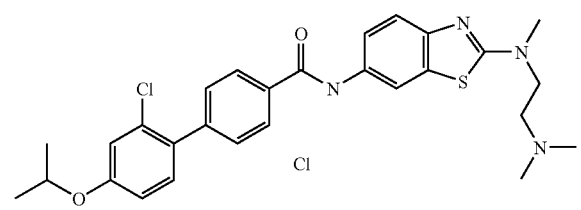

The title compound is prepared by following Method A, using 2'-chloro-4'-isopropoxy-biphenyl-4-carboxylic acid (0.35 g, 1.21 mmol), and N*2*-(2-dimethylamino-ethyl)-N*2*-methyl-benzothiazole-2,6-diamine (0.23 g, 0.93 mmol) to afford 2'-chloro-4'-isopropoxy-biphenyl-4-carboxylic acid {2-[(2-dimethylamino-ethyl)-methyl-amino]-benzothiazol-6-yl}-amide (0.23 g, 48%). The material is dissolved in EtOH and treated with 1.0 M HCl in EtOH (0.44 mL). Organic solvent is removed in vacuo, the residue is dissolved in i-PrOH, heptane is added and the resulting precipitate is collected to give 0.24 g (96%) of the hydrochloride salt. LC/MS, Retention time=5.73 min; (m/z): calcd for $C_{28}H_{31}ClN_4O_2S$: 523.1; found: 523.0.

Example 123

2'-Chloro-4'-cyclopentyloxy-biphenyl-4-carboxylic Acid {2-[(2-dimethylamino-ethyl)-methyl-amino]-benzothiazol-6-yl}-amide Hydrochloride

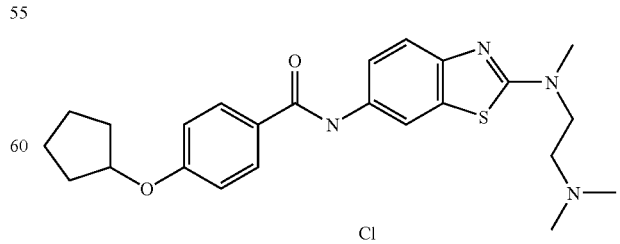

The title compound is prepared by following Method A, using 4-cyclopentyloxy-benzoic acid (Jones, C. D.; Suarez, T. Belg. (1977), BE 847718), (0.20 g, 0.97 mmol), and N*2*-(2-dimethylamino-ethyl)-N*2*-methyl-benzothiazole-2,6-diamine (0.19 g, 0.75 mmol) to give 2'-chloro-4'-cyclopentyloxy-biphenyl-4-carboxylic acid {2-[(2-dimethylamino-ethyl)-methyl-amino]-benzothiazol-6-yl}-amide (0.065 g, 20%). The material is dissolved in EtOH and treated with 1.0 M HCl in EtOH (0.15 mL). Heptane is added and the resulting precipitate is collected to give 0.059 g, (83%) of the hydrochloride salt. LC/MS, Retention time=0.92 min; (m/z): calcd for $C_{24}H_{30}N_4O_2S$: 439.6; found: 439.3.

Example 124

4-Cyclohexylmethoxy-N-{2-[methyl-(1-methyl-pyrrolidin-3-yl)-amino]-benzothiazol-6-yl}-benzamide Hydrochloride Salt

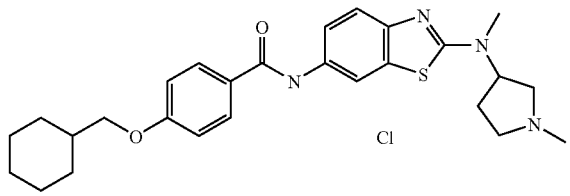

The title compound is prepared by following Method C, using 4-cyclohexylmethoxy-benzoic acid (Crooks, S. L.; Merrill, B. A.; Wightman, P. D. WO 9603983 A1.) (0.46 g, 1.98 mmol), oxalyl chloride (0.66 mL, 7.62 mmol) and isomer-1 of N*2*-methyl-N*2*-(1-methyl-pyrrolidin-3-yl)-benzothiazole-2,6-diamine (0.40 g, 1.51 mmol) to afford 4-cyclohexylmethoxy-N-{2-[methyl-(1-methyl-pyrrolidin-3-yl)-amino]-benzothiazol-6-yl}-benzamide (0.083 11%). The material is dissolved in EtOH and treated with 1.0 M HCl in EtOH (0.17 mL). Heptane is added and the resulting solid is collected to give 0.052 g (59%) of the hydrochloride salt. LC/MS: Retention time=5.38 min; (m/z): calcd for $C_{27}H_{34}N_4O_2S$ (M+H)$^+$: 479.7; found: 479.3.

Example 125

2'-Chloro-4'-trifluoromethoxy-biphenyl-4-carboxylic Acid {2-[(2-dimethylamino-ethyl)-methyl-amino]-benzothiazol-6-yl}-amide Hydrochloride Salt Step 1. 2'-Chloro-4'-trifluoromethoxy-biphenyl-4-carboxylic Acid Methyl Ester

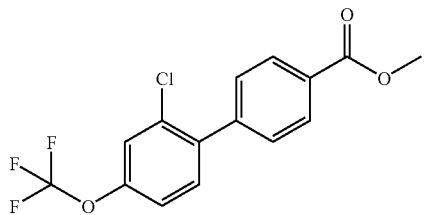

The title compound is prepared by following a procedure analogous to Example 113, Step 1, using 1-bromo-2-chloro-4-trifluoromethoxy-benzene (0.23 g, 0.84 mmol) and 4-boronic acid-benzoic acid methyl ester (0.18 g, 1.00 mmol) to afford 0.13 g (47%).

Step 2. 2'-Chloro-4'-trifluoromethoxy-biphenyl-4-carboxylic Acid

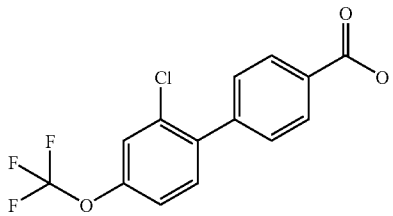

The title compound is prepared by following a procedure analogous to Example 113, Step 2, using 2'-chloro-4'-trifluoromethoxy-biphenyl-4-carboxylic acid methyl ester (0.13 g, 0.39 mmol) to afford 0.057 g (53%).

Step 3. 2'-Chloro-4'-trifluoromethoxy-biphenyl-4-carboxylic acid {2-[(2-dimethylamino-ethyl)-methyl-amino]-benzothiazol-6-yl}-amide Hydrochloride Salt

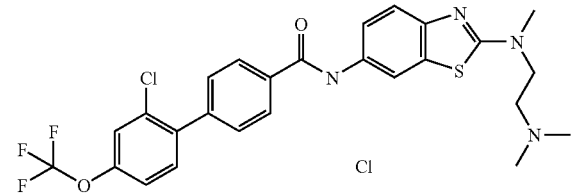

The title compound is prepared by following Method A, using 2'-chloro-4'-trifluoromethoxy-biphenyl-4-carboxylic acid (0.057 g, 0.18 mmol), and N*2*-(2-Dimethylamino-ethyl)-N*2*-methyl-benzothiazole-2,6-diamine (0.38 g, 0.15 mmol) to afford 2'-chloro-4'-trifluoromethoxy-biphenyl-4-carboxylic acid {2-[(2-dimethylamino-ethyl)-methyl-amino]-benzothiazol-6-yl}-amide (0.033 g, 40%). The material is dissolved in EtOH and treated with 1.0 M HCl in EtOH (0.06 mL). Heptane is added and the resulting precipitate is collected to give 0.028 g (78%) of the hydrochloride salt. LC/MS, Retention time=5.38 nm; (m/z): calcd for $C_{26}H_{24}ClF_3N_4O_2S$ (M+H)$^+$: 549.0; found: 549.0.

Example 126

2'-Methyl-biphenyl-4-carboxylic acid {2-[(2-dimethylamino-ethyl)-methyl-amino]-benzothiazol-6-yl}-amide Step 1. N-{2-[(2-Dimethylamino-ethyl)-methyl-amino]-benzothiazol-6-yl}-4-iodo-benzamide

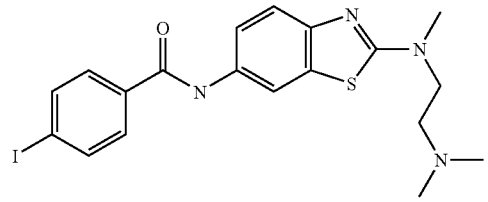

The title compound is prepared by following Method C, using 4-iodo-benzoic acid (4.46 g, 17.97 mmol), oxalyl chloride (5.2 mL, 59.11 mmol) and N*2*-(2-dimethylaminoethyl)-N*2*-methyl-benzothiazole-2,6-diamine (3.0 g, 11.98 mmol) to afford 3.77 g, 66%). LC/MS, Retention time=5.62 min; (m/z): calcd for $C_{19}H_{211}N_4OS$: 480.4; found: 480.7.

Step 2. 2'-Methyl-biphenyl-4-carboxylic acid {2-[(2-dimethylamino-ethyl)-methyl-amino]-benzothiazol-6-yl}-amide

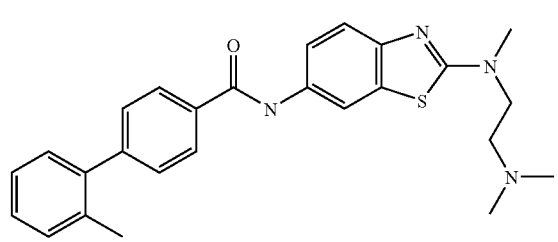

The title compound is prepared by following a procedure analogous to Example 113, Step 1, using N-{2-[(2-dimethylamino-ethyl)-methyl-amino]-benzothiazol-6-yl}-4-iodobenzamide (0.15 g, 0.31 mmol) and 2-methylphenylboronic acid (0.051 g, 0.38 mmol) to afford 0.098 g (71%). LC/MS, Retention time=4.75 min; (m/z): calcd for $C_{26}H_{28}N_4OS$ $(M+H)^+$: 445.6; found: 445.0.

Example 127

4'-Methoxy-biphenyl-4-carboxylic Acid {2-[(2-dimethylamino-ethyl)-methyl-amino]-benzothiazol-6-yl}-amide

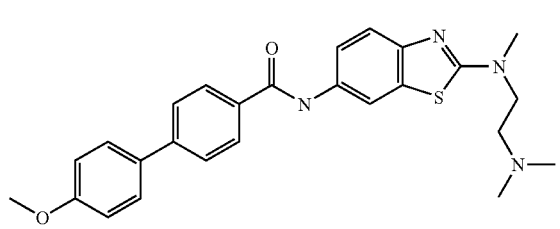

The title compound is prepared by following a procedure analogous to Example 113, Step 1, using N-{2-[(2-dimethylamino-ethyl)-methyl-amino]-benzothiazol-6-yl}-4-iodobenzamide (0.15 g, 0.31 mmol) and 4-methoxyphenyl boronic acid (0.057 g, 0.38 mmol) to give 0.025 g (16%). LC/MS, Retention time=4.45 min; (m/z): calcd for $C_{26}H_{28}N_4O_2S$ $(M+H)^+$: 461.6; found: 461.0.

Example 128

2'-Chloro-biphenyl-4-carboxylic acid {2-[(2-dimethylamino-ethyl)-methyl-amino]-benzothiazol-6-yl}-amide

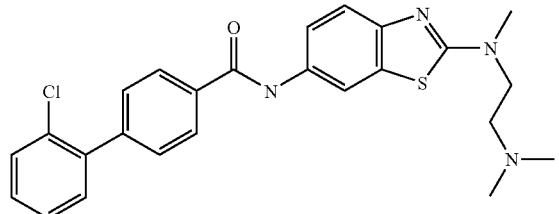

The title compound is prepared by following a procedure analogous to Example 113, Step 1, using N-{2-[(2-dimethylamino-ethyl)-methyl-amino]-benzothiazol-6-yl}-4-iodobenzamide (0.15 g, 0.31 mmol) and 2-chlorophenyl boronic acid (0.059 g, 0.38 mmol) to afford 0.074 g (51%). MS (m/z): calcd for $C_2H_{25}ClN_4OS$ $(M+H)^+$: 466.0; found: 466.2.

Example 129

2'-Methoxy-biphenyl-4-carboxylic Acid {2-[(2-dimethylamino-ethyl)-methyl-amino]-benzothiazol-6-yl}-amide

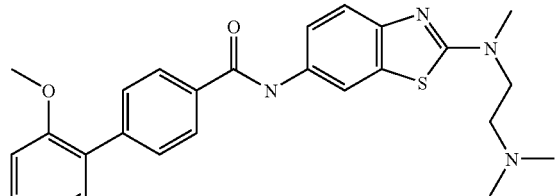

The title compound is prepared by following a procedure analogous to Example 113, Step 1, using N-{2-[(2-dimethylamino-ethyl)-methyl-amino]-benzothiazol-6-yl}-4-iodobenzamide (0.15 g, 0.31 mmol) and 2-methoxyphenyl boronic acid (0.060 g, 0.38 mmol) to afford 0.050 g (35%). LC/MS, Retention time=4.49 min; (m/z): calcd for $C_{26}H_{28}N_4O_2S$ $(M+H)^+$: 461.6; found: 461.0.

Example 130

2'-Cyano-biphenyl-4-carboxylic acid {2-[(2-dimethylamino-ethyl)-methyl-amino]-benzothiazol-6-yl}-amide

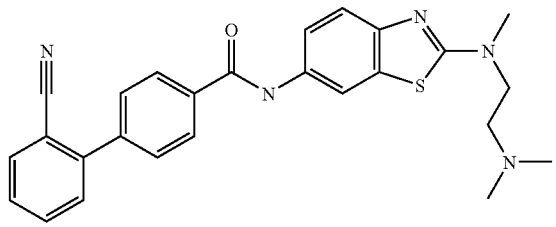

The title compound is prepared by following a procedure analogous to Example 113, Step 1, using N-{2-[(2-dimethylamino-ethyl)-methyl-amino]-benzothiazol-6-yl)}-4-iodobenzamide (0.15 g, 0.31 mmol) and 2-cyanophenyl boronic acid (0.055 g, 0.38 mmol) to afford 0.012 g (8%). LC/MS, Retention time=4.16 min; (m/z): calcd for $C_{26}H_{25}N_5O_2S$ (M+H)$^+$: 456.6; found: 456.0.

Example 131

2',4'-Dichloro-biphenyl-4-carboxylic acid {2-[(2-dimethylamino-ethyl)-methyl-amino]-benzothiazol-6-yl}-amide

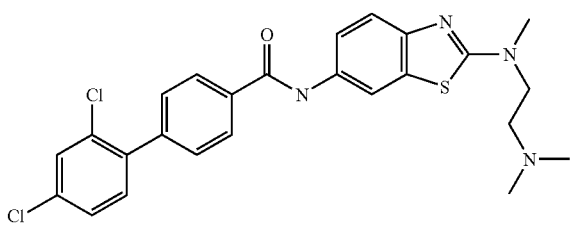

The title compound is prepared by following a procedure analogous to Example 113, Step 1, using N-{2-[(2-dimethylamino-ethyl)-methyl-amino]-benzothiazol-6-yl}-4-iodobenzamide (0.15 g, 0.31 mmol) and 2,4-dichloro-phenyl boronic acid (0.072 g, 0.38 mmol) to give the title compound (0.067 g, 0.13 mmol, 43%). LC/MS, Retention time=5.15 min; (m/z): calcd for $C_{25}H_{24}Cl_2N_4OS$: 499.5; found: 499.0.

Example 132

4'-Fluoro-2'-methyl-biphenyl-4-carboxylic acid {2-[(2-dimethylamino-ethyl)-methyl-amino]-benzothiazol-6-yl}-amide

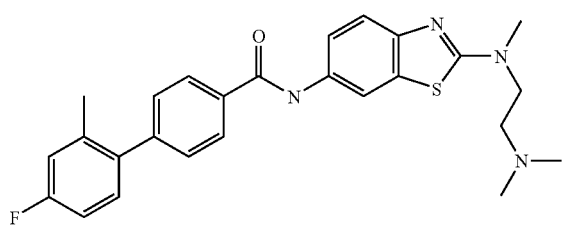

The title compound is prepared by following a procedure analogous to Example 113, Step 1, using N-{2-[(2-dimethylamino-ethyl)-methyl-amino]-benzothiazol-6-yl}-4-iodobenzamide (0.15 g, 0.31 mmol) and 4-fluoro-2-methyl-phenyl boronic acid (0.071 g, 0.38 mmol) to afford 0.084 g (59%). LC/MS, Retention time=4.79 min; (m/z): calcd for $C_{26}H_{27}FN_4OS$ (M+H)$^+$: 463.6; found: 463.0.

Example 133

2',3'-Dichloro-biphenyl-4-carboxylic acid {2-[(2-dimethylamino-ethyl)-methyl-amino]-benzothiazol-6-yl}-amide

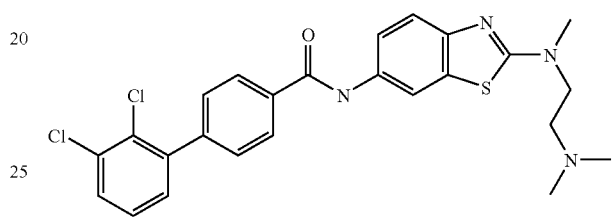

The title compound is prepared by following a procedure analogous to Example 113, Step 1, using N-{2-[(2-dimethylamino-ethyl)-methyl-amino]-benzothiazol-yl}-4-iodo-benzamide (0.15 g, 0.31 mmol) and 2,3-dichloro-phenyl boronic acid (0.072 g, 0.38 mmol) to afford 0.13 g (83%). LC/MS, Retention time=5.08 min; (m/z): calcd for $C_{25}H_{24}Cl_2N_4OS$: 499.5; found: 499.0.

Example 135

2'-Chloro-4'-trifluoromethyl-biphenyl-4-carboxylic acid {2-[(2-dimethylamino-ethyl)-methyl-amino]-benzothiazol-6-yl}-amide

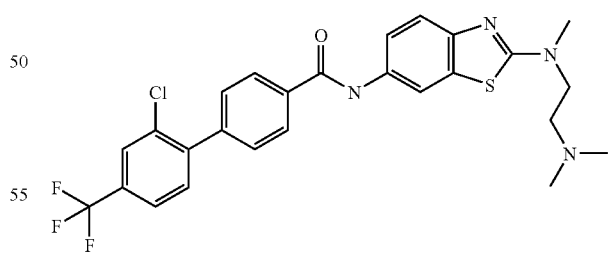

The title compound is prepared by following a procedure analogous to Example 113, Step 1, using N-{2-[(2-dimethylamino-ethyl)-methyl-amino]-benzothiazol-6-yl}-4-iodobenzamide (0.10 g, 0.21 mmol) and 2-chloro-4-trifluoromethyl-phenyl boronic acid (0.056 g, 0.25 mmol) to afford 0.045 g (40%). LC/MS, Retention time=5.34 min; (m/z): calcd for $C_{26}H_{24}ClF_3N_4OS$: 533.0; found: 533.0.

Example 136

2'-Chloro-4'-fluoro-biphenyl-carboxylic Acid {2-[(2-dimethylamino-ethyl)-methyl-amino]-benzothiazol-6-yl}-amide

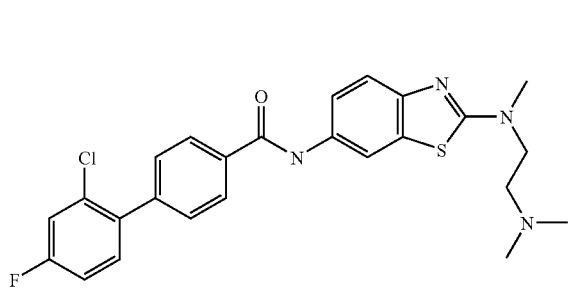

The title compound is prepared by following a procedure analogous to Example 113, Step 1, using N-{2-[(2-dimethylamino-ethyl)-methyl-amino]-benzothiazol-6-yl}-4-iodo-benzamide (0.20 g, 0.42 mmol) and 2-(2-chloro-4-fluoro-phenyl)-4,4,5,5-tetramethyl-[1,3,2]dioxaborolane (0.18 g, 0.71 mmol) to afford 0.072 g (35%). LC/MS, Retention time 4.98 min; (m/z): calcd for $C_{25}H_{24}ClFN_4OS$: 483.0; found: 483.0.

Example 137

3'-Methyl-biphenyl-4-carboxylic acid {2-[(2-dimethylamino-ethyl)-methyl-amino]-benzothiazol-6-yl}-amide

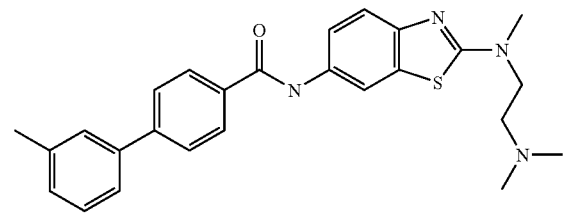

The title compound is prepared by following a procedure analogous to Example 113, Step 1, using N-{2-[(2-dimethylamino-ethyl)-methyl-amino]-benzothiazol-6-yl}-4-iodo-benzamide (0.10 g, 0.21 mmol) and 3-methyl-phenyl boronic acid (0.037 g, 0.27 mmol) to afford 0.048 g (51%). LC/MS, Retention time=4.96 min; (m/z): calcd for $C_2H_{26}N_4OS$ (M+H)$^+$: 445.6; found: 445.0.

Example 138

2'-Chloro-4'-methoxy-biphenyl-4-carboxylic Acid {2-[(2-dimethylamino-ethyl)-methyl-amino]-benzothiazol-6-yl}-amide

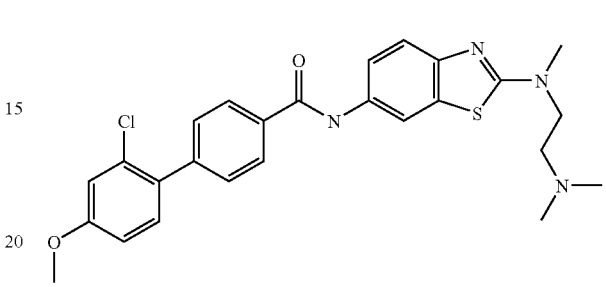

The title compound is prepared by following a procedure analogous to Example 113, Step 1, using N-{2-[(2-dimethylamino-ethyl)-methyl-amino]-benzothiazol-6-yl}-4-iodo-benzamide (0.05 g, 0.12 mmol) and 2-chloro-4-methoxy-phenyl boronic acid (0.026 g, 0.14 mmol) to afford 0.036 g (60%). LC/MS, Retention time=4.53 min; (m/z): calcd for $C_{26}H_{27}ClN_4O_2S$ (M+H)$^+$: 496.1; found: 496.0.

Example 139

2',5'-Dichloro-biphenyl-4-carboxylic Acid {2-[(2-dimethylamino-ethyl)-methyl-amino]-benzothiazol-6-yl}-amide

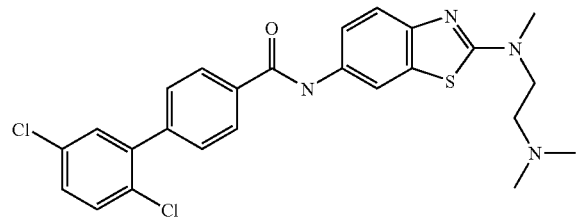

The title compound is prepared by following a procedure analogous to Example 113, Step 1, using N-{2-[(2-dimethylamino-ethyl)-methyl-amino]-benzothiazol-6-yl}-4-iodo-benzamide (0.12 g, 0.25 mmol) and 2,5-dichloro-phenyl boronic acid (0.057 g, 0.30 mmol) to afford 0.098 g, (79%). LC/MS, Retention time=5.29 min; (m/z): calcd for $C_{25}H_{24}Cl_2N_4OS$: 499.5; found: 499.0.

Example 140

5-(2-Chloro-4-methoxy-phenyl)-pyrazine-2-carboxylic acid {2-[(2-dimethylamino-ethyl)-methyl-amino]-benzothiazol-6-yl}-amide Step 1. 5-Chloro-pyrazine-2-carboxylic acid {2-[(2-dimethylamino-ethyl)-methyl-amino]-benzothiazol-6-yl}-amide

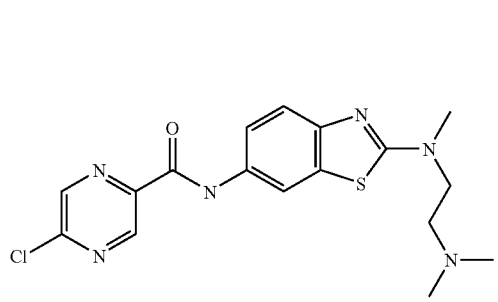

The title compound is prepared by essentially following the procedure of Method C, using 5-chloro-pyrazine-2-carboxylic acid (Kiener, A.; Roduit, J.-P.; Tschech, A.; Tinschert, A.; Heinzmann, K. Synlett 1994, 814-16), (0.096 g, 1.20 mmol), oxalyl chloride (0.35 mL, 3.99 mmol) and N*2*-(2-dimethylamino-ethyl)-N*2*-methyl-benzothiazole-2,6-diamine (0.20 g, 0.80 mmol) to afford 0.21 g, (67%). MS (m/z): calcd for $C_{17}H_{19}ClN_6OS$ (M+H)$^+$: 391.9; found: 391.2.

Step 2. 5-(2-Chloro-4-methoxy-phenyl)-pyrazine-2-carboxylic acid {2-[(2-dimethylamino-ethyl)-methyl-amino]-benzothiazol-6-yl}-amide

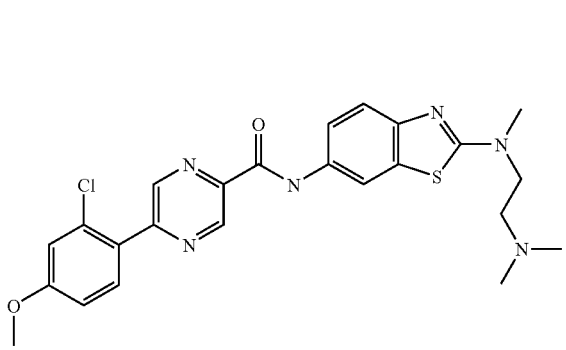

The title compound is prepared by following a procedure analogous to Example 113, Step 1, using 5-chloro-pyrazine-2-carboxylic acid {2-[(2-dimethylamino-ethyl)-methyl-amino]-benzothiazol-6-yl}-amide (0.10 g, 0.26 mmol) and 2-chloro-4-methoxy-phenyl boronic acid (0.057 g, 0.31 mmol) to afford 0.062 g (48%). LC/MS, Retention time=4.89 nm in; (m/z): calcd for $C_{24}H_{25}ClN_6O_2S$: 497.0; found: 499.0.

Example 141

5-(2,4-Dichloro-phenyl)-pyrazine-2-carboxylic acid {2-[(2-dimethylamino-ethyl)-methyl-amino]-benzothiazol-6-yl}-amide

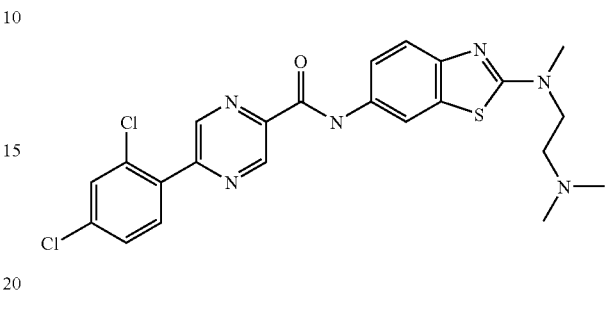

The title compound is prepared by following a procedure analogous to Example 113, Step 1, using 5-chloro-pyrazine-2-carboxylic acid {2-[(2-dimethylamino-ethyl)-methyl-amino]-benzothiazol-6-yl}-amide (0.077 g, 0.20 mmol) and 2,4-dichloro-phenyl boronic acid. (0.045 g, 0.24 mmol) to afford the product. LC/MS, Retention time=5.12 min; (m/z): calcd for $C_{23}H_{22}Cl_2N_6O_2S$: 501.4; found: 501.0.

Example 142

2'-methyl-4'-ethoxy-biphenyl-4-carboxylic acid {2-[(2-dimethylamino-ethyl)-methyl-amino]-benzothiazol-6-yl}-amide Hydrochloride Salt

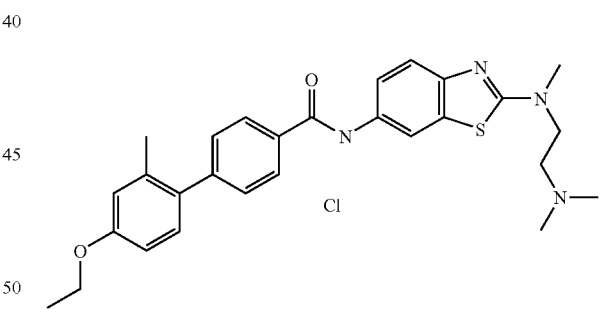

The title compound is prepared by following a procedure analogous to Example 113, Step 1, using N-{2-[(2-dimethylamino-ethyl)-methyl-amino]-benzothiazol-6-yl}iodo-benzamide (0.40 g, 0.83 mmol) and 2-methyl-4-ethoxyl-phenyl boronic acid (0.18 g, 0.10 mmol) to afford 2'-chloro-4'-ethoxy-biphenyl-4-carboxylic acid {2-[(2-dimethylamino-ethyl)-methyl-amino]-benzothiazol-6-yl}-amide (0.32 g, 76%). The material is dissolved in EtOH, treated with 1.0 m HCl in EtOH (0.65 mL), concentrated and recrystallized from i-PrOH/Heptane to give 0.30 g (92%) as the hydrochloride salt. LC/MS, Retention time=5.40 min; (m/z): calcd for $C_{28}H_{32}N_4O_2S$ (M+H)$^+$: 499.7; found: 489.0.

Example 143

4'-Chloro-2'-methyl-biphenyl-4-carboxylic Acid {2-[(2-dimethylamino-ethyl)-methyl-amino]-benzothiazol-6-yl}-amide Hydrochloide Salt

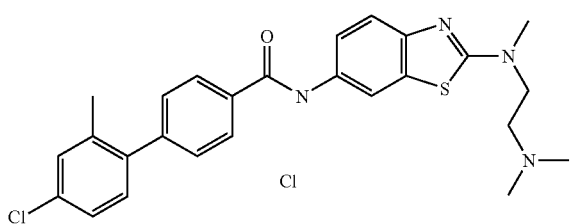

The title compound is prepared by following a procedure analogous to Example 113, Step 1, using N-{2-[(2-dimethylamino-ethyl)-methyl-amino]-benzothiazol-6-yl}-4-iodo-benzamide (0.40 g, 0.83 mmol) and 2-methyl-4-ethoxyl-phenyl boronic acid (0.17 g, 0.10 mmol) to give 4'-chloro-2'-methyl-biphenyl-4-carboxylic acid {2-[(2-dimethylamino-ethyl)-methyl-amino]-benzothiazol-6-yl}-amide (0.13 g, 0.27 mmol, 33%). The material is dissolved in EtOH, treated with 1.0 M HCl in EtOH (0.65 mL), concentrated and recrystallized from EtOH/Heptane to give 0.13 g (93%) as the hydrochloride salt. LC/MS, Retention time=5.08 min; (m/z): calcd for $C_{26}H_{27}ClN_4OS$ (M+H)$^+$: 479.4; found: 479.0.

Example 144

2'-Chloro-4'-methyl-biphenyl-4-carboxylic acid {2-[(2-dimethylamino-ethyl)-methyl-amino]-benzothiazol-6-yl}-amide Hydrochloride Salt

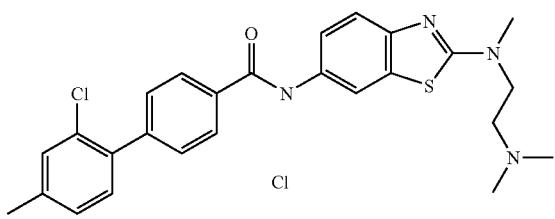

The title compound is prepared by following a procedure analogous to Example 113, Step 1, using N-{2-[(2-dimethylamino-ethyl)-methyl-amino]-benzothiazol-6-yl}-4-iodo-benzamide (0.40 g, 0.83 mmol) and 2-chloro-4-methyl-phenyl boronic acid (0.17 g, 0.10 mmol) to afford 2'-chloro-4'-methyl-biphenyl-4-carboxylic acid {2-[(2-dimethylamino-ethyl)-methyl-amino]-benzothiazol-6-yl}-amide (0.21 g, 0.44 mmol, 53%). The material is dissolved in EtOH, treated with 1.0 M HCl in EtOH (0.44 mL), concentrated and recrystallized from EtOH/Heptane to give 0.20 g (88%) as the hydrochloride salt. LC/MS, Retention time=5.04 min; (m/z): calcd for $C_{26}H_{27}ClN_4OS$ (M+H)$^+$: 479.4; found: 479.0.

Example 145

Preparation 2',4'-Dimethyl-biphenyl-4-carboxylic Acid {2-[(2-dimethylamino-ethyl)-methyl-amino]-benzothiazol-6-yl}-amide Hydrochloride

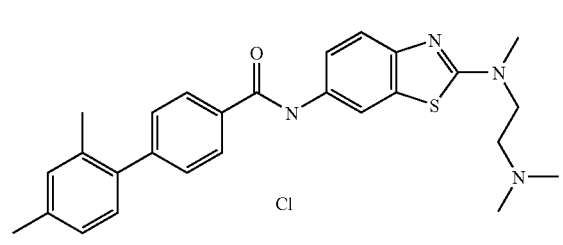

The title compound is prepared by following a procedure analogous to Example 113, Step 1, using N-{2-[(2-dimethylamino-ethyl)-methyl-amino]-benzothiazol-6-yl}-4-iodo-benzamide (0.40 g, 0.83 mmol) and 2,4-dimethyl-phenyl boronic acid (0.25 g, 1.67 mmol) to afford 2',4'-dimethyl-biphenyl-4-carboxylic acid {2-[(2-dimethylamino-ethyl)-methyl-amino]-benzothiazol-6-yl}-amide (0.25 g, 66%). The material is dissolved in EtOH, treated with 1.0 m HCl in EtOH (0.55 mL), concentrated and recrystallized from EtOH/Heptane to give the hydrochloride salt. LC/MS, Retention time=5.03 min; (m/z): calcd for $C_{27}H_{30}N_4OS$ (M+H)$^+$: 459.4; found: 459.2.

Example 146

2',4'-Dichloro-biphenyl-4-carboxylic acid {2-[(2-dimethylamino-ethyl)-methyl-amino]-benzooxazol-5-yl}-amide Hydrochloride Salt

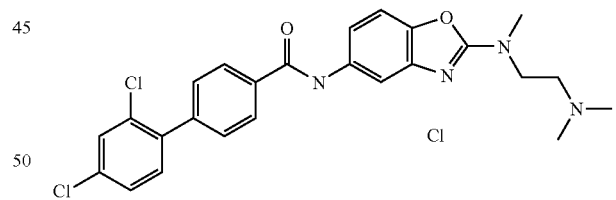

The title compound is prepared by following a procedure analogous to Example 113, Step 1, using N*2*-(2-dimethylamino-ethyl)-N*2*-methyl-benzooxazole-2,5-diamine (0.40 g, 1.71 mmol), and 2',4'-dichloro-biphenyl-4-carboxylic acid (0.59 g, 2.22 mmol) to afford 2',4'-dichloro-biphenyl-4-carboxylic acid {2-[(2-dimethylamino-ethyl)-methyl-amino]-benzooxazol-5-yl}-amide (0.64 g, 77%). The prepared material (0.23 g, 0.473 mmol) is dissolved in EtOH and treated with 1.0 M HCl in EtOH (0.45 mL). The reaction is refluxed and the hydrochloride salt is isolated by centrifuge after precipitation with heptane as a white solid (0.18 g, 0.347 mmol, 73%). LC/MS (m/z): calcd for $C_{25}H_{24}Cl_2N_4O_2 \cdot HCl$ (M+H)$^+$: 483.4; found: 483.3.

Example 147

4-Cyclohexylmethoxy-N-{2-[(2-dimethylamino-ethyl)-methyl-amino]-benzooxazol-5-yl}-benzamide Hydrochloride Salt

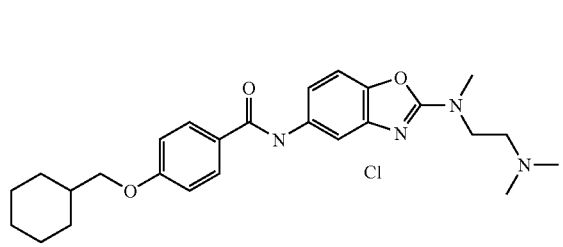

The title compound is prepared by following a procedure analogous to Example 113, Step 1, using N*2*-(2-dimethylamino-ethyl)-N*2*-methyl-benzooxazole-2,5-diamine (0.12 g, 0.525 mmol), 4-cyclohexylmethoxy-benzoic acid (0.16 g, 0.683 mmol) to give 4-cyclohexylmethoxy-N-{2-[(2-dimethylamino-ethyl)-methyl-amino]-benzooxazol-5-yl}-benzamide (0.18 g, 76%). The material is dissolved in EtOH and treated with 1.0 M HCl in EtOH (0.40 mL) to give the hydrochloride salt (0.11 g, 43%). LC/MS (m/z): calcd for $C_{26}H_{34}N_4O_3HCl$ (M+H)$^+$: 451.4; found: 451.2.

The following compounds, Example 148 to 159, are prepared according to the procedure outlined in General Method B utilizing appropriate amine and corresponding acid components.

Example 148

2',4'-Dichloro-biphenyl-4-carboxylic acid {2-[(2-dimethylamino-ethyl)-methyl-amino]-benzooxazol-5-yl}-amide Hydrochloride

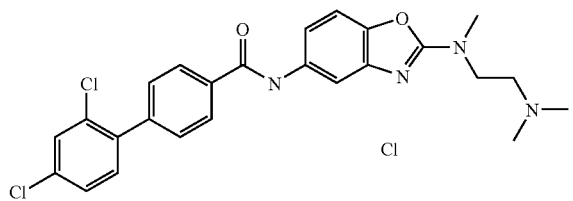

LC/MS: RT (5.08 min); (m/z): calcd for $C_{25}H_{24}Cl_2N_4O_2$ (M+H)$^+$: 483.4; found: 483.3.

Example 149

4-Cyclohexylmethoxy-N-{2-[(2-dimethylamino-ethyl)-methyl-amino]-benzooxazol-5-yl}-benzamide Hydrochloride

LC/MS: RT 4.99 min); (m/z): calcd for $C_{26}H_{34}N_4O_3$ (M+H)$^+$: 451.6; found: 451.2.

Example 150

2'-Chloro-4'-methyl-biphenyl-4-carboxylic Acid {2-[(2-dimethylamino-ethyl)-methyl-amino]-benzooxazol-5-yl}-amide Hydrochloride

LC/MS: RT 4.76 min); (m/z): calcd for $C_{26}H_{27}ClN_4O_2$ (M+H)$^+$: 462.9; found: 463.0.

Example 151

2'-Chloro-4'-fluoro-biphenyl-4-carboxylic acid {2-[(2-dimethylamino-ethyl)-methyl-amino]-benzooxazol-5-yl}-amide Hydrochloride

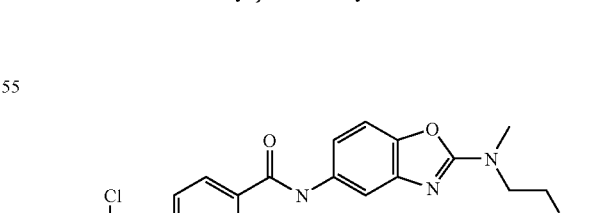

LC/MS: RT 4.55 min); (m/z): calcd for $C_{25}H_{24}ClFN_4O_2$ (M+H)$^+$: 466.9; found: 467.0.

Example 152

4'-Fluoro-biphenyl-4-carboxylic acid {2-[methyl-(2-morpholin-4-yl-ethyl)-amino]-benzooxazol-5-yl}-amide Hydrochloride

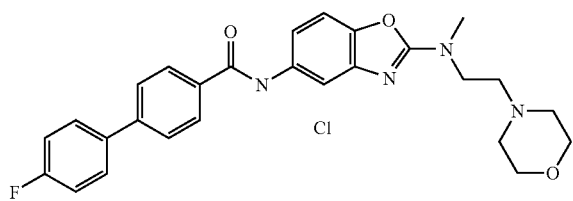

LC/MS: RT 4.41 min); (m/z): calcd for C27H27FN4O3 (M+H)+: 475.5; found: 475.0.

Example 153

4'-Chloro-2'-methyl-biphenyl-4-carboxylic acid {2-[(2-dimethylamino-ethyl)-methyl-amino]-benzooxazol-5-yl}-amide Hydrochloride

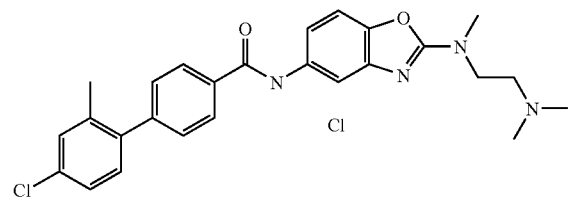

LC/MS: RT 4.88 min); (m/z): calcd for C26H27ClN4O2 (M+H)+: 463.9; found: 463.0.

Example 154

2-(2,4-Dichloro-phenoxy)-N-{2-[(2-dimethylamino-ethyl)-methyl-amino]-benzooxazol-5-yl}-acetamide Hydrochloride

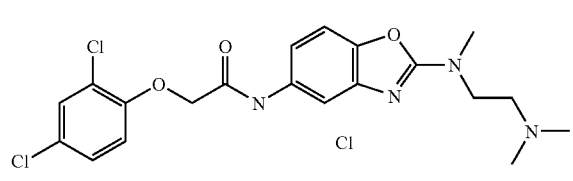

LC/MS: RT 4.18 min); (m/z): calcd for C20H22Cl2N4O3 (M+H)+: 437.3; found: 437.0.

Example 155

4'-Fluoro-biphenyl-4-carboxylic acid {2-[methyl-((R)-4-methyl-morpholin-2-ylmethyl)-amino]-benzooxazol-5-yl}-amide Hydrochloride

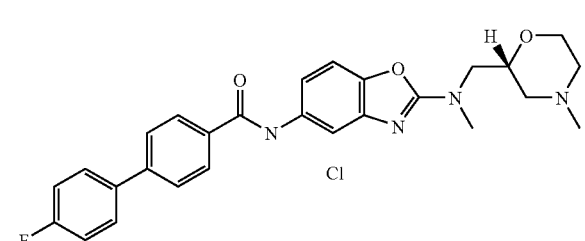

LC/MS: RT 4.41 min); (m/z): calcd for C27H27FN4O3 (M+H)+: 475.5; found: 475.0.

Example 156

2'-Chloro-4'-methyl-biphenyl-4-carboxylic acid {2-[methyl-(1-methyl-piperidin-4-yl)-amino]-benzooxazol-5-yl}-amide Hydrochloride

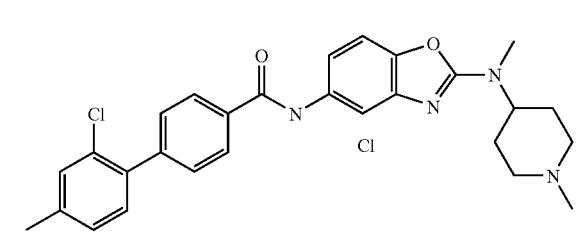

LC/MS: RT 4.89 min); (m/z): calcd for C28H29ClN4O2 (M+H)+: 489.0; found: 489.0.

Example 157

2'-Chloro-4'-fluoro-biphenyl-4-carboxylic acid {2-[methyl-(1-methyl-piperidin yl)-amino]-benzooxazol-5-yl}-amide Hydrochloride

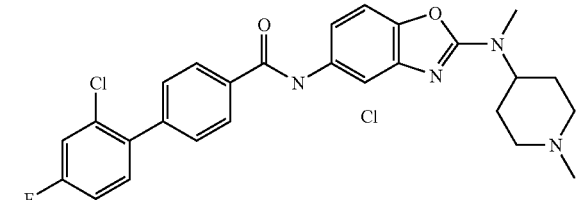

LC/MS: RT 4.81 min); (m/z): calcd for C27H26ClFN4O2 (M+H)+: 492.9; found: 493.0.

Example 158

2',4'-Dichloro-biphenyl-4-carboxylic Acid {2-[methyl-(1-methyl-piperidin-4-yl)-amino]-benzooxazol-5-yl}-amide Hydrochloride

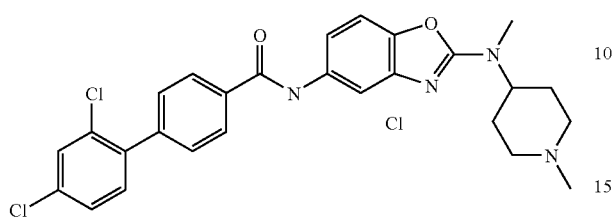

LC/MS: RT 4.91 min); (m/z): calcd for C27H26Cl2N4O2 (M+H)+: 509.4; found: 509.0.

Example 159

4'-Chloro-2'-methyl-biphenyl-4-carboxylic acid {2-[methyl-(1-methyl-piperidin-4-yl)-amino]-benzooxazol-5-yl}-amide Hydrochloride

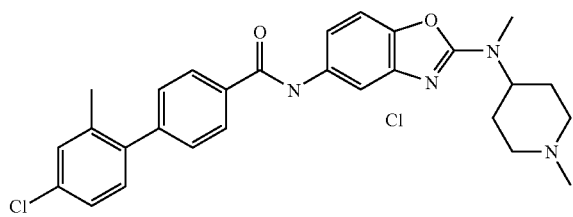

LC/MS: RT 4.98 min); (m/z): calcd for C28H29ClN4O2 (M+H)+: 489.0; found: 489.0.

Example 160

2-Phenyl-oxazole-5-carboxylic acid {2-[methyl-(1-methyl-piperidin-4-yl)-amino]-benzooxazol-5-yl}-amide; Hydrochloride

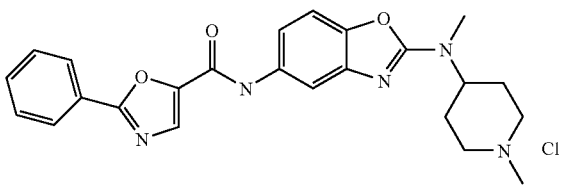

Combine 2-phenyl-oxazole-5-carboxylic acid (34 mg, 0.18 mmol), TBTU (58 mg, 0.18 mmol), and $N^2$-Methyl-$N^2$-(1-methyl-piperidin-4-yl)-benzooxazole-2,5-diamine (40 mg, 0.15 mmol) in acetonitrile (3.0 mL) and shake at 60° C. in a sealed tube overnight. Cool the reaction to room temperature and add water (1.0 mL) a put the mixture on an SCX cartridge (previously conditioned with MeOH). Wash with acetone (3×3.0 mL) non basic impurities and then with MeOH (3×3.0 mL). Eluting with a 2N solution of NH3 in MeOH (4.0 mL) and concentrate to afford the title compound (65 mg, 100%). LC/MS, RT=4.79 min., mass spectrum (m/z) calcd found (M+H)+: 432.2. The material is dissolved in MeOH and treated with 2M HCl in ether (2.0 mL). Organic solvent is removed in vacuo and the resulting precipitate is collected to give 70 mg (100%) of the hydrochloride salt.

The following compounds have been prepared according to the procedure described in Example 160.

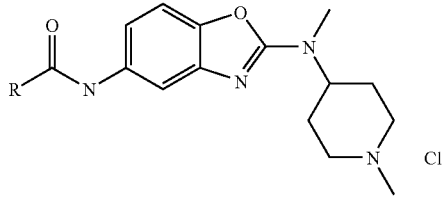

| Ex. | R | Name | Found for (M + H)+ | RT, min. |
|---|---|---|---|---|
| 161 | ![R group phenyl-methyl-thiazole] | 4-Methyl-2-phenyl-thiazole-5-carboxylic acid {2-[methyl-(1-methyl-piperidin-4-yl)-amino]-benzooxazol-5-yl}-amide | 462.2 | 4.91 |
| 162 | ![R group chlorophenyl-methyl-thiazole] | 2-(4-Chloro-phenyl)-4-methyl-thiazole-5-carboxylic acid {2-[methyl-(1-methyl-piperidin-4-yl)-amino]-benzooxazol-5-yl}-amide | 496.2 | 5.45 |

| Ex. | R | Name | Found for (M + H)+ | RT, min. |
|---|---|---|---|---|
| 163 | 3-phenylisoxazol-5-yl | 3-Phenyl-isoxazole-5-carboxylic acid {2-[methyl-(1-methyl-piperidin-4-yl)-amino]-benzooxazol-5-yl}-amide | 432.2 | 4.71 |
| 164 | 5-phenylisoxazol-3-yl | 5-Phenyl-isoxazole-3-carboxylic acid {2-[methyl-(1-methyl-piperidin-4-yl)-amino]-benzooxazol-5-yl}-amide | 432.2 | 4.88 |
| 165 | 5-phenylthiophen-2-yl | 5-Phenyl-thiophene-2-carboxylic acid {2-[methyl-(1-methyl-piperidin-4-yl)-amino]-benzooxazol-5-yl}-amide | 447.2 | 5.19 |

Example 166

5-Phenyl-[1,3,4]oxadiazole-2-carboxylic acid {2-[methyl-(1-methyl-piperidin-4-yl)-amino]-benzooxazol-5-yl}-amide; Hydrochloride

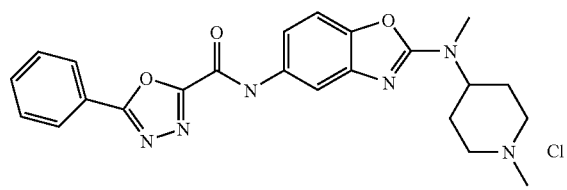

Add drowise 2N AlMe₃ in hexanes (0.3 mL, 0.6 mmol) to a solution of N²-Methyl-N²-(1-methyl-piperidin-4-yl)-benzooxazole-2,5-diamine (46 mg, 0.176 mmol) in CH₂Cl₂ (5.0 mL) and stir at room temperature for 15 min. Then, add dropwise a solution of 5-Phenyl-[1,3,4]oxadiazole-2-carboxylic acid methyl ester (37 mg, 0.181 mmol) in CH₂Cl₂ (2.5 mL). Stir the reaction to room temperature overnight. Add dropwise a 9:1 mixture of CH₂Cl₂-MeOH (5.0 mL) and then a solution of 0.5N HCl (2.0 mL). The mixture is purified using an a SCX cartridge (previously conditioned with MeoH). Wash with acetone (3×3.0 mL) non basic impurities and then with MeOH (3×3.0 mL). Eluting with a 2N solution of NH₃ in MeOH (4.0 mL) and concentrate to afford the title compound (56 mg, 74%). LC/MS, RT=4.33 min., mass spectrum (m/z) found (M+H)⁺: 433.2. The material is dissolved in MeOH and treated with 2M HCl in ether (2.0 mL). Organic solvent is removed in vacuo and the resulting precipitate is collected to give 67 mg (100%) of the hydrochloride salt.

The following compounds have been prepared according to the procedure described in Example 166.

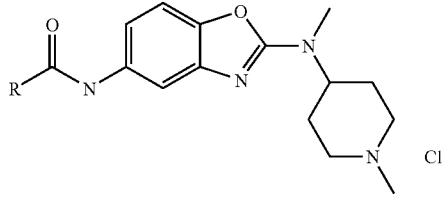

| Ex. | R | Name | Found for (M + H)⁺ | RT, min. |
|---|---|---|---|---|
| 167 | Cl-phenyl-oxadiazolyl | 5-(4-Chloro-phenyl)-[1,3,4]oxadiazole-2-carboxylic acid {2-[methyl-(1-methyl-piperidin-4-yl)-amino]-benzooxazol-5-yl}-amide | 467.2 | 4.87 |
| 168 | phenyl-methyl-oxazolyl | 5-Methyl-4-phenyl-oxazole-2-carboxylic acid {2-[methyl-(1-methyl-piperidin-4-yl)-amino]-benzooxazol-5-yl}-amide | 446.2 | 4.95 |
| 169 | phenyl-oxazolyl | 5-Phenyl-oxazole-2-carboxylic acid {2-[methyl-(1-methyl-piperidin-4-yl)-amino]-benzooxazol-5-yl}-amide | 432.2 | 4.67 |

Example 170

5-(4-Fluorophenyl)-thiophene-2-carboxylic Acid {2-[methyl-(1-methyl-piperidin-4yl)-amino]-benzooxazol-5-yl}-amide, Hydrochloride

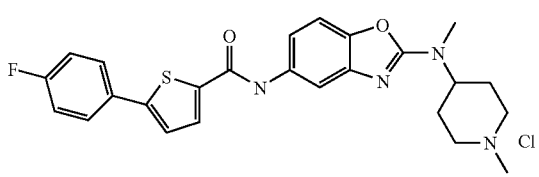

Add 4-fluorophenyl boronic acid (25 mg, 0.18 mmol), 5-bromothio-phene-2-carboxylic acid {2-[methyl-(1-methyl-piperidin-4-yl)-amino]-benzooxazol-5-yl}-amide (67 mg, 0.15 mmol, prepared according to the procedure described in Example 160) and Pd(PPh₃)₄ (40 mg, 0.036 mmol) in a 2:1 mixture of DME:EtOH (2.0 mL) a 2N solution of sodium carbonate (0.15 mL). Degass with nitrogen and heating in a sealed tube at 90° C. overnight. Cool the mixture and filter through Celite. Concentrate and purify in a SCX cartridge as in method X. The compound is purified by HPLC to give 54 mg (77%). LC/MS, RT=5.31 min., mass spectrum (m/z) found (M+H)⁺: 465.2. The material is dissolved in MeOH and treated with 2M HCl in ether (2.0 mL). Organic solvent is removed in vacuo and the resulting precipitate is collected to give 60 mg (100%) of the hydrochloride salt.

The following compounds have been prepared according to the procedure described in Example 170 with the corresponding boronic acid.

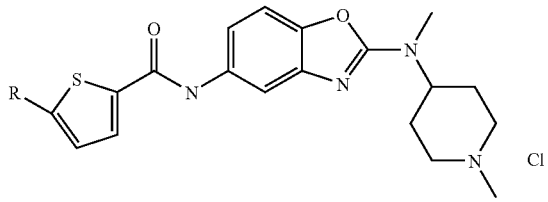

| Ex. | R | Name | Found for (M + H)+ | RT, min. |
|---|---|---|---|---|
| 171 | 4-Cl-phenyl | 5-(4-Chloro-phenyl)-thiophene-2-carboxylic acid {2-[methyl-(1-methyl-piperidin-4-yl)-amino]-benzooxazol-5-yl}-amide | 481.2 | 5.63 |
| 172 | 4-MeO-phenyl | 5-(4-Methoxy-phenyl)-thiophene-2-carboxylic acid {2-[methyl-(1-methyl-piperidin-4-yl)-amino]-benzooxazol-5-yl}-amide | 477.2 | 5.04 |
| 173 | pyridin-4-yl | 5-Pyridin-4-yl-thiophene-2-carboxylic acid {2-[methyl-(1-methyl-piperidin-4-yl)-amino]-benzooxazol-5-yl}-amide | 448.2 | 3.02 |
| 174 | pyridin-3-yl | 5-Pyridin-3-yl-thiophene-2-carboxylic acid {2-[methyl-(1-methyl-piperidin-4-yl)-amino]-benzooxazol-5-yl}-amide | 448.2 | 3.53 |
| 175 | 3,4-difluoro-phenyl | 5-(3,4-Difluoro-phenyl)-thiophene-2-carboxylic acid {2-[methyl-(1-methyl-piperidin-4-yl)-amino]-benzooxazol-5-yl}-amide | 483.2 | 5.37 |
| 176 | 2,4-difluoro-phenyl | 5-(2,4-Difluoro-phenyl)-thiophene-2-carboxylic acid {2-[methyl-(1-methyl-piperidin-4-yl)-amino]-benzooxazol-5-yl}-amide | 483.2 | 5.32 |
| 177 | thiophen-2-yl | [2,2']Bithiophenyl-5-carboxylic acid {2-[methyl-(1-methyl-piperidin-4-yl)-amino]-benzooxazol-5-yl}-amide | 453.2 | 5.02 |
| 178 | thiophen-3-yl | [2,3']Bithiophenyl-5-carboxylic acid {2-[methyl-(1-methyl-piperidin-4-yl)-amino]-benzooxazol-5-yl}-amide | 453.2 | 4.93 |
| 179 | 4-Me-phenyl | 5-p-Tolyl-thiophene-2-carboxylic acid {2-[methyl-(1-methyl-piperidin-4-yl)-amino]-benzooxazol-5-yl}-amide | 461.2 | 5.52 |
| 180 | 3-F-phenyl | 5-(3-Fluoro-phenyl)-thiophene-2-carboxylic acid {2-[methyl-(1-methyl-piperidin-4-yl)-amino]-benzooxazol-5-yl}-amide | 465.2 | 5.24 |

-continued

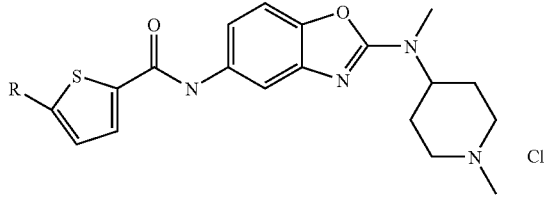

| Ex. | R | Name | Found for (M + H)+ | RT, min. |
|---|---|---|---|---|
| 181 | 3-Cl-phenyl | 5-(3-Chloro-phenyl)-thiophene-2-carboxylic acid {2-[methyl-(1-methyl-piperidin-4-yl)-amino]-benzooxazol-5-yl}-amide | 481.2 | 5.58 |
| 182 | 3-MeO-phenyl | 5-(3-Methoxy-phenyl)-thiophene-2-carboxylic acid {2-[methyl-(1-methyl-piperidin-4-yl)-amino]-benzooxazol-5-yl}-amide | 477.2 | 5.16 |
| 183 | benzo[1,3]dioxol-5-yl | 5-Benzo[1,3]dioxol-5-yl-thiophene-2-carboxylic acid {2-[methyl-(1-methyl-piperidin-4-yl)-amino]-benzooxazol-5-yl}-amide | 491.2 | 4.99 |
| 184 | 4-HO-phenyl | 5-(4-Hydroxy-phenyl)-thiophene-2-carboxylic acid {2-[methyl-(1-methyl-piperidin-4-yl)-amino]-benzooxazol-5-yl}-amide | 463.2 | 4.23 |
| 185 | 5-Cl-thien-2-yl | 5'-Chloro-[2,2']bithiophenyl-5-carboxylic acid {2-[methyl-(1-methyl-piperidin-4-yl)-amino]-benzooxazol-5-yl}-amide | 487.1 | 5.68 |

Example 186

N-{2-[Methyl-(1-methyl-piperidin-4-yl)-amino]-benzooxazol-5-yl}-4-(2-methyl-thiazol-4-yl)-benzamide

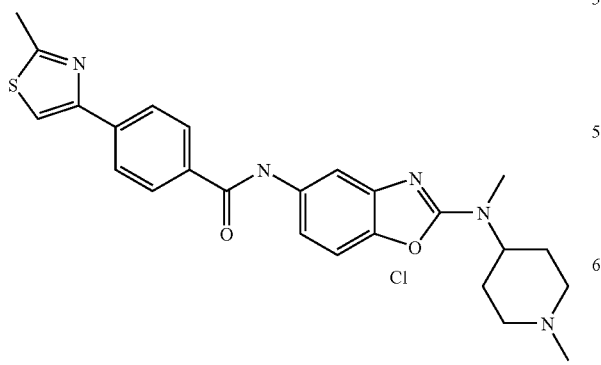

Combine 4-(2-methyl-1,3-thiazol-4-yl)benzoic acid (55 mg, 0.251 mmol), TBTU (74 mg, 0.232 mmol), and N2-Methyl-N2-(1-methyl-piperidin-4-yl)-benzooxazole-2,5-diamine (46 mg, 0.177 mmol) in DMF (1.0 mL) and shake at room temperature. Add acetone (2.0 mL) a put the mixture on an SCX cartridge (previously conditioned with MeoH). Wash with acetone (3×3.0 mL) non basic impurities and then with MeOH (3×3.0 mL). Eluting with a 2N solution of NH3 in MeOH (4.0 ml) and concentrate to afford the title compound (87 mg, 100%). LC/MS, RT=4.45 min., mass spectrum (m/z) found (M+H)+: 462.2. The material is dissolved in MeOH and treated with 2M HCl in ether (2.0 mL). Organic solvent is removed in vacuo and the resulting precipitate is collected to give 96 mg of the hydrochloride salt.

We claim:
1. A compound of formula I

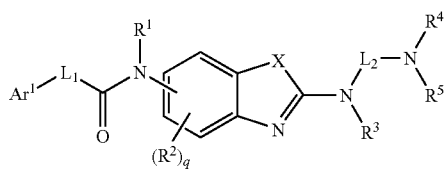

wherein:

X is O, or S;

q is 0 or 1 for $R^2$ other than hydrogen;

$Ar^1$ is a phenyl group optionally substituted with one to four groups independently selected from $C_1$-$C_8$ alkyl, $C_2$-$C_4$ alkenyl, $C_2$-$C_4$ alkynyl, hydroxy, $C_1$-$C_8$ alkoxy, phenyl, aryl, —O-aryl, —O-heteroaryl, —O-heterocyclic, heteroaryl, cycloalkyl, $C_1$-$C_4$ alkylaryl, $C_1$-$C_4$ alkylheteroaryl, $C_1$-$C_4$ alkyl-O-aryl, $C_1$-$C_4$ alkyl-O-heteroaryl, $C_1$-$C_4$ alkyl-O-heterocyclic, $C_1$-$C_4$ alkylcycloalkyl, cyano, —$(CH_2)_n NR^6 R^{6'}$, $C_1$-$C_4$ haloalkyl, $C_1$-$C_4$ haloalkoxy, halo, $(CH_2)_n COR^6$, $(CH_2)_n$ $NR^6 SO_2 R^{6'}$, —$(CH_2)_n C(O)NR^6 R^{6'}$, heterocyclic, and $C_1$-$C_4$ alkylheterocyclic; wherein the cycloalkyl, phenyl, aryl, heteroaryl and heterocyclic substituent are each optionally substituted with one to three groups independently selected from hydroxy, $C_1$-$C_6$ alkoxy, $C_1$-$C_4$ alkoxyalkyl, $C_1$-$C_4$ haloalkoxy, $C_1$-$C_4$ alkyl, halo, $C_1$-$C_4$ haloalkyl, nitro, cyano, amino, carboxamido, phenyl, aryl, alkylheterocyclic, heterocyclic, and oxo;

$L_1$ is a bond, or a divalent linker selected from the group consisting of $C_1$-$C_6$ alkyl, $C_2$-$C_6$ alkenyl, and —$OC_1$-$C_6$ alkyl;

$R^1$ is selected from the group consisting of hydrogen, $C_1$-$C_4$ alkyl and $C_1$-$C_4$ alkylcycloalkyl;

$R^2$ is independently selected from the group consisting of hydrogen, halo, $C_1$-$C_4$ haloalkyl, $C_1$-$C_4$ alkyl, and $C_1$-$C_4$ alkoxy;

$R^3$ is selected from the group consisting of hydrogen, $C_1$-$C_6$ alkyl, $C_2$-$C_6$ alkenyl, $C_3$-$C_8$ cycloalkyl, aryl, $C_1$-$C_4$ alkylaryl, $C_1$-$C_4$ alkylcycloalkyl, heterocyclic and $C_1$-$C_4$ alkylheterocyclic;

$L_2$ is $C_2$-$C_4$ alkyl;

each $R^4$ and $R^5$ is independently selected from the group consisting of hydrogen, $C_1$-$C_8$ alkyl, $C_2$-$C_8$ alkenyl, $C_3$-$C_8$ cycloalkyl, aryl, heteroaryl, $C_1$-$C_4$ alkylaryl, $C_1$-$C_4$ alkylheteroaryl, $C_1$-$C_4$ alkylcycloalkyl, $(CH_2)_n C(O)C_1$-$C_4$ alkyl, $CONR^6 R^{6'}$, $SO_2 R^6$, heterocyclic, and $C_1$-$C_4$ alkylheterocyclic; wherein each of the alkyl, alkenyl, cycloalkyl, aryl, or heterocyclic groups or subgroups is optionally substituted with one to three groups independently selected from $C_1$-$C_8$ alkyl, $C_2$-$C_8$ alkenyl, phenyl, $C_1$-$C_8$ haloalkyl, halo, hydroxy, —$OC_1$-$C_8$ haloalkyl, and alkylaryl;

n is an integer from 0 to 4; or a pharmaceutically acceptable salt, enantiomer, diastereomer or mixture of diastereomers thereof.

2. A compound according to claim 1 where X is O.

3. A compound according to claim 1 wherein X is S.

4. A compound according to claim 1 wherein $Ar^1$ is an optionally substituted phenyl.

5. A compound according to claim 1 wherein the group $L^1$ is a bond or a divalent linker selected from the group consisting of: —$CH_2 CH_2$—, —CH=CH—, and —$CH_2 CH_2 CH_2$—.

6. A compound according to claim 1 wherein $L^1$ is —CH=CH—.

7. A compound according to claim 1 wherein $R^4$ and $R^5$ are independently selected from the group consisting of $C_1$-$C_6$ alkyl, $C_1$-$C_6$ alkylamine, phenyl, benzyl, cyclopentyl, cyclohexyl, methylcyclopropyl and methylcyclobutyl.

8. A compound selected from the group consisting of:

4'-Fluoro-biphenyl-4-carboxylic acid {2-[(2-dimethylamino-ethyl)-methyl-amino]-benzothiazol-6-yl}-amide, 2'-Methyl-biphenyl-4-carboxylic acid {2-[(2-dimethylamino-ethyl)-methyl-amino]-benzothiazol-6-yl}-amide, 4'-Fluoro-biphenyl-4-carboxylic acid {2-[(3-diethylamino-propyl)-methyl-amino]-benzothiazol-6-yl}-amide, 4-Cyclohexyl-N-{2-[(2-dimethylamino-ethyl)-methyl-amino]-benzothiazol-6-yl}-benzamide, 2',4'-Difluoro-biphenyl-4-carboxylic acid {2-[(2-dimethylamino-ethyl)-methyl-amino]-benzothiazol-6-yl}-amide, 2'-Chloro-biphenyl-4-carboxylic acid {2-[(2-dimethylamino-ethyl)-methyl-amino]-benzothiazol-6-yl}-amide, 4'-Fluoro-2'-methyl-biphenyl-4-carboxylic acid {2-[(2-dimethylamino-ethyl)-methyl-amino]-benzothiazol-6-yl}-amide, 2',3'-Dichloro-biphenyl-4-carboxylic acid {2-[(2-dimethylamino-ethyl)-methyl-amino]-benzothiazol-6-yl}-amide, 2'-Chloro-4'-trifluoromethyl-biphenyl-4-carboxylic acid {2-[(2-dimethylamino-ethyl)-methyl-amino]-benzothiazol-6-yl}-amide, 4-Cyclohexyl-N-{2-[(2-dimethylamino-ethyl)-methyl-amino]-benzooxazol-5-yl}-benzamide, 4'-Fluoro-biphenyl-4-carboxylic acid {2-[(3-diethylamino-propyl)-methyl-amino]-benzooxazol-5-yl}-amide, 4-Cyclohexyl-N-{2-[(3-dimethylamino-propyl)-methyl-amino]-benzooxazol-5-yl}-benzamide, 4-Cyclohexyloxy-N-{2-[(2-dimethylamino-ethyl)-methyl-amino]-benzothiazol-6-yl}-benzamide, 4-Cyclohexylmethoxy-N-{2-[(2-dimethylamino-ethyl)-methyl-amino]-benzothiazol-6-yl}-benzamide, 4-Butyl-N-{2-[(2-dimethylamino-ethyl)-methyl-amino]-benzooxazol-5-yl}-benzamide, 4-Cyclohexyloxy-N-{2-[(2-dimethylamino-ethyl)-methyl-amino]-benzooxazol-5-yl}-benzamide, N-{2-[(2-Dimethylamino-ethyl)-methyl-amino]-benzooxazol-5-yl}-6-(4-fluoro-phenyl)-nicotinamide, 2'-Chloro-4'-trifluoromethoxy-biphenyl-4-carboxylic acid {2-[(2-dimethylamino-ethyl)-methyl-amino]-benzothiazol-6-yl}-amide, 2'-4'-Dimethyl-biphenyl-4-carboxylic acid {2-[(2-dimethylamino-ethyl)-methyl-amino]-benzothiazol-6-yl}-amide, N-{2-[(2-Dimethylamino-ethyl)-methyl-amino]-benzooxazol-5-yl}-4-phenoxy-benzamide, Biphenyl-4-carboxylic acid {2-[(2-dimethylamino-ethyl)-methyl-amino]-benzooxazol-5-yl}-amide, 4-Cyclohexylmethoxy-N-{2-[(2-dimethylamino-ethyl)-methyl-amino]-benzooxazol-5-yl}-benzamide, 5-(4-Fluoro-phenyl)-pyrazine-2-carboxylic acid {2-[(2-dimethylamino-ethyl)-methyl-amino]-benzooxazol-5-yl}-amide, N-{2-[(2-Dimethylamino-ethyl)-methyl-amino]-benzooxazol-5-yl}-4-isobutoxy-benzamide, 4'-Fluoro-biphenyl-4-carboxylic acid {2-[(2-dimethylamino-ethyl)-methyl-amino]-benzooxazol-5-yl}-amide, 2',4'-Dichloro-biphenyl-4-carboxylic acid {2-[(2-dimethylamino-ethyl)-methyl-amino]-benzooxazol-5-yl}-amide, 2'-Chloro-4'-methyl-biphenyl-4-carboxylic acid {2-[(2-dimethylamino-ethyl)-methyl-amino]-benzooxazol-5-yl}-amide, 4'-Chloro-2'-methyl-biphenyl-4-carboxylic acid {2-[(2-dimethylamino-ethyl)-methyl-amino]-benzooxazol-5-yl}-amide, 2'-Chloro-4'-methoxy-biphenyl-4-carboxylic acid {2-[(2-dimethylamino-ethyl)-methyl-amino]-benzothiazol-6-yl}-amide, 2'-Chloro-4'-fluoro-biphenyl-4-carboxylic acid {2-[(2-dimethylamino-ethyl)-methyl-amino]-benzothiazol-6-yl}-amide, 2',4'-Dichloro-biphenyl-4-carboxylic acid {2-[(2-dimethylamino-ethyl)-methyl-amino]-benzothiazol-6-yl}-amide, 4'-Chloro-2'-methyl-biphenyl-4-carboxylic acid {2-[(2-dimethylamino-ethyl)-methyl-amino]-benzothiazol-6-yl}-amide, and 2'-Chloro-4'-methyl-biphenyl-4-carboxylic acid {2-[(2-dimethylamino-ethyl)-methyl-amino]-benzothiazol-6-yl}-amide, or a pharmaceutically acceptable salt, enantiomer, diastereomer or mixture of diastereomers thereof.

9. A pharmaceutical composition comprising a compound of formula I and a pharmaceutically acceptable carrier and/or diluent.

10. A compound according to claim 1 wherein
$Ar^1$ is phenyl;
$L_1$ is a bond, or CH=CH;
$R^1$ and $R^2$ are both hydrogen;
$R^3$ is hydrogen or methyl; and
$L_2$ is ethyl or propyl.

* * * * *

UNITED STATES PATENT AND TRADEMARK OFFICE
CERTIFICATE OF CORRECTION

PATENT NO. : 7,838,543 B2  Page 1 of 1
APPLICATION NO. : 11/719576
DATED : November 23, 2010
INVENTOR(S) : James Peter Beck et al.

It is certified that error appears in the above-identified patent and that said Letters Patent is hereby corrected as shown below:

On the Title page, before the heading "Prior Publication Data," please add the following priority data:

"This application is a 371 of PCT/US05/45864, filed 12/16/2005 which claims benefit of U.S. Application 60/637,116, filed 12/17/2004.".

In column 137, line 35, in Claim 1, please delete "$L_2$is $C_2$-$C_4$alkyl;" and insert --$L_2$ is $C_2$-$C_4$ alkyl;--.

In column 138, line 45, in Claim 8, please delete "2'-4'-" and insert --2'4'- --.

In column 139, line 15, in Claim 8, please delete "amide,and" and insert --amide, and--.

Signed and Sealed this
Twenty-second Day of February, 2011

David J. Kappos
*Director of the United States Patent and Trademark Office*